United States Patent
Scheinberg et al.

(10) Patent No.: US 11,242,405 B2
(45) Date of Patent: Feb. 8, 2022

(54) MONOCLONAL ANTIGEN-BINDING PROTEINS TO INTRACELLULAR ONCOGENE PRODUCTS

(71) Applicants: MEMORIAL SLOAN-KETTERING CANCER CENTER, New York, NY (US); EUREKA THERAPEUTICS, INC., Emeryville, CA (US)

(72) Inventors: David A. Scheinberg, New York, NY (US); Tao Dao, New York, NY (US); Cheng Liu, Oakland, CA (US)

(73) Assignees: MEMORIAL SLOAN-KETTERING CANCER CENTER, New York, NY (US); EUREKA THERAPEUTICS, INC., Emeryville, CA (US)

( * ) Notice: Subject to any disclaimer, the term of this patent is extended or adjusted under 35 U.S.C. 154(b) by 100 days.

(21) Appl. No.: 15/710,384

(22) Filed: Sep. 20, 2017

(65) Prior Publication Data

US 2018/0134804 A1 May 17, 2018
US 2021/0332150 A9 Oct. 28, 2021

Related U.S. Application Data

(63) Continuation of application No. PCT/US2016/023247, filed on Mar. 18, 2016.

(60) Provisional application No. 62/136,117, filed on Mar. 20, 2015.

(51) Int. Cl.
| | | |
|---|---|---|
| C07K 16/40 | (2006.01) | |
| C07K 16/28 | (2006.01) | |
| A61K 47/68 | (2017.01) | |
| A61K 39/00 | (2006.01) | |

(52) U.S. Cl.
CPC .......... *C07K 16/40* (2013.01); *A61K 39/0011* (2013.01); *A61K 47/6871* (2017.08); *C07K 16/2809* (2013.01); *C07K 2317/14* (2013.01); *C07K 2317/21* (2013.01); *C07K 2317/31* (2013.01); *C07K 2317/34* (2013.01); *C07K 2317/54* (2013.01); *C07K 2317/55* (2013.01); *C07K 2317/56* (2013.01); *C07K 2317/565* (2013.01); *C07K 2317/567* (2013.01); *C07K 2317/622* (2013.01); *C07K 2317/732* (2013.01); *C07K 2317/92* (2013.01); *C07K 2319/70* (2013.01)

(58) Field of Classification Search
CPC ..... C07K 16/40; A61K 39/00; A61K 47/6871
See application file for complete search history.

(56) References Cited

U.S. PATENT DOCUMENTS

| | | | |
|---|---|---|---|
| 4,898,932 A | 2/1990 | Carney | |
| 5,443,956 A * | 8/1995 | Carney | C07K 14/82 |
| | | | 435/7.23 |
| 5,985,587 A | 11/1999 | Niman et al. | |
| 7,709,002 B1 | 5/2010 | Schlom et al. | |
| 9,074,000 B2 * | 7/2015 | Scheinberg | C07K 16/2833 |
| 9,540,448 B2 * | 1/2017 | Scheinberg | A61K 47/6849 |
| 10,040,865 B2 * | 8/2018 | Scheinberg | C07K 16/32 |
| 2004/0197328 A1 * | 10/2004 | Young | A61K 51/1096 |
| | | | 424/141.1 |
| 2004/0258693 A1 * | 12/2004 | Young | C07K 16/3023 |
| | | | 424/155.1 |
| 2014/0271644 A1 | 9/2014 | Scheinberg et al. | |
| 2014/0294841 A1 | 10/2014 | Scheinberg et al. | |
| 2015/0037334 A1 | 2/2015 | Kufer et al. | |
| 2018/0086832 A1 * | 3/2018 | Vogelstein | C07K 16/32 |

FOREIGN PATENT DOCUMENTS

WO WO-2012135854 A2 * 10/2012 ......... A61K 47/6851

OTHER PUBLICATIONS

Browning and Krausa (Immunology Today Apr. 1996 17 (4): 165-170) (Year: 1996).*
Almagro & Fransson, Frontiers in Bioscience 2008; 13:1619-33 (Year: 2008).*
Lee et al. (J. Mol. Biol. 2004 340:1073-1093) (Year: 2004).*
Dillman R.O. (Cancer Investigation 2001 19(8): 833-841) (Year: 2001).*
Chames et al. (British J. of Pharmacology, 2009, 157, 220-233) (Year: 2009).*
Cuesta et al., "Multivalent Antibodies: When Design Surpasses Evolution," Trends in Biotechnology 28(7): 355-362 (2010).
Dao et al., "Identification of a Human Cyclin D1-Derived Peptide that Induces Human Cytotoxic CD4 T Cells," PLoS One 4(8):e6730 (2009).
Smith et al., "Oncogenic Mutations in ras Create HLA-A2.1 Binding Peptides But Affect Their Extracellular Antigen Processing," International Immunology 9(8):1085-1093 (1997).
International Search Report and Written Opinion for PCT/US2016/023247 (dated Oct. 5, 2016).

* cited by examiner

Primary Examiner — Peter J Reddig

(57) ABSTRACT

Antigen binding proteins specific for an HLA-A2 restricted Ras peptide are disclosed. The antigen binding proteins encompass antibodies in a variety of forms, including full-length antibodies, substantially intact antibodies, Fab fragments, F(ab')2 fragments, and single chain Fv fragments. Fusion proteins, such as scFv fusions with immunoglobulin or T-cell receptor domains, and bispecific antibodies incorporating the specificity of the antigen binding region for each peptide are also contemplated by the disclosure. Furthermore, immunoconjugates may include antibodies to which is linked a radioisotope, fluorescent or other detectable marker, cytotoxin, or other molecule are also encompassed by the disclosure. Among other things, immunoconjugates can be used for delivery of an agent to elicit a therapeutic effect or to facilitate an immune effector function.

29 Claims, 22 Drawing Sheets

Specification includes a Sequence Listing.

MONOCLONAL ANTIGEN-BINDING PROTEINS TO INTRACELLULAR ONCOGENE PRODUCTS

CROSS-REFERENCE TO RELATED APPLICATIONS

This application is a continuation of PCT/US2016/023247 filed on Mar. 18, 2016 which published as WO 2016/154047 on Sep. 29, 2016, and which claims the priority of U.S. Provisional Application No. 62/136,117, filed Mar. 20, 2015; the entire contents of each are hereby incorporated in their entirety into the present disclosure.

SEQUENCE LISTING

The instant application contains a Sequence Listing, created on Mar. 18, 2015; the file, in ASCII format, is designated 3314061AWO_ST25.txt and is 77.8 kilobytes in size. The file is hereby incorporated by reference in its entirety into the instant application.

BACKGROUND OF THE DISCLOSURE

Technical Field

The present disclosure relates generally to antigen-binding protein molecules involved in immune function. More particularly, the present disclosure relates to recombinant antibodies, chimeric antigen receptors and fragments or portions thereof with binding specificity for Ras proteins.

Background Information

Antibodies are increasingly being used as therapeutic agents to fight cancer, autoimmune disease and infection. Therapeutic antibodies have been exploited based on their multiple mechanisms of action, which include the following: 1) naked antibodies killing tumor cells directly by ADCC or CDC (e.g. trastuzumab), 2) blocking or stimulating a cell membrane molecule to induce cell death (e.g. cetuximab), 3) neutralizing a secreted moiety (e.g. bevacizumab), 4) killing via an attached moiety such as a drug, toxin, radioisotope and 5) modulating the immune system via T cell effector functions.

In almost all cases, to generate a therapeutic benefit, antibodies have to possess certain properties including high affinity for their targeted antigen, minimal acute and long-term side effects, and in specific applications, high affinity for human Fc receptors (4). In addition, the targeted antigen has to be expressed in tumors but not on normal tissues (specificity or selectivity), consistently expressed in the specific tumor among patients and within patients (low heterogeneity), and should either be essential for the survival of the cancer cell or unlikely to be down regulated.

Ras is the most important oncogene in human cancers as it is mutated and involved in some of the most lethal cancers including cancers of the lung, pancreas, colon and rectum, among many others. Ras proteins are small GTPases that play a central role in transducing signals that regulate cell growth, differentiation and survival. All mammalian cells express 3 closely related Ras proteins, K-Ras, N-Ras and H-Ras, that promote oncogenesis when mutations occur at codons 12, 13 or 61. K-Ras mutations are far more frequently observed in cancer and are associated with >30% of all human cancers (up to 90% in pancreatic cancer) and are one of the first identified and the most common oncogenes found in human cancer. Because Ras is expressed in all normal cells, a safe and effective drug must be selective for the mutated Ras protein form alone. However, because the mutant Ras that is associated with cancers is so similar to the normal Ras protein found in all human cells, (the mutant differing by a single amino acid,) and because Ras's oncogenic function is not a mutated enzyme targetable by a small molecule in the traditional sense, it has been difficult to make a drug selective for Ras proteins. No drug for Ras is FDA approved for human use. Therefore, there is an important unmet need for such a drug to treat hundreds of thousands of patients with Ras associated cancers and leukemias.

Therapeutic monoclonal antibodies (mAbs) are highly specific and potent drugs, capable of initiating immunologic attack on tumor cells. Immune effector functions of mAbs include antibody-dependent cellular cytotoxicity (ADCC), complement-dependent cytotoxicity (CDC), antibody-dependent cellular phagocytosis (ADCP) and direct killing of the target cells. In addition, mAbs are highly versatile therapeutics. They can be conjugated to radioactive isotopes, toxins, or drugs, or carriers of such drugs, directly or by means of multi-step targeting, to specifically deliver more potent therapy to cancer cells. Furthermore, mAbs can also be engineered into chimeric antigen receptor (CAR) or bispecific T cell engager forms (T-BiTE), that bring powerful T cell cytotoxicity against the mAb-targeted cancer cells. Cytokines or other pro-inflammatory agents may be attached. All therapeutic mAbs currently marketed in the USA target extracellular or cell-surface molecules, while many important oncogenes and disease targets are intracellular.

But, unlike small molecule drugs that cross the cell membrane, mAbs cannot cross the membrane to access intracellular proteins like Ras and therefore, traditional antibody-based strategies targeting cell surface antigens are unavailable. Instead, immunotherapeutic approaches targeting Ras have been focused on generating T cell responses against the Ras-derived peptide epitopes presented on tumor cells by both MHC class I and class II. Though initial results suggest that Ras mutation-derived epitopes could be cancer-specific targets for T cell immunotherapy against a wide range of human cancers, peptide vaccines derived from Ras mutations have been evaluated in clinical trials in patients with pancreatic and other cancers, but clinical efficacy was not observed.

Accordingly, there remains a need for immunotherapeutics, including antibodies, which effectively target intracellular oncogenic proteins.

SUMMARY OF THE DISCLOSURE

The present disclosure is based on the identification of Ras-specific binding protein molecules, amino acid sequences of which can be used to generate a variety of antigen-binding proteins, for example, an antibody specific for Ras or for Ras mutant peptide variants having a single amino acid substitution.

The present disclosure identifies and characterizes antigen-binding proteins, such as antibodies, that are able to target cytosolic/intracellular proteins, for example, the Ras oncoprotein. The disclosed antibodies target a peptide/MHC complex as it would typically appear on the surface of a cell following antigen processing of Ras protein and presentation by the cell. In that regard, the antibodies mimic T-cell receptors in that the antibodies have the ability to specifically recognize and bind to a peptide in an MHC-restricted fashion, that is, when the peptide is bound to an MHC antigen. The peptide/MHC complex recapitulates the antigen as it would typically appear on the surface of a cell following antigen processing and presentation of the Ras protein to a T-cell.

The antibodies disclosed specifically recognize and bind to a Ras peptide/HLA-A2 complex, particularly a Ras/HLA-A0201 complex. Examples of peptides that are recognized by the antigen-binding proteins of the disclosure as part of an HLA-peptide complex include, but are not limited to, those shown in Table 11, for example, a peptide with the amino acid sequence KLVVVGAVGV (Ras10-G12V; SEQ ID NO: 111)

In one aspect, therefore, the disclosure relates to an isolated antibody, or antigen-binding fragment/portion thereof, that binds to a peptide with the amino acid sequence, KLVVVGAVGV (SEQ ID NO: 111), when said peptide is bound to an MHC antigen, such as HLA-A2.

In another aspect, therefore, the disclosure relates to an recombinant antigen-binding protein or antigen-binding fragment/portion thereof comprising one of:
  (A) an antigen binding region having the amino acid sequence of one of SEQ ID NOS: 81, 82, 83, 84, 85, 86, 87, or 88;
  (B) an antigen binding region comprising a $V_H$ and $V_L$, respectively, with amino acid sequences selected from SEQ ID NOs: 7 and 9; 17 and 19; 27 and 29; 37 and 39; 47 and 49; 57 and 59; 67 and 69; and 77 and 79; or
  (C) an antigen binding region comprising:
  (i) light chain complementarity determining regions (LC-CDRs) LC-CDR1, LC-CDR2 and LC-CDR3, with amino acid sequences SEQ ID NO: 4, SEQ ID NO: 5, and SEQ ID NO: 6, respectively and heavy chain CDRs (HC-CDRs) HC-CDR1, HC-CDR2 and HC-CDR3, with amino acid sequences SEQ ID NO: 1, SEQ ID NO: 2, and SEQ ID NO: 3, respectively;
  (ii) light chain complementarity determining regions (LC-CDRs) LC-CDR1, LC-CDR2 and LC-CDR3, with amino acid sequences SEQ ID NO: 14, SEQ ID NO: 15, and SEQ ID NO: 16, respectively and (b) heavy chain CDRs (HC-CDRs) HC-CDR1, HC-CDR2 and HC-CDR3, with amino acid sequences SEQ ID NO: 11, SEQ ID NO: 12, and SEQ ID NO: 13, respectively;
  (iii) light chain complementarity determining regions (LC-CDRs) LC-CDR1, LC-CDR2 and LC-CDR3, with amino acid sequences SEQ ID NO: 24, SEQ ID NO: 25, and SEQ ID NO: 26, respectively and (b) heavy chain CDRs (HC-CDRs) HC-CDR1, HC-CDR2 and HC-CDR3, with amino acid sequences SEQ ID NO: 21, SEQ ID NO: 22, and SEQ ID NO: 23, respectively;
  (iv) light chain complementarity determining regions (LC-CDRs) LC-CDR1, LC-CDR2 and LC-CDR3, with amino acid sequences SEQ ID NO: 34, SEQ ID NO: 35, and SEQ ID NO: 36, respectively and (b) heavy chain CDRs (HC-CDRs) HC-CDR1, HC-CDR2 and HC-CDR3, with amino acid sequences SEQ ID NO: 31, SEQ ID NO: 32, and SEQ ID NO: 33, respectively;
  (v) light chain complementarity determining regions (LC-CDRs) LC-CDR1, LC-CDR2 and LC-CDR3, with amino acid sequences SEQ ID NO: 44, SEQ ID NO: 45, and SEQ ID NO: 46, respectively and (b) heavy chain CDRs (HC-CDRs) HC-CDR1, HC-CDR2 and HC-CDR3, with amino acid sequences SEQ ID NO: 41, SEQ ID NO: 42, and SEQ ID NO: 43, respectively;
  (vi) light chain complementarity determining regions (LC-CDRs) LC-CDR1, LC-CDR2 and LC-CDR3, with amino acid sequences SEQ ID NO: 54, SEQ ID NO: 55, and SEQ ID NO: 56, respectively and (b) heavy chain CDRs (HC-CDRs) HC-CDR1, HC-CDR2 and HC-CDR3, with amino acid sequences SEQ ID NO: 51, SEQ ID NO: 52, and SEQ ID NO: 53, respectively;
  (vii) light chain complementarity determining regions (LC-CDRs) LC-CDR1, LC-CDR2 and LC-CDR3, with amino acid sequences SEQ ID NO: 64, SEQ ID NO: 65, and SEQ ID NO: 66, respectively and (b) heavy chain CDRs (HC-CDRs) HC-CDR1, HC-CDR2 and HC-CDR3, with amino acid sequences SEQ ID NO: 61, SEQ ID NO: 62, and SEQ ID NO: 63, respectively; or
  (viii) light chain complementarity determining regions (LC-CDRs) LC-CDR1, LC-CDR2 and LC-CDR3, with amino acid sequences SEQ ID NO: 74, SEQ ID NO: 75, and SEQ ID NO: 76, respectively and (b) heavy chain CDRs (HC-CDRs) HC-CDR1, HC-CDR2 and HC-CDR3, with amino acid sequences SEQ ID NO: 71, SEQ ID NO: 72, and SEQ ID NO: 73, respectively.

In a related aspect, the disclosure relates to a recombinant antigen-binding protein or antigen-binding fragment thereof, wherein the antigen-binding protein is an antibody or chimeric antigen receptor (CAR) that specifically binds to a Ras peptide in conjunction with HLA2. The recombinant antibody is a full-length antibody, that is an intact or substantially intact antibody, a Fab fragment, a F(ab')2 fragment or a single chain variable fragment (scFv), or comprises these elements.

In the recombinant antigen-binding protein, whether an antibody or CAR, the antigen-binding region specifically binds to an epitope of an HLA-2/Ras peptide complex.

The antigen binding proteins of the present disclosure demonstrated binding to a set of decamer and nonamer peptides containing the prevalent ras codon 12 mutations that are predicted minimal epitopes for HLA-A2. The decamers are based on amino acids 5-14 of ras wild-type, KLVVVGAGGV (SEQ ID NO: 110), while the nonamers correspond to amino acids 6-14 of ras wild-type, LVVVGAGGV (SEQ ID NO: 115).

Peptides that are recognized by the antigen-binding proteins of the disclosure as part of an HLA-Ras peptide complex include, but are not limited to, a 9 amino acid peptide with the amino acid sequence LVVVGAGGV (Ras9-WT, SEQ ID NO:115); and single amino acid substitutions thereof: LVVVGAVGV (Ras9-G12V, SEQ ID NO: 116); and LVVVGACGV (Ras9-G12C, SEQ ID NO: 117); and LVVVGADGV (Ras9-G12D, SEQ ID NO: 118) as well as a 10 amino acid peptide with the amino acid sequence KLVVVGAGGV (Ras10-WT, SEQ ID NO: 110); and single amino acid substitutions thereof: KLVVVGAVGV (Ras10-G12V SEQ ID NO: 111); KLVVVGACGV (Ras10-G12C SEQ ID NO: 112); and KLVVVGADGV (Ras10-G12D SEQ ID NO: 113) and KLVWGASGV (R10-G12S SEQ ID NO: 114). In some embodiments, the peptide is recognized in association with an HLA antigen that is HLA-A2.

In yet another aspect, the recombinant antigen-binding protein of the disclosure is a scFv comprising an amino acid sequence selected from the group consisting of SEQ ID NOS: 81, 82, 83, 84, 85, 86, 87 and 88.

In some embodiments, the antigen-binding proteins or antigen-binding fragment/portion thereof binds to a peptide with the amino acid sequence of SEQ ID NO: 111 with an affinity in the range of 8.0 to 10 nM, in some embodiments in the range of 8.5 to 9.5 nM and in some embodiments in the range of 9.76 to 9.25 nM.

In a related aspect, the recombinant antigen-binding protein is a fusion protein comprising an antigen-binding region as disclosed in any of Tables 1-8 or a bispecific antibody, for example as shown in Table 10.

In another aspect, the disclosure relates to an immunoconjugate comprising a first component which is an antigen-binding protein, or antigen-binding fragment thereof as disclosed herein. The immunoconjugate comprises a second component that is a cytotoxin, a detectable label, a radioisotope, a therapeutic agent, a binding protein or a molecule having a second amino acid sequence. Where the second component is a binding protein or second antibody, the binding protein or second antibody has binding specificity for a target that is different from the HLA-peptide complex.

In a related aspect, the present disclosure relates to bispecific antibodies, including bispecific T-cell engaging antibodies comprising an antigen-binding protein or functional fragment thereof as described herein.

In another related aspect, the present disclosure relates to an antigen binding protein conjugated to a radionuclide for use in radioimmunotherapy (RIT) to deliver cytotoxic radiation to a target cell.

In a related aspect, the present disclosure relates to nucleic acids encoding the antigen-binding proteins of the disclosures, vectors/genetic constructs and cells comprising the nucleic acids that encode the antigen-binding proteins including CAR constructs and CAR T-cell antibodies comprising an antigen-binding protein or functional fragment introduced into a T cell as described herein.

In still other aspects, the disclosure relates to the use of an antigen-binding protein or antigen-binding fragment/portion thereof that binds specifically to an epitope within a variant of wild type Ras peptide, KLVVVGAGGV (SEQ ID NO: 110, amino acids 5-14) or LVVVGAGGV (SEQ ID NO: 115, amino acids 6-14) with a single amino acid substitution at position 12 for use in identifying and/or killing cells bearing a RAS mutant peptide that is displayed on the cell surface in conjunction with an MHC antigen such as HLA-A2.

DETAILED DESCRIPTION OF THE DISCLOSURE

Figure 1A:
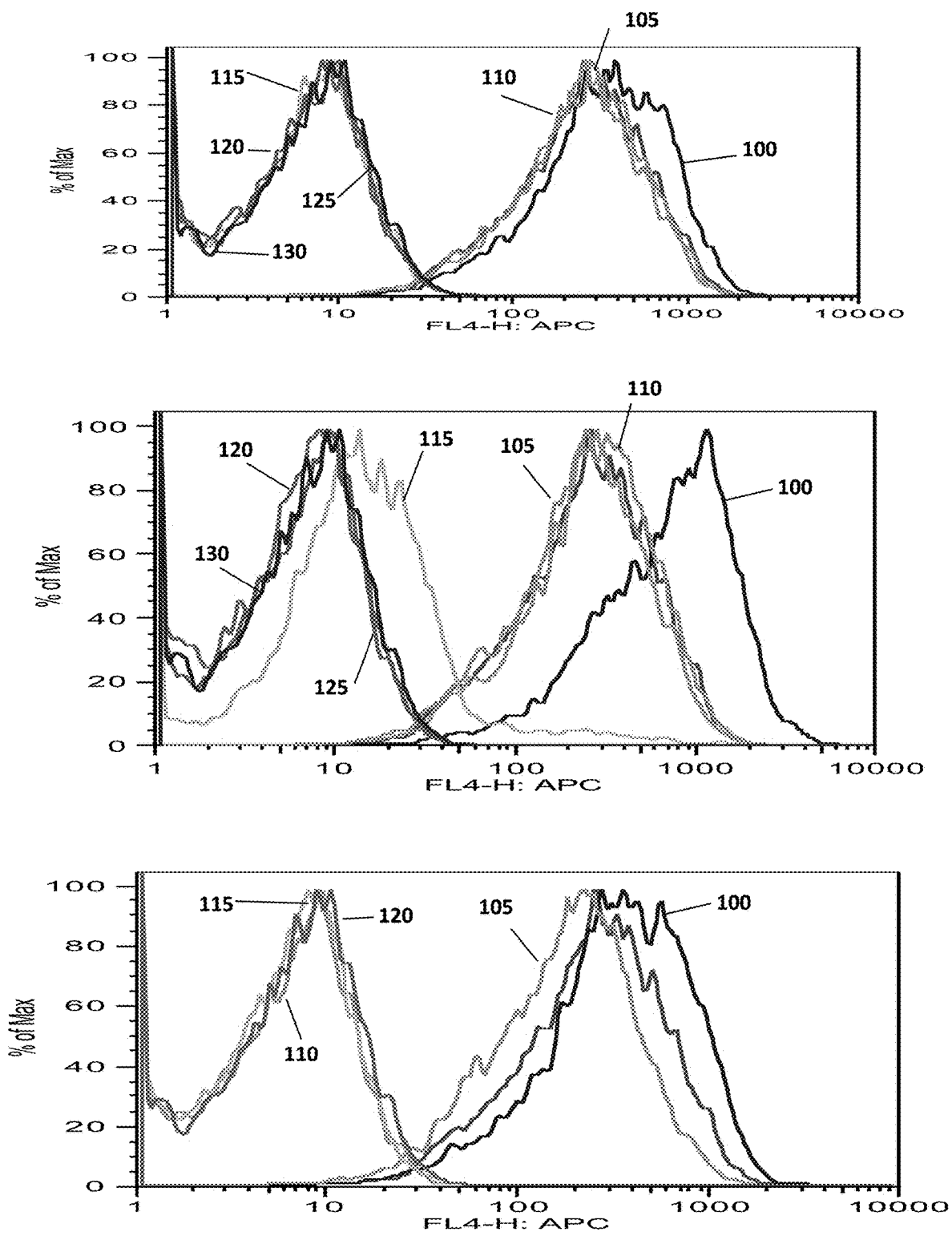
FIGS. 1A-D show stabilization of HLA-A2 molecule by RAS G12-derived peptides. T2 cells (TAP$^-$, HLA-A0201$^+$) were incubated overnight at 37° C. at 1×10$^6$ cells/ml in FCS-free RPMI medium supplemented with 10 µg/ml human beta 2m (b2M, Sigma, St Louis, Mo., USA) in the absence or presence of RAS10-WT (top panel), RAS10-G12V (middle panel), RAS10-G12C (lower panel) peptides (FIG. 1A), RAS10-G12D (upper panel), or a control peptide derived from hepatitis B virus, HBV (lower panel) (FIG. 1B). Binding of the peptides to HLA-A2 molecule was measured by staining T2 cells with mouse anti-HLA-A2 mAb conjugated to FITC. Red line shows BB7 staining on T2 cells alone. 100, 105, and 110 show BB7 staining on T2 cells pulsed with peptides at 50, 10 and 2 µg/ml, respectively. 115, 120, and 125 lines show the isotype control (mouse IgG2b) staining on T2 cells pulsed with peptides at 50, 10 and 2 µg/ml, respectively. 130 shows isotype staining on T2 cells alone. Similarly, binding of peptides to HLA-A2 was measured by BB7 staining on T2 cells pulsed with RAS9-WT (upper panel), RAS9-G12V (middle panel), RAS9-G12C (lower panel) (FIG. 1C), RAS9-G12D upper panel) or control HBV (lower panel) (FIG. 1D). 135: T2 cells alone. 140, 145, 150: peptides at 50, 10 and 2 µg/ml, respectively. Isotype control did not show any binding to T2 cells and therefore, were not shown.
Figure 1B:
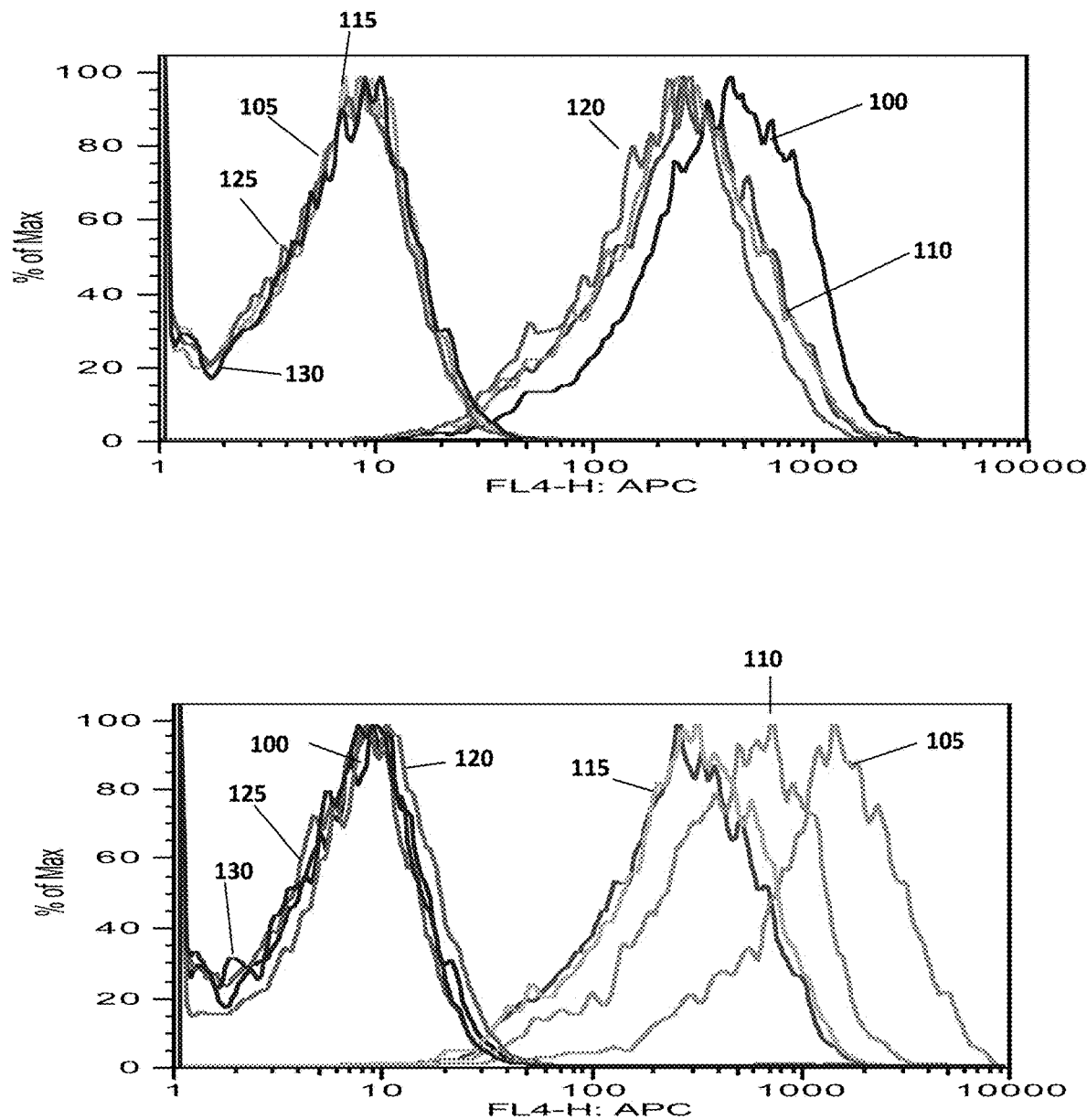

All patents, publications, applications and other references cited herein are hereby incorporated in their entirety into the present application.

In practicing the present disclosure, many conventional techniques in molecular biology, microbiology, cell biology, biochemistry, and immunology are used, which are within the skill of the art. These techniques are described in greater detail in, for example, Molecular Cloning: a Laboratory Manual 3$^{rd}$ edition, J. F. Sambrook and D. W. Russell, ed. Cold Spring Harbor Laboratory Press 2001; Recombinant Antibodies for Immunotherapy, Melvyn Little, ed. Cambridge University Press 2009; "Oligonucleotide Synthesis" (M. J. Gait, ed., 1984); "Animal Cell Culture" (R. I. Freshney, ed., 1987); "Methods in Enzymology" (Academic Press, Inc.); "Current Protocols in Molecular Biology" (F. M. Ausubel et al., eds., 1987, and periodic updates); "PCR: The Polymerase Chain Reaction", (Mullis et al., ed., 1994); "A Practical Guide to Molecular Cloning" (Perbal Bernard V., 1988); "Phage Display: A Laboratory Manual" (Barbas et al., 2001). The contents of these references and other references containing standard protocols, widely known to and relied upon by those of skill in the art, including manufacturers' instructions are hereby incorporated by reference as part of the present disclosure.

In the description that follows, certain conventions will be followed as regards the usage of terminology. Generally, terms used herein are intended to be interpreted consistently with the meaning of those terms as they are known to those of skill in the art.

An "antigen-binding protein" is a protein or polypeptide that comprises an antigen-binding region or antigen-binding portion, and has a strong affinity to another molecule to which it binds. Antigen-binding proteins encompass antibodies, antigen receptors and fusion proteins thereof. Antigen-binding proteins of the disclosure can be made recombinantly using methods known to those of skill in the art.

"Antibody" and "antibodies" as those terms are known in the art refer to antigen binding proteins that arise in the context of the immune system. The term "antibody" as referred to herein includes whole, full length antibodies and any fragment thereof in which the "antigen-binding portion" or "antigen-binding region" is retained or single chains thereof. A naturally occurring "antibody" is a glycoprotein comprising at least two heavy (H) chains and two light (L) chains inter-connected by disulfide bonds. Each heavy chain is comprised of a heavy chain variable region (abbreviated herein as $V_H$) and a heavy chain constant region. The heavy chain constant region is comprised of three domains, CH1, CH2 and CH3. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is, composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The term "antigen-binding portion" or "antigen-binding region" of an antibody (or simply "antigen portion"), as used herein, refers to that region or portion of the antibody that confers antigen specificity; fragments of antigen-binding proteins, for example antibodies, therefore, includes one or more fragments of an antibody that retain the ability to specifically bind to an antigen (e.g., an HLA-peptide complex). It has been shown that the antigen-binding function of an antibody can be performed by fragments of a full-length antibody. Examples of antigen-binding fragments encompassed within the term "antibody fragments" of an antibody include a Fab fragment, a monovalent fragment consisting of the $V_L$, $V_H$, $C_L$ and CH1 domains; a F(ab)$_2$ fragment, a bivalent fragment comprising two Fab fragments linked by a disulfide bridge at the hinge region; a Fd fragment consisting of the $V_H$ and CH1 domains; a Fv fragment consisting of the $V_L$ and $V_H$ domains of a single arm of an antibody; a dAb fragment (Ward et al., 1989 Nature 341:544-546), which consists of a $V_H$ domain; and an recombinant complementarity determining region (CDR).

Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al., 1988 Science 242:423-426; and Huston et al., 1988 Proc. Natl. Acad. Sci. 85:5879-5883). Such single chain antibodies are also intended to be encompassed within the term "antigen-binding portion" of an antibody. These antibody fragments are obtained using conventional techniques known to those of skill in the art, and the fragments are screened for utility in the same manner as are intact antibodies.

A "recombinant antibody" or "recombinant antigen-binding protein" or "synthetic antibodies" are generally generated using recombinant technology or using peptide synthetic techniques known to those of skill in the art.

Normal Ras and mutated forms yield proteins that are intracellular and therefore, cannot be accessed by conventional monoclonal antibody (mAb) therapy. Therefore, immunotherapeutic approaches targeting Ras have been focused on generating T cell responses against the Ras-derived peptide epitopes presented on tumor cells by both MHC class I and class II. Various peptides with 9, 10, 13, 17 or 21 amino acids (aa) spanning Ras mutation G12V, G12D, G12R and G12C, in the context of HLA-A0201 or other HLA haplotypes have been shown to induce both CD4 and CD8 T cell responses (ref). A 9 aa Ras-G12V peptide, LVVVGAVGV (SEQ ID NO: 117) was shown to be able to generate cytotoxic CD8 T cell clones that kill IFN-gamma pre-treated colon cancer cell line SW480 (HLA-A0201+ K-Ras-G12V mutation+). Similarly, Ras G12VT mutation-derived peptides KLVVVGAVGV—(10aa, p5-14, SEQ ID NO: 113) and LVVVGAVGV—(9 aa, p6-14, SEQ ID NO: 117) peptides induced CD8 T cell responses from patients with pancreatic cancer to kill pancreatic cancer cell line PaTu (Ras-G12V) and also colon cancer cell line SW480 (Ras-G12VT), in the context of HLA-A0201. These results suggest that Ras mutation-derived epitopes could be cancer-specific targets for T cell immunotherapy against a wide range of human cancers. Accordingly, peptide vaccines-derived from Ras mutations have been evaluated in clinical trials in patients with pancreatic and other cancers, but clinical efficacy was not observed.

Monoclonal antibodies that mimic the specificity of TCRs (TCR-like) can bind cell-surface complexes specific to cells expressing an intracellular protein, yet retain favorable pharmacokinetics and effector functions that make mAbs powerful therapeutics. TCR-like antibodies are especially interesting in oncology, because many of the most important tumor-associated and oncogenic proteins are nuclear or cytoplasmic.

Ras mutation-derived epitopes represent truly tumor-specific antigens and their wide expression in human cancer cells make them attractive targets for immunotherapy using TCR-like mAbs. We describe several TCR-like mAbs specific for Ras mutations, specifically for K-Ras G12 mutations. Several of the mAbs recognize only the mutated sequence and not the normal sequence when in the context of human MHC, HLA-A0201. Some embodiments of the antibodies are capable of killing human cancer cells when the mutant epitope (Ras G12V/MHC) is on the cell surface, but not when the normal Ras peptide is on the surface.

The scFvs of the disclosure selected by phage display were initially tested for their ability to bind to peptide presented on the surface of HLA-positive cells. After T2 cells were incubated in the presence of peptide, the scFvs could selectively recognize them using flow cytometry.

In some embodiments, the antigen binding proteins of the disclosure include antibodies that have the scFv sequence fused to the $2^{nd}$ and $3^{rd}$ constant domains of the heavy chain (CH$_{2, 3}$), forming the bottom third of the Fc region of a human immunoglobulin to yield a bivalent protein and fragments thereof, increasing the overall avidity and stability of the antibody. In addition, the Fc portion allows the direct conjugation of other molecules, including but not limited to fluorescent dyes, cytotoxins, radioisotopes etc. to the antibody for example, for use in antigen quantitation studies, to immobilize the antibody for affinity measurements using surface plasmon resonance (SPR), for targeted delivery of a therapeutic agent, to test for Fc-mediated cytotoxicity using CD16-expressing immune effector cells and many other applications.

The results presented here highlight the specificity, sensitivity and utility of the antigen binding proteins of the disclosure in targeting MHC-Ras oncoprotein complexes.

In one embodiment, therefore, the present disclosure relates to antigen-binding proteins and portions thereof, such as recombinant antibodies, that recognize a complex of a peptide/protein fragment derived from an intracellular protein, specifically Ras oncoprotein, and an MHC class I molecule, for example, as the complex might appear on the cell surface for recognition by a T-cell.

The molecules of the disclosure are based on the identification and selection of a single chain variable fragment (scFv) using phage display, the amino acid sequence of which confers the molecules' specificity for the MHC restricted peptide of interest and forms the basis of antigen binding proteins of the disclosure. The scFv, therefore, can be used to design a diverse array of "antibody" molecules, including, for example, full length antibodies, fragments thereof, such as Fab and F(ab')$_2$, minibodies, fusion proteins, including scFv-Fc fusions, multivalent antibodies, that is, antibodies that have more than one specificity for the same antigen or different antigens, for example, bispecific T-cell engaging antibodies (BiTE or T-BiTE), tribodies, etc. (see Cuesta et al., *Multivalent antibodies: when design surpasses evolution. Trends in Biotechnology* 28:355-362 2010). scFv may also be used to construct CARs which are introduced by various means known to the skilled artisan into living T cells to make cytotoxic CAR T cells.

In an embodiment in which the antigen-binding protein is a full length antibody, the heavy and light chains of an antibody of the disclosure may be full-length (e.g., an antibody can include at least one, and preferably two, complete heavy chains, and at least one, and preferably two, complete light chains) or may include an antigen-binding portion (a Fab, F(ab')$_2$, Fv or a single chain Fv fragment ("scFv")). In other embodiments, the antibody heavy chain constant region is chosen from, e.g., IgG1, IgG2, IgG3, IgG4, IgM, IgA1, IgA2, IgD, and IgE. In some embodiments, the immunoglobulin isotype is selected from IgG1, IgG2, IgG3, and IgG4, more particularly, IgG1 (e.g., human IgG1). The choice of antibody type will depend on the immune effector function that the antibody is designed to elicit.

In constructing a recombinant immunoglobulin, appropriate amino acid sequences for constant regions of various immunoglobulin isotypes and methods for the production of a wide array of antibodies are well known to those of skill in the art.

In some embodiments, the constant region of the antibody is altered, e.g., mutated, to modify the properties of the antibody (e.g., to increase or decrease one or more of: Fc receptor binding, antibody carbohydrate, for example glycosylation or fucosylation, the number of cysteine residues, effector cell function, or complement function).

In one embodiment, the antigen binding protein is an anti-RAS antigen-binding protein or fragment thereof having an antigen binding region that comprises the amino acid sequence of SEQ ID NO: 81 and specifically binds to KLVVVGAVGV (SEQ ID NO: 111)/HLA2. In other embodiments, the anti-RAS antigen-binding protein is a scFv, or scFv-Fc fusion protein, full length human IgG or fragment thereof with VH and VL regions or CDRs selected from Table 1.

TABLE 1

| | Ab #1 | | |
|---|---|---|---|
| CDRs: | 1 | 2 | 3 |
| VH | GGTFSSYA<br>(SEQ ID NO. 1) | IIPIFGKG<br>(SEQ ID NO. 2) | ARHIPTFSFDY<br>(SEQ ID NO. 3) |
| VL | SSNIGAGYD<br>(SEQ ID NO: 4) | GNS<br>(SEQ ID NO: 5) | QSYDSSLSGYV<br>(SEQ ID NO. 6) |

Full VH  QVQLVQSGAEVKKPGSSVKVSCKASGGTFSSYAISWVRQAPGQGLEWM
GGIIPIFGKGNYPQKFQGRVTITADESTGTAYMELSSLRSEDTAVYYCARHI
PTFSFDYWGQGTLVTVSS
(SEQ ID NO: 7)

VH
DNA
caggtgcagctggtgcagtctggggctgaggtgaagaagcctggggtcctcggtgaaggtctcctgcaag
gcttctggaggcaccttcagcagctatgctatcagctgggtgcgacaggcccctggacaagggcttgagt
ggatgggaggtatcatccctatctttggtaaaggaaactacccacagaagttccagggcagagtcacgat
taccgcggacgaatctacgggcacagcctacatggagctgagcagcctgagatctgaggacacggcc
gtgtattactgtgcgcgccatatcccgactttctctttcgattactggggtcaaggtactctggtgaccgtctcct
ca
(SEQ ID NO: 8)

Full VL  QSVLTQPPSVSGAPGQRVTISCTGSSSNIGAGYDVHWYQQLPGTAPKLLIY
GNSNRPSGVPDRFSGSKSGTSASLAITGLQAEDEADYYCQSYDSSLSGYV
FGTGTKVTVLG
(SEQ ID NO: 9)

VL
DNA
cagtctgtgttgacgcagccgccctcagtgtctggggcccagggcagagggtcaccatctcctgcactg
ggagcagctccaacatcggggcaggttatgatgtacactggtaccagcagcttccaggaacagcccccc
aaactcctcatctatggtaacagcaatcggccctcaggggtccctgaccgattctctggctccaagtctggc
acctcagcctccctggccatcactgggctccaggctgaggatgaggctgattattactgccagtcctatgac
agcagcctgagtggttatgtcttcggaactgggaccaaggtcaccgtcctaggt
(SEQ ID NO: 10)

scFv
QSVLTQPPSVSGAPGQRVTISCTGSSSNIGAGYDVHWYQQLPGTAPKLLIY
GNSNRPSGVPDRFSGSKSGTSASLAITGLQAEDEADYYCQSYDSSLSGYV
FGTGTKVTVLGSRGGGGSGGGGSGGGGSLEMAQVQLVQSGAEVKKPGS
SVKVSCKASGGTFSSYAISWVRQAPGQGLEWMGGIIPIFGKGNYPQKFQG
RVTITADESTGTAYMELSSLRSEDTAVYYCARHIPTFSFDYWGQGTLVTVS
S
(SEQ ID NO: 81)

DNA
(5'-3')
cagtctgtgttgacgcagccgccctcagtgtctggggcccagggcagagggtcaccatctcctgcactg
ggagcagctccaacatcggggcaggttatgatgtacactggtaccagcagcttccaggaacagcccccc
aaactcctcatctatggtaacagcaatcggccctcaggggtccctgaccgattctctggctccaagtctggc
acctcagcctccctggccatcactgggctccaggctgaggatgaggctgattattactgccagtcctatgac
agcagcctgagtggttatgtcttcggaactgggaccaaggtcaccgtcctaggtctagaggtggtggtggt
agcggcggcggcggctctggtggtggtggatccaggtgcagctggtgcagtctggggctgaggtgaag
aagcctggggtcctcggtgaaggtctcctgcaaggcttctggaggcaccttcagcagctatgctatcagctg
ggtgcgacaggcccctggacaagggcttgagtggatgggaggtatcatccctatctttggtaaaggaaac
tacccacagaagttccagggcagagtcacgattaccgcggacgaatctacgggcacagcctacatgga
gctgagcagcctgagatctgaggacacggccgtgtattactgtgcgcgccatatcccgactttctctttcgat
tactggggtcaaggtactctggtgaccgtctcctca
(SEQ ID NO: 89)

In one embodiment, the antigen binding protein is an anti-RAS antigen-binding protein or fragment thereof having an antigen binding region that comprises the amino acid sequence of SEQ ID NO: 82 and specifically binds to LVVVGAVGV (SEQ ID NO: 116)/HLA2 or KLVVVGAVGV (SEQ ID NO: 111)/HLA2. In other embodiments, the anti-RAS antigen-binding protein is a scFv, or scFv-Fc fusion protein or full length human IgG with VH and VL regions or CDRs selected from Table 2.

TABLE 2

| | Ab #2 | | |
|---|---|---|---|
| CDRs: | 1 | 2 | 3 |
| VH | GGTFSSYT (SEQ ID NO. 11) | FIPISGTV (SEQ ID NO. 12) | ARPLDVVTEDI (SEQ ID NO. 13) |
| VL | SSNIGAGYD (SEQ ID NO: 14) | GNS (SEQ ID NO: 15) | QSYDSSLSGSV (SEQ ID NO. 16) |
| Full VH | QVQLVQSGAEVKKPGSSVKVSCKASGGTFSSYTINWVRQAPGQGLEWM GGFIPISGTVNYAQKFQGRVTITADESTSTAYMELSSLRSEDTAVYYCARP LDWTEDIWGQGTLVTVSS (SEQ ID NO: 17) | | |
| VH DNA | caggtgcagctggtgcagtctggggctgaggtgaagaagcctgggtcctcggtgaaggtctcctgcaag gcttctggaggcaccttcagcagctatactatcaactgggtgcgacaggcccctggacaagggcttgag tggatgggagggttcatccctatctctggtacagtaaactacgcacagaagttccagggcagagtcacg attaccgcggacgaatccacgagcacagcctacatggaactgagcagcctgagatctgaggacactg ccgtgtattactgtgcgcgcccgctggactggactgaagatatctggggtcaaggtactctggtgaccgtc tcctca (SEQ ID NO: 18) | | |
| Full VL | QSVLTQPPSVSGAPGQRVTISCTGSSSNIGAGYDVHWYQQLPGTAPKLLI YGNSNRPSGVPDRFSGSKSGTSASLAITGLQAEDEADYYCQSYDSSLSG SVFGTGTKVTVLG (SEQ ID NO: 19) | | |
| VL DNA | Cagtctgtgttgacgcagccgccctcagtgtctggggcccagggcagagggtcaccatctcctgcact gggagcagctccaacatcggggcaggttatgatgtacactggtaccagcagcttccaggaacagcccc caaactcctcatctatggtaacagcaatcggccctcaggggtccctgaccgattctctggctccaagtctg gcacctcagcctccctggccatcactgggctccaggctgaggatgaggctgattattactgccagtcctat gacagcagcctgagtggttcagtcttcggaactgggaccaaggtcaccgtcctaggt (SEQ ID NO: 20) | | |
| scFv | QSVLTQPPSVSGAPGQRVTISCTGSSSNIGAGYDVHWYQQLPGTAPKLLI YGNSNRPSGVPDRFSGSKSGTSASLAITGLQAEDEADYYCQSYDSSLSG SVFGTGTKVTVLGSRGGGGSGGGGSGGGGSLEMAVQLVQSGAEVKKP GSSVKVSCKASGGTFSSYTINWVRQAPGQGLEWMGGFIPISGTVNYAQK FQGRVTITADESTSTAYMELSSLRSEDTAVYYCARPLDWTEDIWGQGTLV TVSS (SEQ ID NO: 82) | | |
| DNA (5'-3') | cagtctgtgttgacgcagccgccctcagtgtctggggcccagggcagagggtcaccatctcctgcact gggagcagctccaacatcggggcaggttatgatgtacactggtaccagcagcttccaggaacagcccc caaactcctcatctatggtaacagcaatcggccctcaggggtccctgaccgattctctggctccaagtctg gcacctcagcctccctggccatcactgggctccaggctgaggatgaggctgattattactgccagtcctat gacagcagcctgagtggttcagtcttcggaactgggaccaaggtcaccgtcctaggtctagaggtggtg gtggtagcggcggcggcggctctggtggtggtggatcccaggtgcagctggtgcagtctggggctgag gtgaagaagcctgggtcctcggtgaaggtctcctgcaaggcttctggaggcaccttcagcagctatacta tcaactgggtgcgacaggcccctggacaagggcttgagtggatgggagggttcatccctatctctggtac agtaaactacgcacagaagttccagggcagagtcacgattaccgcggacgaatccacgagcacagc ctacatggaactgagcagcctgagatctgaggacactgccgtgtattactgtgcgcgcccgctggactg gactgaagatatctggggtcaaggtactctggtgaccgtctcctca (SEQ ID NO: 90) | | |

In one embodiment, the antigen binding protein is an anti-RAS antigen-binding protein or fragment thereof having an antigen binding region that comprises the amino acid sequence of SEQ ID NO: 83 and specifically binds to KLVVVGAVGV (SEQ ID NO: 111)/HLA2. In other embodiments, the anti-RAS antigen-binding protein is a scFv, or scFv-Fc fusion protein or full length human IgG with VH and VL regions or CDRs selected from Table 3.

TABLE 3

Ab #3

| CDRs: | 1 | 2 | 3 |
|---|---|---|---|
| VH | GYTFTAYY (SEQ ID NO. 21) | MNTNNGAT (SEQ ID NO. 22) | ARGDISQDFADV (SEQ ID NO. 23) |
| VL | SGSIASNY (SEQ ID NO: 24) | EDN (SEQ ID NO: 25) | QSYDDINHWV (SEQ ID NO. 26) |

| | |
|---|---|
| Full VH | EVQLVQSGAEVKKPGASVKVSCKASGYTFTAYYLHWLRQAPGQGLEWM<br>GWMNTNNGATRYAQKFQDRVTMTRDTSINTAYMEMSGLSSDDTAMYYC<br>ARGDISQDFADVWGQGTLVTVSS<br>(SEQ ID NO: 27) |
| VH DNA | gaggtgcagctggtgcagtctggggctgaggtgaagaagcctggggcctcagtgaaggtctcctgcaa<br>ggcttctggatacaccttcaccgcctactatctgcactggctgcgacaggcccctggacaagggcttgag<br>tggatgggatggatgaatactaacaatggtgccacaaggtatgcacagaaatttcaggacagggtcac<br>catgaccagggacacgtccattaacacagcctacatggagatgagcgggctgtcatctgacgacaccg<br>ccatgtattactgtgcgcgcggtgatatctctcaggacttcgctgatgtttggggtcaaggtactctggtgac<br>cgtctcctca<br>(SEQ ID NO: 28) |
| Full VL | NFMLTQPHSVSESPGKTVTISCTGSSGSIASNYVQWYQQRPGSAPTILIYE<br>DNKRPSGVPDRFSGSIDSSSNSASLTISGLKTGDEADYYCQSYDDINHWV<br>FGGGTKLTVLG<br>(SEQ ID NO: 29) |
| VL DNA | aattttatgctgactcagccccactctgtgtcggagtctccggggaagacggtaaccatctcctgcaccgg<br>cagcagtggcagcattgccagcaactatgtgcagtggtatcagcagcgcccgggcagtgcccccacc<br>attctgatctatgaggataacaaaagaccctctggggtccctgatcggttctctggctccatcgacagctcc<br>tccaactctgcctccctcaccatctctggactgaagactggggacgaggctgactactactgtcagtcttat<br>gatgacatcaatcattgggtgttcggcggagggaccaagctgaccgtcctaggt<br>(SEQ ID NO: 30) |
| scFv | NFMLTQPHSVSESPGKTVTISCTGSSGSIASNYVQWYQQRPGSAPTILIYE<br>DNKRPSGVPDRFSGSIDSSSNSASLTISGLKTGDEADYYCQSYDDINHWV<br>FGGGTKLTVLGSRGGGGSGGGGSGGGGSLEMAEVQLVQSGAEVKKPG<br>ASVKVSCKASGYTFTAYYLHWLRQAPGQGLEWMGWMNTNNGATRYAQ<br>KFQDRVTMTRDTSINTAYMEMSGLSSDDTAMYYCARGDISQDFADVWGQ<br>GTLVTVSS<br>(SEQ ID NO: 83) |
| DNA (5'-3') | aattttatgctgactcagccccactctgtgtcggagtctccggggaagacggtaaccatctcctgcaccgg<br>cagcagtggcagcattgccagcaactatgtgcagtggtatcagcagcgcccgggcagtgcccccacc<br>attctgatctatgaggataacaaaagaccctctggggtccctgatcggttctctggctccatcgacagctcc<br>tccaactctgcctccctcaccatctctggactgaagactggggacgaggctgactactactgtcagtcttat<br>gatgacatcaatcattgggtgttcggcggagggaccaagctgaccgtcctaggtctagaggtggtggtg<br>gtagcggcggcggcggctctggtggtggtggatccgaggtgcagctggtgcagtctggggctgaggtg<br>aagaagcctggggcctcagtgaaggtctcctgcaaggcttctggatacaccttcaccgcctactatctgc<br>actggctgcgacaggcccctggacaagggcttgagtggatgggatggatgaatactaacaatggtgcc<br>acaaggtatgcacagaaatttcaggacagggtcaccatgaccagggacacgtccattaacacagcct<br>acatggagatgagcgggctgtcatctgacgacaccgccatgtattactgtgcgcgcggtgatatctctca<br>ggacttcgctgatgtttggggtcaaggtactctggtgaccgtctcctca<br>(SEQ ID NO: 91) |

In one embodiment, the antigen binding protein is an anti-RAS antigen-binding protein or fragment thereof having an antigen binding region that comprises the amino acid sequence of SEQ ID NO: 84 and specifically binds to KLVVVGAVGV (SEQ ID NO: 111)/HLA2. In other embodiments, the anti-RAS antigen-binding protein is a scFv, or scFv-Fc fusion protein or full length human IgG with VH and VL regions or CDRs selected from Table 4.

TABLE 4

Ab #4

| CDRs: | 1 | 2 | 3 |
|---|---|---|---|
| VH | GYTFTAYY (SEQ ID NO. 31) | MNTNNGAT (SEQ ID NO. 32) | ARGDISQDFADV (SEQ ID NO. 33) |
| VL | SGSIASNY (SEQ ID NO: 34) | EDN (SEQ ID NO: 35) | QSYDDINHWV (SEQ ID NO. 36) |

| | |
|---|---|
| Full VH | EVQLVQSGAEVKKPGASVKVSCKASGYTFTAYYLHWLRQAPGQGLEWM<br>GWMNTNNGATRYAQKFQDRVTMTRDTSINTAYMEMSGLSSDDTAMYYC<br>ARGDISQDFADVWGQGTLVTVSS<br>(SEQ ID NO: 37) |

TABLE 4-continued

| | |
|---|---|
| VH DNA | gaggtgcagctggtgcagtctggggctgaggtgaagaagcctggggcctcagtgaaggtctcctgcaa<br>ggcttctggatacaccttcaccgcctactatctgcactggctgcgacaggcccctggacaagggcttgag<br>tggatgggatggatgaatactaacaatggtgccacaaggtatgcacagaaatttcaggacagggtcac<br>catgaccagggacacgtccattaacacagcctacatggagatgagcgggctgtcatctgacgacaccg<br>ccatgtattactgtgcgcgcggtgatatctctcaggacttcgctgatgtttggggtcaaggtactctggtgac<br>cgtctcctca<br>(SEQ ID NO: 38) |
| Full VL | NFMLTQPHSVSESPGKTVTISCTGSSGSIASNYVQWYQQRPGSAPTILIYE<br>DNKRPSGVPDRFSGSIDSSSNSASLTISGLKTGDEADYYCQSYDDINHWV<br>FGGGTKLTVLG<br>(SEQ ID NO: 39) |
| VL DNA | aattttatgctgactcagccccactctgtgtcggagtctccggggaagacggtaaccatctcctgcaccgg<br>cagcagtggcagcattgccagcaactatgtgcagtggtatcagcagcgcccgggcagtgccccccacc<br>attctgatctatgaggataacaaaagaccctctggggtccctgatcggttctctggctccatcgacagctcc<br>tccaactctgcctccctcaccatctctggactgaagactggggacgaggctgactactactgtcagtcttat<br>gatgacatcaatcattgggtgttcggcggagggaccaagctgaccgtcctaggt<br>(SEQ ID NO: 40) |
| scFv | NFMLTQPHSVSESPGKTVTISCTGSSGSIASNYVQWYQQRPGSAPTILIYE<br>DNKRPSGVPDRFSGSIDSSSNSASLTISGLKTGDEADYYCQSYDDINHWV<br>FGGGTKLTVLGSRGGGGSGGGGSGGGGSLEMAEVQLVQSGAEVKKPG<br>ASVKVSCKASGYTFTAYYLHWLRQAPGQGLEWMGWMNTNNGATRYAQ<br>KFQDRVTMTRDTSINTAYMEMSGLSSDDTAMYYCARGDISQDFADVWGQ<br>GTLVTVSS<br>(SEQ ID NO: 84) |
| DNA (5'-3') | aattttatgctgactcagccccactctgtgtcggagtctccggggaagacggtaaccatctcctgcaccgg<br>cagcagtggcagcattgccagcaactatgtgcagtggtatcagcagcgcccgggcagtgccccccacc<br>attctgatctatgaggataacaaaagaccctctggggtccctgatcggttctctggctccatcgacagctcc<br>tccaactctgcctccctcaccatctctggactgaagactggggacgaggctgactactactgtcagtcttat<br>gatgacatcaatcattgggtgttcggcggagggaccaagctgaccgtcctaggtctagaggtggtggtg<br>gtagcggcggcggcggctctggtggtggtggatccgaggtgcagctggtgcagtctggggctgaggtg<br>aagaagcctggggcctcagtgaaggtctcctgcaaggcttctggatacaccttcaccgcctactatctgc<br>actggctgcgacaggcccctggacaagggcttgagtggatgggatggatgaatactaacaatggtgcc<br>acaaggtatgcacagaaatttcaggacagggtcaccatgaccagggacacgtccattaacacagcct<br>acatggagatgagcgggctgtcatctgacgacaccgccatgtattactgtgcgcgcggtgatatctctca<br>ggacttcgctgatgtttggggtcaaggtactctggtgaccgtctcctca<br>(SEQ ID NO: 92) |

In one embodiment, the antigen binding protein is an anti-RAS antigen-binding protein or fragment thereof having an antigen binding region that comprises the amino acid sequence of SEQ ID NO: 85 and specifically binds to KLVVVGAVGV (SEQ ID NO: 111)/HLA2. In other embodiments, the anti-RAS antigen-binding protein is a scFv, or scFv-Fc fusion protein or full length human IgG with VH and VL regions or CDRs selected from Table 5.

TABLE 5

| | Ab #5 | | |
|---|---|---|---|
| CDRs: | 1 | 2 | 3 |
| VH | GGSFSGYY<br>(SEQ ID NO. 41) | VNHSGNT<br>(SEQ ID NO. 42) | ARYFPPMIDV<br>(SEQ ID NO. 43) |
| VL | SSNIENNY<br>(SEQ ID NO. 44) | DNN<br>(SEQ ID NO. 45) | GTWDSSLSAYV<br>(SEQ ID NO. 46) |
| Full VH | QVQLQQWGAGLLKPSETLSLTCAVYGGSFSGYYWSIRQSPGKGLEWIG<br>EVNHSGNTNYNPSLKSRVTISLDTSKNQFSLKLNSVTAADTAVYYCARYFP<br>PMIDVWGQGTLVTVSS<br>(SEQ ID NO: 47) | | |
| VH DNA | caggtgcagctacagcagtggggcgcaggactgttgaaaccttcggagaccctgtccctcacctgcgct<br>gtctatggtgggtccttcagcggttactactggagctggatccgccagtccccaggaagggactggagt<br>ggattgggaagtcaatcatagtggcaacaccaactacaacccgtccctcaagagtcgagtcaccatttc<br>actagacacgtccaagaaccagttctccctgaaactgaactctgtgaccgccgcgacacgcgtgtat<br>tactgtgcgcgctacttccgccgatgatcgatgtttggggtcaaggtactctggtgaccgtctcctca<br>(SEQ ID NO: 48) | | |
| Full VL | QSVVTQPPSVSAAPGQKVTISCSGSSSNIENNYVSWYQQLPGTAPKLLIYD<br>NNKRPSGIPDRFSGSKSGTSATLGITGLQTGDEADYYCGTWDSSLSAYVF<br>GTGTKVTVLG<br>(SEQ ID NO: 49) | | |

TABLE 5-continued

| | |
|---|---|
| VL DNA | cagtctgtcgtgacgcagccgccctcagtgtctgcggccccaggacagaaggtcaccatctcctgctctg<br>gaagcagctccaacattgagaataattatgtatcatggtaccagcagctcccaggaacagccccccaaac<br>tcctcatttatgacaataataagcgaccctcagggattcctgaccgattctctggctccaagtctggcacgtc<br>agccaccctgggcatcaccggactccagactggggacgaggccgattattactgcggaacatgggata<br>gcagcctgagtgcctatgtcttcggaactgggaccaaggtcaccgtcctaggt<br>(SEQ ID NO: 50) |
| scFv | QSVVTQPPSVSAAPGQKVTISCSGSSSNIENNYVSWYQQLPGTAPKLLIYD<br>NNKRPSGIPDRFSGSKSGTSATLGITGLQTGDEADYYCGTWDSSLSAYVF<br>GTGTKVTVLGSRGGGGSGGGGSGGGGSLEMAQVQLQQWGAGLLKPSE<br>TLSLTCAVYGGSFSGYYWSWIRQSPGKGLEWIGEVNHSGNTNYNPSLKS<br>RVTISLDTSKNQFSLKLNSVTAADTAVYYCARYFPPMIDVWGQGTLVTVSS<br>(SEQ ID NO: 85) |
| DNA (5'-3') | cagtctgtcgtgacgcagccgccctcagtgtctgcggccccaggacagaaggtcaccatctcctgctctg<br>gaagcagctccaacattgagaataattatgtatcatggtaccagcagctcccaggaacagccccccaaac<br>tcctcatttatgacaataataagcgaccctcagggattcctgaccgattctctggctccaagtctggcacgtc<br>agccaccctgggcatcaccggactccagactggggacgaggccgattattactgcggaacatgggata<br>gcagcctgagtgcctatgtcttcggaactgggaccaaggtcaccgtcctaggtctagaggtggtggtgta<br>gcggcggcggcggctctggtggtggtggatcccaggtgcagctacagcagtggggcgcaggactgttg<br>aaaccttcggagaccctgtccctcacctgcgctgtctatggtgggtccttcagcggttactactggagctgg<br>atccgccagtcccagggaagggactggagtggattggggaagtcaatcatagtggcaacaccaacta<br>caacccgtccctcaagagtcgagtcaccatttcactagacacgtccaagaaccagttctccctgaaactg<br>aactctgtgaccgccgccgacacggccgtgtattactgtgcgcgctacttcccgccgatgatcgatgtttgg<br>ggtcaaggtactctggtgaccgtctcctca<br>(SEQ ID NO: 93) |

In one embodiment, the antigen binding protein is an anti-RAS antigen-binding protein or fragment thereof having an antigen binding region that comprises the amino acid sequence of SEQ ID NO: 86 and specifically binds to KLVVVGAVGV (SEQ ID NO: 111)/HLA2. In other embodiments, the anti-RAS antigen-binding protein is a scFv, or scFv-Fc fusion protein or full length human IgG with VH and VL regions or CDRs selected from Table 6.

TABLE 6

| | Ab #6 | | |
|---|---|---|---|
| CDRs: | 1 | 2 | 3 |
| VH | GGSISSSSYY<br>(SEQ ID NO. 51) | INHSGST<br>(SEQ ID NO. 52) | ARYSHHVDSGGYDV<br>(SEQ ID NO. 53) |
| VL | SSNIGNNY<br>(SEQ ID NO: 54) | DNN<br>(SEQ ID NO: 55) | GTWDSSLSAVV<br>(SEQ ID NO: 56) |
| Full VH | QLQLQESGPGLVKPSETLSLSCTVSGGSISSSSYYWGWIRQPPGKGLEWI<br>GEINHSGSTNYNPSLKSRVTISVDTSKNQFSLKLSSVTAADTAVYYCARYS<br>HHVDSGGYDVWGQGTLVTVSS<br>(SEQ ID NO: 57) | | |
| VH DNA | cagctgcagctgcaggagtcgggcccaggactggtgaagccttcggagaccctgtccctcagttgcact<br>gtctctggtggctccatcagcagtagtagttactactggggctggatccgccagcccccagggaagggc<br>tggagtggattggggaaatcaatcatagtggaagcaccaactacaacccgtccctcaagagtcgagtca<br>ccatatcagtagacacgtccaagaaccagttctccctgaagctgagttctgtgaccgccgcggacacggc<br>cgtgtattactgtgcgcgctactctcatcatgttgactctggtggttacgatgtttggggtcaaggtactctggtg<br>accgtctcctca<br>(SEQ ID NO: 58) | | |
| Full VL | QSVVTQPPSVSAAPGQKVTISCSGSSSNIGNNYVSWYQQLPRTAPRLLIYD<br>NNKRPSGIPDRFSASKSGTSATLGITGLQTGDEADYYCGTWDSSLSAVVF<br>GGGTKLTVLG<br>(SEQ ID NO: 59) | | |
| VL DNA | Cagtctgtcgtgacgcagccgccctcagtgtctgcggccccaggacagaaggtcaccatctcctgctctg<br>gaagcagctccaacattgggaataattatgtatcctggtaccagcagctcccaagaacagccccccagac<br>tcctcatttatgacaataataagcgaccctcagggattcctgaccgattctctgcctccaagtctggcacgtc<br>agccaccctgggcatcaccggactccagactggggacgaggccgattattactgcggaacatgggata<br>gcagcctgagtgctgtggtattcggcggagggaccaagctgaccgtcctaggt<br>(SEQ ID NO: 60) | | |
| scFv | QSVVTQPPSVSAAPGQKVTISCSGSSSNIGNNYVSWYQQLPRTAPRLLIYD<br>NNKRPSGIPDRFSASKSGTSATLGITGLQTGDEADYYCGTWDSSLSAVVF<br>GGGTKLTVLGSRGGGGSGGGGSGGGGSLEMAQLQLQESGPGLVKPSET<br>LSLSCTVSGGSISSSSYYWGWIRQPPGKGLEWIGEINHSGSTNYNPSLKSR<br>VTISVDTSKNQFSLKLSSVTAADTAVYYCARYSHHVDSGGYDVWGQGTLV<br>TVSS<br>(SEQ ID NO: 86) | | |

TABLE 6-continued

| DNA (5'-3') | gaagcagctccaacattgggaataattatgtatcctggtaccagcagctcccaagaacagcccccagac<br>tcctcatttatgacaataataagcgaccctcagggattcctgaccgattctctgcctccaagtctggcacgtc<br>agccaccctgggcatcaccggactccagactggggacgaggccgattattactgcggaacatgggata<br>gcagcctgagtgctgtggtattcggcggagggaccaagctgaccgtcctaggtctagaggtggtggtggt<br>agcggcggcggcggctctggtggtggtggatcccagctgcagctgcaggagtcgggcccaggactggt<br>gaagccttcggagaccctgtccctcagttgcactgtctctggtggctccatcagcagtagtagttactactgg<br>ggctggatccgccagcccccagggaaggggctggagtggattggggaaatcaatcatagtggaagca<br>ccaactacaacccgtccctcaagagtcgagtcaccatatcagtagacacgtccaagaaccagttctccct<br>gaagctgagttctgtgaccgccgcggacacggccgtgtattactgtgcgcgctactctcatcatgttgactct<br>ggtggttacgatgtttggggtcaaggtactctggtgaccgtctcctca<br>(SEQ ID NO: 94) |

In one embodiment, the antigen binding protein is an anti-RAS antigen-binding protein or fragment thereof having an antigen binding region that comprises the amino acid sequence of SEQ ID NO: 87 and specifically binds to KLVVVGAVGV (SEQ ID NO: 111)/HLA2. In other embodiments, the anti-RAS antigen-binding protein is a scFv, or scFv-Fc fusion protein or full length human IgG with VH and VL regions or CDRs selected from Table 7.

TABLE 7

| | | Ab #7 | | |
|---|---|---|---|---|
| CDRs: | | 1 | 2 | 3 |
| VH | | GGTFSSYG<br>(SEQ ID NO. 61) | IIPIFGTP<br>(SEQ ID NO. 62) | ARSYYGYFDG<br>(SEQ ID NO. 63) |
| VL | | QDISNY<br>(SEQ ID NO: 64) | DAS<br>(SEQ ID NO: 65) | QQYKSYPLT<br>(SEQ ID NO: 66) |
| Full VH | EVQLVESGAEVKEPGSSVKVSCKASGGTFSSYGISWIRQAPGQGLEWMG<br>EIIPIFGTPNYAQKFQGRVTITADESTSTAYVELSSLRSDDTAVYYCARSYY<br>GYFDGWGQGTLVTVSS<br>(SEQ ID NO: 67) | | | |
| VH DNA | gaggtgcagctggtggagtctggggctgaggtgaaggagcctgggtcctcggtgaaggtctcctgcaa<br>ggcttctggaggcaccttcagcagctatggtatcagctggattcgacaggcccctggacaagggcttga<br>gtggatgggagagatcatccctatctttggtacaccaaactacgcgcagaagttccagggcagagtcac<br>gattaccgcggacgaatccacgagcacagcctacgtggagctgagcagcctgagatctgacgacacg<br>gccgtatattactgtgcgcgctcttactacggttacttcgatggttggggtcaaggtactctggtgaccgtctc<br>ctca<br>(SEQ ID NO: 68) | | | |
| Full VL | DIQMTQSPSSLSASVGDRVTITCQASQDISNYLNWYQQKPGKAPKLLIYDA<br>SNLETGVPSRFSGSGSGTDFTFTISSLQPDDFATYYCQQYKSYPLTFGGG<br>TKVEIKR<br>(SEQ ID NO: 69) | | | |
| VL DNA | gacatccagatgacccagtctccatcctccctgtctgcatctgtaggagacagagtcaccatcacttgcca<br>ggcgagtcaggacattagcaactatttaaattggtatcagcagaaaccagggaaagcccctaagctcct<br>gatctacgatgcatccaatttggaaacaggggtcccatcaaggttcagtggaagtggatctgggacaga<br>ttttactttcaccatcagcagcctgcagcctgatgattttgcaacttattactgccaacagtataagagttacc<br>cgctcactttcggcggagggaccaaggtggagatcaaacgt<br>(SEQ ID NO: 70) | | | |
| scFv clone 45 | DIQMTQSPSSLSASVGDRVTITCQASQDISNYLNWYQQKPGKAPKLLIYDA<br>SNLETGVPSRFSGSGSGTDFTFTISSLQPDDFATYYCQQYKSYPLTFGGG<br>TKVEIKRSRGGGGSGGGGSGGGGSLEMAEVQLVESGAEVKEPGSSVKV<br>SCKASGGTFSSYGISWIRQAPGQGLEWMGEIIPIFGTPNYAQKFQGRVTIT<br>ADESTSTAYVELSSLRSDDTAVYYCARSYYGYFDGWGQGTLVTVSS<br>(SEQ ID NO: 87) | | | |
| DNA (5'-3') | gacatccagatgacccagtctccatcctccctgtctgcatctgtaggagacagagtcaccatcacttgcca<br>ggcgagtcaggacattagcaactatttaaattggtatcagcagaaaccagggaaagcccctaagctcct<br>gatctacgatgcatccaatttggaaacaggggtcccatcaaggttcagtggaagtggatctgggacaga<br>ttttactttcaccatcagcagcctgcagcctgatgattttgcaacttattactgccaacagtataagagttacc<br>cgctcactttcggcggagggaccaaggtggagatcaaacgtctagaggtggtggtggtagcggcggc<br>ggcggctctggtggtggtggatccgaggtgcagctggtggagtctggggctgaggtgaaggagcctgg<br>gtcctcggtgaaggtctcctgcaaggcttctggaggcaccttcagcagctatggtatcagctggattcgac<br>aggcccctggacaagggcttgagtggatgggagagatcatccctatctttggtacaccaaactacgcgc<br>agaagttccagggcagagtcacgattaccgcggacgaatccacgagcacagcctacgtggagctga<br>gcagcctgagatctgacgacacggccgtatattactgtgcgcgctcttactacggttacttcgatggtggg<br>gtcaaggtactctggtgaccgtctcctca<br>(SEQ ID NO: 95) | | | |

In one embodiment, the antigen binding protein is an anti-RAS antigen-binding protein or fragment thereof having an antigen binding region that comprises the amino acid sequence of SEQ ID NO: 88 and specifically binds to KLVVVGAVGV (SEQ ID NO: 111)/HLA2. In other embodiments, the anti-RAS antigen-binding protein is a scFv, or scFv-Fc fusion protein or full length human IgG with VH and VL regions or CDRs selected from Table 8.

comprise an antigen-binding region or portion having an amino acid sequence that is 96-99.9% identical to the amino acid sequences disclosed in Tables 1-8 above. In still other embodiments, the antigen-binding proteins of the disclosure may comprise an antigen-binding region or portion having an amino acid sequence that is about 70%, 80%, 90%, or 95.9% identical to one of the sequences disclosed in Tables 1-8 above.

TABLE 8

| | Ab #8 | | |
|---|---|---|---|
| CDRs: | 1 | 2 | 3 |
| VH | GYTFTSYY (SEQ ID NO. 71) | INPSGGST (SEQ ID NO. 72) | ARSMYQYFLDS (SEQ ID NO. 73) |
| VL | SSNIGAGYD (SEQ ID NO: 74) | GNI (SEQ ID NO: 75) | QSYDSNLSG (SEQ ID NO. 76) |

| | |
|---|---|
| Full VH | EVQLVESGAEVKKPGASVKISCKASGYTFTSYYMHWVRQAPGQGLEWMG<br>IINPSGGSTSYAQKFQGRVTMTRDTSTSTVYMELSSLRSEDTAVYYCARS<br>MYQYFLDSWGQGTLVTVSS<br>(SEQ ID NO: 77) |
| VH DNA | gaggtgcagctggtggagtccggggctgaggtgaagaagcctggggcctcagtaaaaatttcctgcaag<br>gcatctggatacaccttcaccagctactatatgcactgggtgcgacaggcccctggacaagggcttgagt<br>ggatgggaataatcaaccctagtggtggtagcacaagctacgcacagaagttccagggcagagtcacc<br>atgaccagggacacgtccacgagcacagtctacatggagctgagcagcctgagatctgaggacacgg<br>ccgtatattactgtgcgcgctctatgtaccagtacttcctggattcttggggtcaaggtactctggtgaccgtct<br>cctca<br>(SEQ ID NO: 78) |
| Full VL | QSVVTQPPSVSGAPGQRVTISCTGSSSNIGAGYDVHWYQQLPGTAPKLLI<br>YGNINRPSGVPDRFSGSKSGTSASLAITGLQAEDEADYYCQSYDSNLSGY<br>VFATGTKVTVLG<br>(SEQ ID NO: 79) |
| VL DNA | cagtctgtcgtgacgcagccgccctcagtgtctggggccccagggcagagggtcaccatctcctgcactg<br>ggagcagctccaacatcggggcaggttatgatgtacactggtaccagcaacttccaggaacagcsccc<br>aaactcctcatctatggtaacatcaatcggccctcaggggtccctgaccgattctctggctccaagtctggc<br>acctcagcctccctggccatcactgggctccaggctgaggatgaggctgattattactgccagtcctatgac<br>agcaacctgagtggttatgtcttcgcaactgggaccaaggtcaccgtcctaggt<br>(SEQ ID NO: 80) |
| scFv | QSVVTQPPSVSGAPGQRVTISCTGSSSNIGAGYDVHWYQQLPGTAPKLLI<br>YGNINRPSGVPDRFSGSKSGTSASLAITGLQAEDEADYYCQSYDSNLSGY<br>VFATGTKVTVLGSRGGGGSGGGGSGGGGSLEMAEVQLVESGAEVKKPG<br>ASVKISCKASGYTFTSYYMHWVRQAPGQGLEWMGIINPSGGSTSYAQKFQ<br>GRVTMTRDTSTSTVYMELSSLRSEDTAVYYCARSMYQYFLDSWGQGTLV<br>TVSS<br>(SEQ ID NO: 88) |
| DNA (5'-3') | cagtctgtcgtgacgcagccgccctcagtgtctggggccccagggcagagggtcaccatctcctgcactg<br>ggagcagctccaacatcggggcaggttatgatgtacactggtaccagcaacttccaggaacagcsccc<br>aaactcctcatctatggtaacatcaatcggccctcaggggtccctgaccgattctctggctccaagtctggc<br>acctcagcctccctggccatcactgggctccaggctgaggatgaggctgattattactgccagtcctatgac<br>agcaacctgagtggttatgtcttcgcaactgggaccaaggtcaccgtcctaggtctagagggtggtggtggt<br>agcggcggcggcggctctggtggtggtggatccgagtgcagctggtggagtccggggctgaggtgaa<br>gaagcctggggcctcagtaaaaatttcctgcaaggcatctggatacaccttcaccagctactatatgcact<br>gggtgcgacaggcccctggacaagggcttgagtggatgggaataatcaaccctagtggtggtagcaca<br>agctacgcacagaagttccagggcagagtcaccatgaccagggacacgtccacgagcacagtctaca<br>tggagctgagcagcctgagatctgaggacacggccgtatattactgtgcgcgctctatgtaccagtacttcc<br>tggattcttggggtcaaggtactctggtgaccgtctcctca<br>(SEQ ID NO: 96) |

In some embodiments, antigen binding proteins of the disclosure comprise an antigen-binding region or portion having an amino acid sequence that is 100% identical to the amino acid sequences disclosed in Tables 1-8 above. In other embodiments, antigen binding proteins of the disclosure In one embodiment, the antigen binding protein is an anti-RAS antibody having an hIgG1 constant region, a human light chain (kappa) or human light chain (lambda) as shown in Table 9.

TABLE 9

| | |
|---|---|
| Human heavy chain constant region and IgG1 Fc domain sequence | ASTKGPSVFPLAPSSKSTSGGTAALGCLVKDYFPEPVTVSWNSGAL
TSGVHTFPAVLQSSGLYSLSSVVTVPSSSLGTQTYICNVNHKPSNTK
VDKKVEPKSCDKTHTCPPCPAPELLGGPSVFLFPPKPKDTLMISRTP
EVTCVVVDVSHEDPEVKFNWYVDGVEVHNAKTKPREEQYNSTYRV
VSVLTVLHQDWLNGKEYKCKVSNKALPAPIEKTISKAKGQPREPQV
YTLPPSREEMTKNQVSLTCLVKGFYPSDIAVEWESNGQPENNYKTT
PPVLDSDGSFFLYSKLTVDKSRWQQGNVFSCSVMHEALHNHYTQK
SLSLSPGK*
(SEQ ID NO: 97) |
| DNA sequence | gtctcctcagcttccaccaagggcccatcggtcttccccctggcaccctcctccaagagcacctc
tggggcacagcggccctgggctgcctggtcaaggactacttccccgaaccggtgacggtgtc
gtggaactcaggcgccctgaccagcggcgtgcacaccttcccggctgtcctacagtcctcagg
actctactccctcagcagcgtggtgaccgtgccctccagcagcttgggcacccagacctacatc
tgcaacgtgaatcacaagcccagcaacaccaaggtggacaagaaagttgagcccaaatctt
gtgacaaaactcacacatgcccaccgtgcccagcacctgaactcctggggggaccgtcagtct
tcctcttccccccaaaacccaaggacaccctcatgatctcccggacccctgaggtcacatgcgt
ggtggtggacgtgagccacgaagaccctgaggtcaagttcaactggtacgtggacggcgtgg
aggtgcataatgccaagacaaagccgcgggaggagcagtacaacagcacgtaccgtgtggt
cagcgtcctcaccgtcctgcaccaggactggctgaatggcaaggagtacaagtgcaaggtctc
caacaaagccctcccagcccccatcgagaaaaccatctccaaagccaaagggcagccccg
agaaccacaggtgtacaccctgcccccatcccgggaggagatgaccaagaaccaggtcag
cctgacctgcctggtcaaaggcttctatcccagcgacatcgccgtggagtgggagagcaatgg
gcagccggagaacaactacaagaccacgcctcccgtgctggactccgacggctccttcttcct
ctacagcaagctcaccgtggacaagagcaggtggcagcaggggaacgtcttctcatgctccgt
gatgcatgaggctctgcacaaccactacacgcagaagagcctctccctgtctccgggtaaatg
a
(SEQ ID NO: 98) |
| Human light chain (kappa) | TVAAPSVFIFPPSDEQLKSGTASVVCLLNNFYPREAKVQWKVDNAL
QSGNSQESVTEQDSKDSTYSLSSTLTLSKADYEKHKVYACEVTHQ
GLSSPVTKSFNRGEC*(SEQ ID NO: 99) |
| DNA sequence | accgtggccgctccctccgtgttcatcttcccaccttccgacgagcagctgaagtccggcaccgc
ttctgtcgtgtgcctgctgaacaacttctaccccgcgaggccaaggtgcagtggaaggtggac
aacgccctgcagagcggcaactcccaggaatccgtgaccgagcaggactccaaggacagc
acctactccctgtcctccaccctgaccctgtccaaggccgactacgagaagcacaaggtgtac
gcctgcgaagtgacccaccagggcctgtctagcccgtgaccaagtctttcaaccggggcgag
tgctag
(SEQ ID NO: 100) |
| Human light chain (lambda) | QPKANPTVTLFPPSSEELQANKATLVCLISDFYPGAVTVAWKADGS
PVKAGVETTKPSKQSNNKYAASSYLSLTPEQWKSHRSYSCQVTHE
GSTVEKTVAPTECS*
(SEQ ID NO: 101) |
| DNA sequence | cagcctaaggccaaccctaccgtgaccctgttcccccatcctccgaggaactgcaggccaac
aaggccaccctcgtgtgcctgatctccgactttctaccctggcgccgtgaccgtggcctggaagg
ctgatggatctcctgtgaaggccggcgtggaaaccaccaagccctccaagcagtccaacaac
aaatacgccgcctcctcctacctgtccctgaccctgagcagtggaagtccaccggtcctaca
gctgccaagtgacccacgagggctccaccgtggaaaagaccgtggctcctaccgagtgctcct
ag
(SEQ ID NO: 102) |

In one embodiment, the antigen binding protein is an anti-RAS bispecific T-cell engaging antibody or BiTE having a Ras antibody light chain variable region, a first linker, and a Ras antibody heavy chain variable region. In certain embodiments, the BiTE antibody further comprises a second linker and an anti-CD3 scFv-His tag having sequences as shown in Table 10. Linkers used in generating BiTEs are generally glycine-rich and range in length from about 4 to 25 amino acids.

In some embodiments, a BiTE antibody of the present disclosure has an amino acid sequence that is 70%, 80%, 90%, 95% and in some cases, 99-100% identical to SEQ ID NO: 103.

TABLE 10

| | |
|---|---|
| BiTE Antibody | QSVLTQPPSVSGAPGQRVTISCTGSSSNIGAGYDVHWYQQLPGTAP
KLLIYGNSNRPSGVPDRFSGSKSGTSASLAITGLQAEDEADYYCQSY
DSSLSGSVFGTGTKVTVLGSRGGGSGGGGSGGGGSLEMAQVQLV
QSGAEVKKPGSSVKVSCKASGGTFSSYTINWVRQAPGQGLEWMGG
FIPISGTVNYAQKFQGRVTITADESTSTAYMELSSLRSEDTAVYYCAR
PLDWTEDIWGQGTLVTVSSGGGGSDVQLVQSGAEVKKPGASVKVSC
KASGYTFTRYTMHWVRQAPGQGLEWIGYINPSRGYTNYADSVKGRF
TITTDKSTSTAYMELSSLRSEDTATYYCARYYDDHYCLDYWGQGTTV
TVSSGEGTSTGSGGSGGSGGADDIVLTQSPATLSLSPGERATLSCRA
SQSVSYMNWYQQKPGKAPKRWIYDTSKVASGVPARFSGSGSGTDY
SLTINSLEAEDAATYYCQQWSSNPLTFGGGTKVEIKHHHHHH*
(SEQ ID NO: 103) |

TABLE 10-continued

```
Ras antibody      QSVLTQPPSVSGAPGQRVTISCTGSSSNIGAGYDVHWYQQLPGTAP
light chain       KLLIYGNSNRPSGVPDRFSGSKSGTSASLAITGLQAEDEADYYCQSY
variable          DSSLSGSVFGTGTKVTVLG
region            (SEQ ID NO: 19)

Linker 1          SRGGGGSGGGGSGGGGSLEMA
                  (SEQ ID NO: 104)

Linker 1          ctagaggtggtggtggtagcggcggcggcggctctggtggtggtggatcc
DNA               (SEQ ID NO: 105)

Ras antibody      QVQLVQSGAEVKKPGSSVKVSCKASGGTFSSYTINWVRQAPGQGLE
heavy chain       WMGGFIPISGTVNYAQKFQGRVTITADESTSTAYMELSSLRSEDTAVY
variable          YCARPLDWTEDIWGQGTLVTVSS
region            (SEQ ID NO: 17)

Linker 2          GGGGS
DNA               (SEQ ID NO: 106)

DNA               ggcggggaggatcc
                  (SEQ ID NO: 107)

AntiCD3           DVQLVQSGAEVKKPGASVKVSCKASGYTFTRYTMHWVRQAPGQGL
scFv-his tag      EWIGYINPSRGYTNYADSVKGRFTITTDKSTSTAYMELSSLRSEDTAT
                  YYCARYYDDHYCLDYWGQGTTVTVSSGEGTSTGSGGSGGSGGADD
                  IVLTQSPATLSLSPGERATLSCRASQSVSYMNWYQQKPGKAPKRWIY
                  DTSKVASGVPARFSGSGSGTDYSLTINSLEAEDAATYYCQQWSSNPL
                  TFGGGTKVEIKHHHHHH*
                  (SEQ ID NO: 108)

DNA               gacgtgcagctggtgcagagcggagctgaagtgaagaaacctggcgcctccgtgaaggtgtcct
                  gcaaagctagcggctataccttcacccggtacaccatgcactgggtgcgccaggcacctggaca
                  gggactggaatggatcggctacatcaaccctcccgggctacaccaactacgccgactctgtg
                  aagggccggttcaccatcaccaccgataagtccaccagcaccgcttacatggaactgtcctccct
                  gagatccgaggacaccgctacctactattgcgcccggtactacgacgaccactactgcctggact
                  actggggacagggaaccacagtgaccgtgtcctctggcgagggcacctctactggatctggggg
                  aagtggtggttctggcggcgctgacgacatcgtgctgacccagtctccagccaccctgtctctgag
                  cccaggcgagagagctaccctgtcctgcagagcctcccagtccgtgtcctacatgaattggtatca
                  gcagaagcctggcaaggcccctaagcggtggatctacgacacctccaaggtggcctctggcgtg
                  ccagcccggttttccggatctggctctggcaccgactactccctgaccatcaacagcctggaagcc
                  gaggacgctgccacctattactgccagcagtggtcctccaaccccctgacctttggaggcggcac
                  caaggtggaaatcaagcaccaccatcatcaccactga
                  (SEQ ID NO: 109)
```

EXAMPLES

Example 1

Epitope Selection and Peptide Synthesis

For purposes of the present disclosure, K-Ras peptides are identified by amino acid position(s) relative to NCBI Reference Sequence NP_203524.1 of the NCBI protein database. Accordingly, the K-Ras peptides, LVVVGAGGV (SEQ ID NO: 115) and KLVVVGAGGV (SEQ ID NO: 110) correspond to amino acids 6-14 and 5-14, respectively, of the reference sequence.

In order to select HLA-A2-restricted epitopes derived from Ras codon 12-mutations with strong immunogenicity, the prediction scores of Ras mutation sequences were first screened using three online available databases (BIMAS, RANKPEP and SYFPEITHI). (Ras mutation sequences are described in Smith et al. *Oncogenic mutations in ras create HLA-A2.1 binding peptides but affect their extracellular antigen processing. International Immunology* Vol. 9(8), pp. 1085-1093, 1997).

Based on the predicted binding scores from all three databases, the following peptides were selected for testing to determine if the peptides were able to elicit epitope-specific T cell responses in HLA-A2-positive healthy donors.

TABLE 11

| | SEQUENCE | | |
|---|---|---|---|
| RAS10-WT | KLVVVGAGGV | SEQ ID NO: | 110 |
| RAS10-G12V | KLVVVGAVGV | SEQ ID NO: | 111 |
| RAS10-G12C | KLVVVGACGV | SEQ ID NO: | 112 |
| RAS10-G12D | KLVVVGADGV | SEQ ID NO: | 113 |
| RAS10-G12S | KLVVVGASGV | SEQ ID NO: | 114 |
| RAS9-WT | LVVVGAGGV | SEQ ID NO: | 115 |
| RAS9-G12V | LVVVGAVGV | SEQ ID NO: | 116 |
| RAS9-G12C | LVVVGACGV | SEQ ID NO: | 117 |
| RAS9-G12D | LVVVGADGV | SEQ ID NO: | 118 |

All peptides were purchased and synthesized by Genemed Synthesis, Inc. (San Antonio, Tex.). Peptides were sterile with purity of 70% to 90%. The peptides were dissolved in DMSO and diluted in saline at 5 mg/mL and stored at −80° C.

A human scFv antibody phage display library (10×10$^{10}$ clones) constructed by Eureka Therapeutics was used for the selection of human mAbs specific to K-Ras G12V/HLA-A0201. In order to reduce the conformational change of MHC1 complex introduced by immobilizing the protein complex onto plastic surfaces, solution panning and cell panning were used in place of conventional plate panning. In solution panning, biotinylated antigens were first mixed with the human scFv phage library after extended washing with PBS buffer, and then antiben-scFv antibody phage complexes were pulled down by streptavidin-conjugated Dyna beads M-280 through a magnetic rack. The bound clones were then eluted and use to infect E. coli XL1-Blue. In cell panning, T2 cells loaded with Ras 10-G12V or Ras 9-G12V peptides were first mixed with the human scFv phage library. T2 cell is a TAP-deficient, HLA-A0201+ lymphoblast cell line. To load peptide, T2 cells were pulsed with peptides (50 µg/ml) in serum free RPM!1640 medium, in the presence of 20 µg/ml β2 microglobulin overnight. After extended washing with PBS, peptide-loaded T2 cells with bound scFv antibody phage were spun down. The bound clones were then eluted and used to infect E. Coli XL1-Blue. The phage clones expressed in bacteria were then purified. The panning were performed for 3-4 rounds with either solution panning, cell panning or a combination of solution and cell panning to enrich scFv phage clones that specifically bind to Ras10-G12V and/or Ras9-G12V/HLA-0201.

Table 12 is the summary of phage panning against K-Ras G12V/HLA-A0201. Eight independent pannings were carried out. Through FACS analysis, 122 positive clones were identified out of 436 clones screened. Out of 80 sequenced positive clones, 8 unique clones were found.

TABLE 12

| | Beads solution panning | Cell panning | BBC panning | Total |
|---|---|---|---|---|
| Number of clones screened | 62 | 312 | 62 | 436 |
| Number of ELISA positive | 4 | 93 | 25 | 122 |
| Number sequenced | 4 | 54 | 22 | 80 |
| Number of unique clones | 2 | 3 | 3 | 8 |

Example 2

T2 Stabilization Assay

The immunogenicity of MHC class I-restricted peptides requires the capacity to bind and stabilize MHC class I molecules on the live cell surface. Moreover, the computer prediction has only up to 70% accuracy; so the next step was to seek a direct measurement of the strength of the interaction between the peptides and the HLA-A0201 molecules using a conventional binding and stabilization assay that uses antigen-transporting-deficient (TAP2 negative) HLA-A0201 human T2 cells. T2 cells lack TAP function and consequently are defective in properly loading class I molecules with antigenic peptides generated in the cytosol. The association of exogenously added peptides with thermolabile, empty HLA-A0201 molecules stabilizes them and results in an increase in the level of surface HLA-A0201 recognizable by a specific anti-HLA-A0201 mAb such as BB7.2.

Figure 1C:
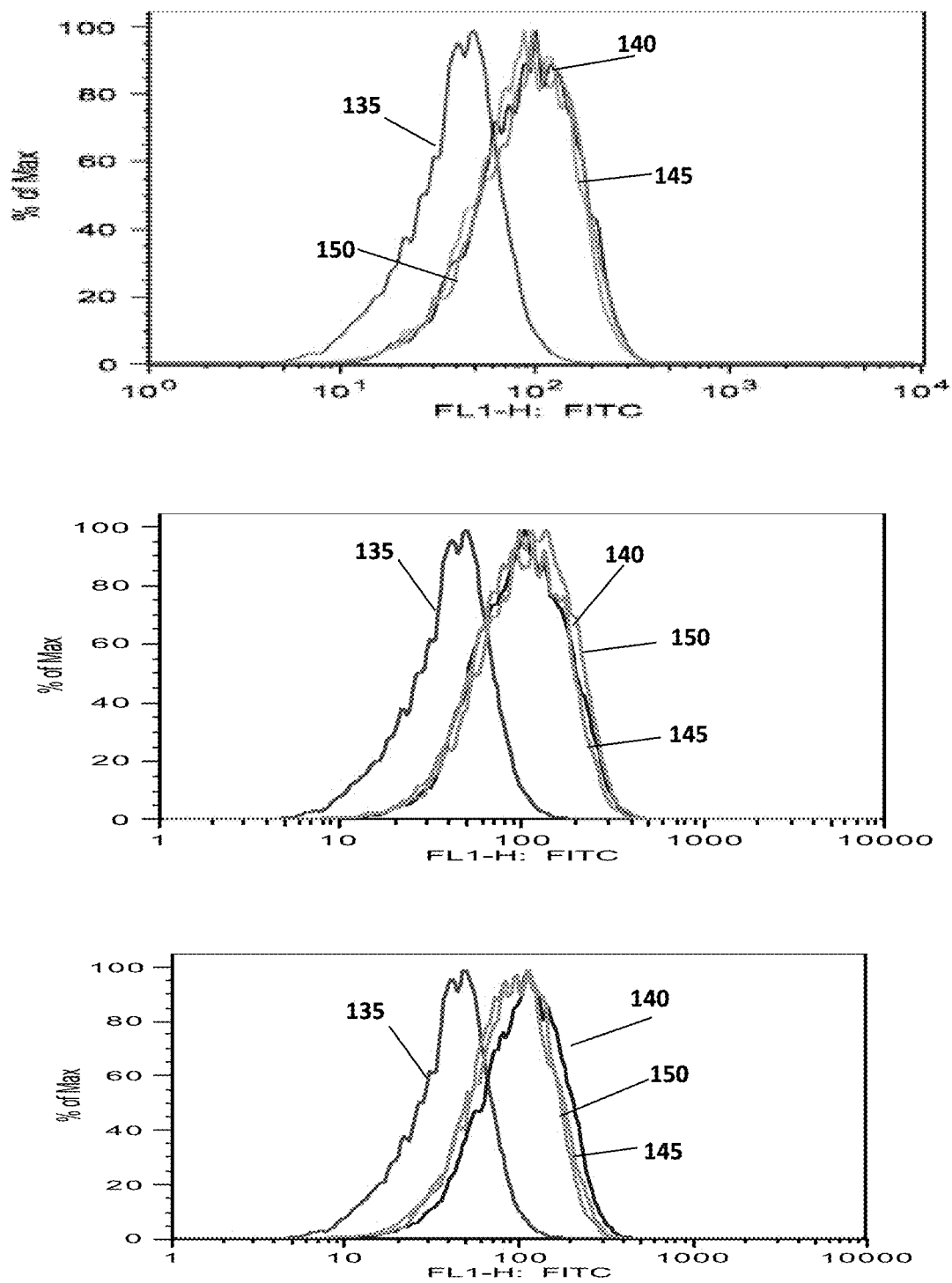
Figure 1D:
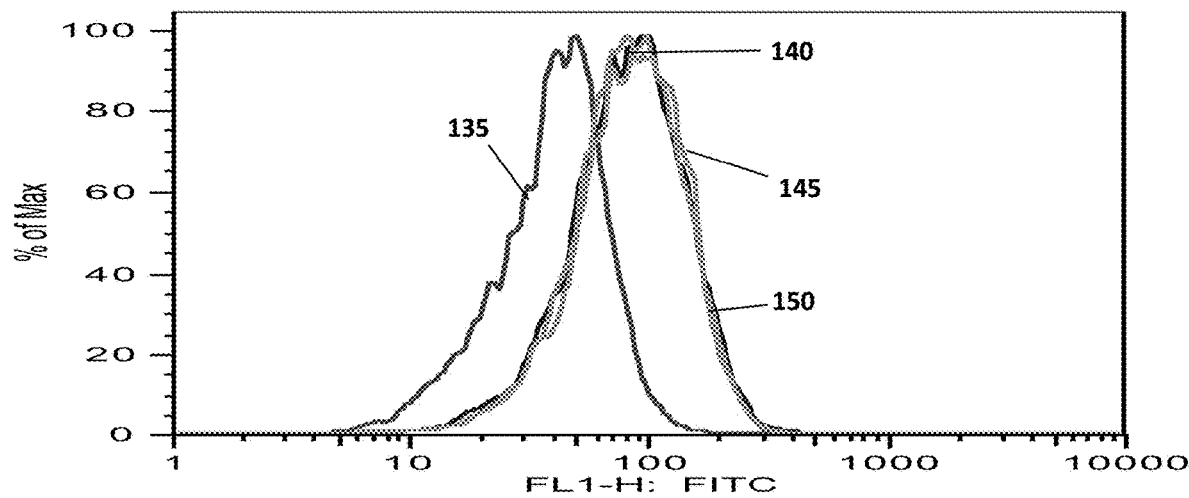
Figure 1D:
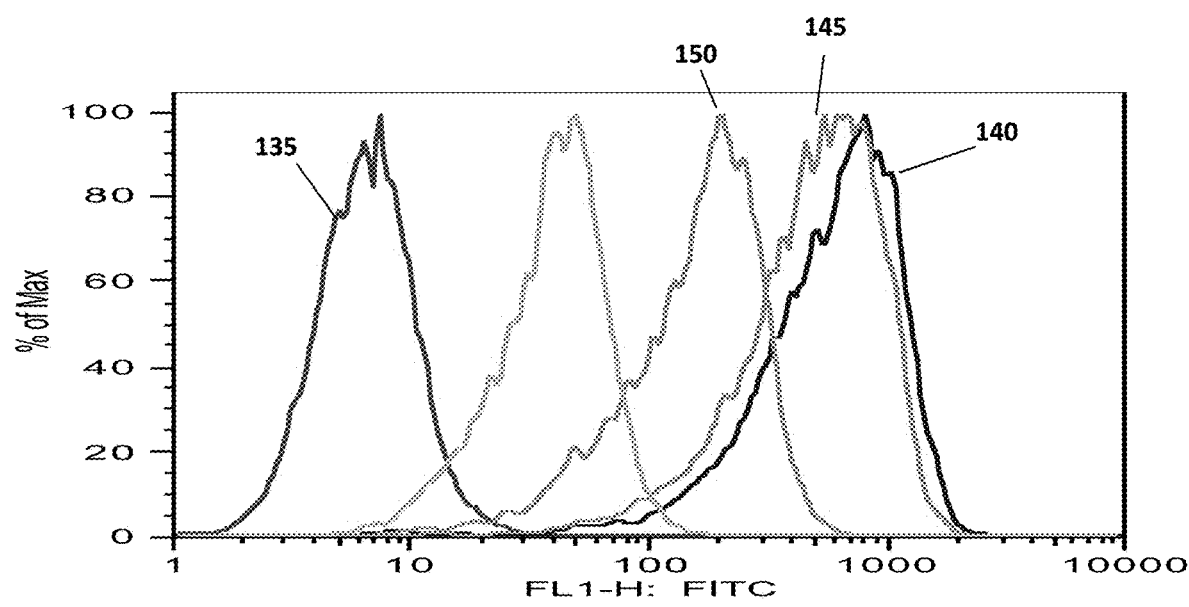

The T2 binding assay showed that Ras 10-mer peptides wild type (WT), G12V, G12C, G12D increased the HLA-A2 expression on T2 cells, when used at 50 µg/ml (FIGS. 1A and B) and the best peptide to stabilize HLA-A2 expression was RasG12V, followed by RasG12D, and to a lower extent with RasG12-C and wild type. Ras 9-mer peptides showed better HLA-A2 stabilizations at all concentrations used, but no significant difference was shown among the peptides (FIGS. 1C and D).

Example 3

Mutant Ras Peptide-Induced T Cell Responses

After informed consent on Memorial Sloan-Kettering Cancer Center Institutional Review Board approved protocols, peripheral blood mononuclear cells (PBMCs) from HLA-typed healthy donors were obtained by Ficoll density centrifugation. T cell stimulation followed the protocol described previously (Dao T. et al. *Identification of a human cyclin D1-derived peptide that induces human cytotoxic CD4 cells*. Plos One Vol. 4(9) e6730, 2009). Peptide-specific T cell responses were measured by IFN-g ELISPOT assay (Dao, T, Science Tr Med 2013).

Figure 2A:
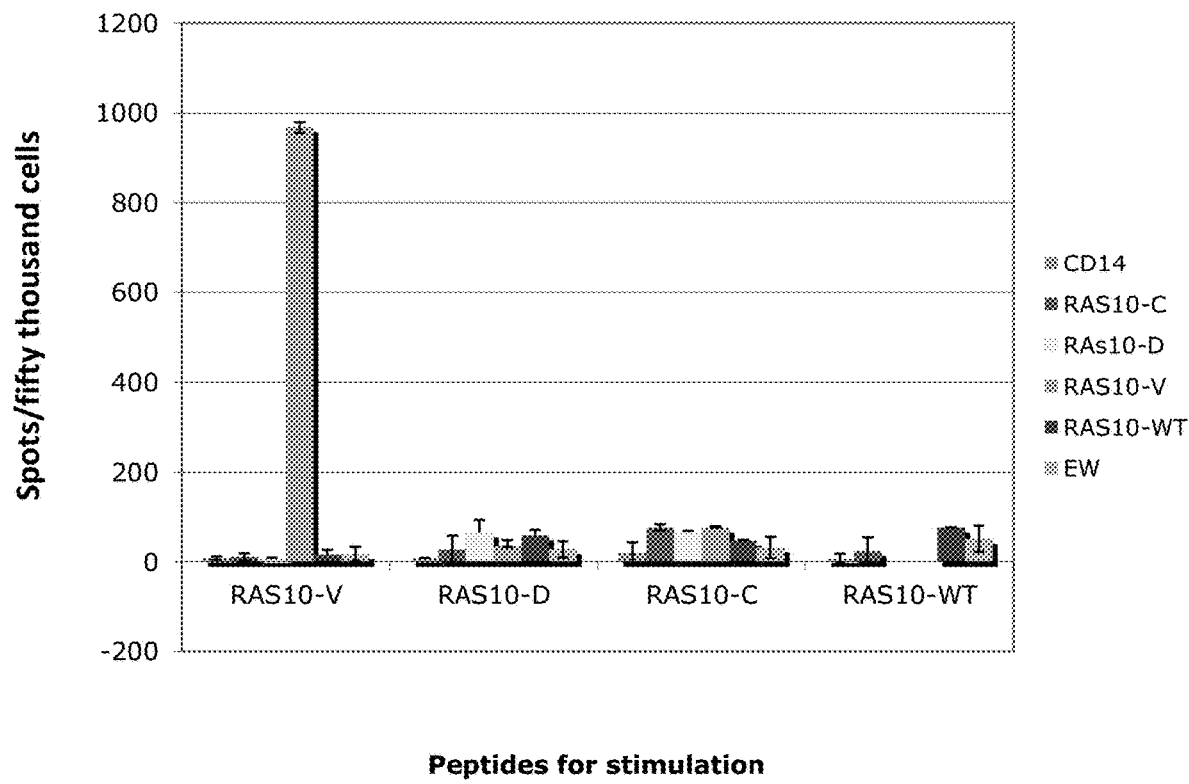
FIGS. 2A and 2B show RAS-G12 mutant peptide induced-T cell response. T cells from healthy HLA-A0201 positive donors were stimulated with RAS10 peptides WT, G12V, G12C or G12D (shown on X axis) for 5 rounds (A). Similarly, T cells were stimulated with RAS9 peptides G12V, G12C or G12D for 3 (B upper) or 5 (B lower) rounds. The peptide-specific T cell response was measured by IFN-g ELISPOT assay when challenged with the individual peptides or controls shown in legends on right.
Figure 2B:
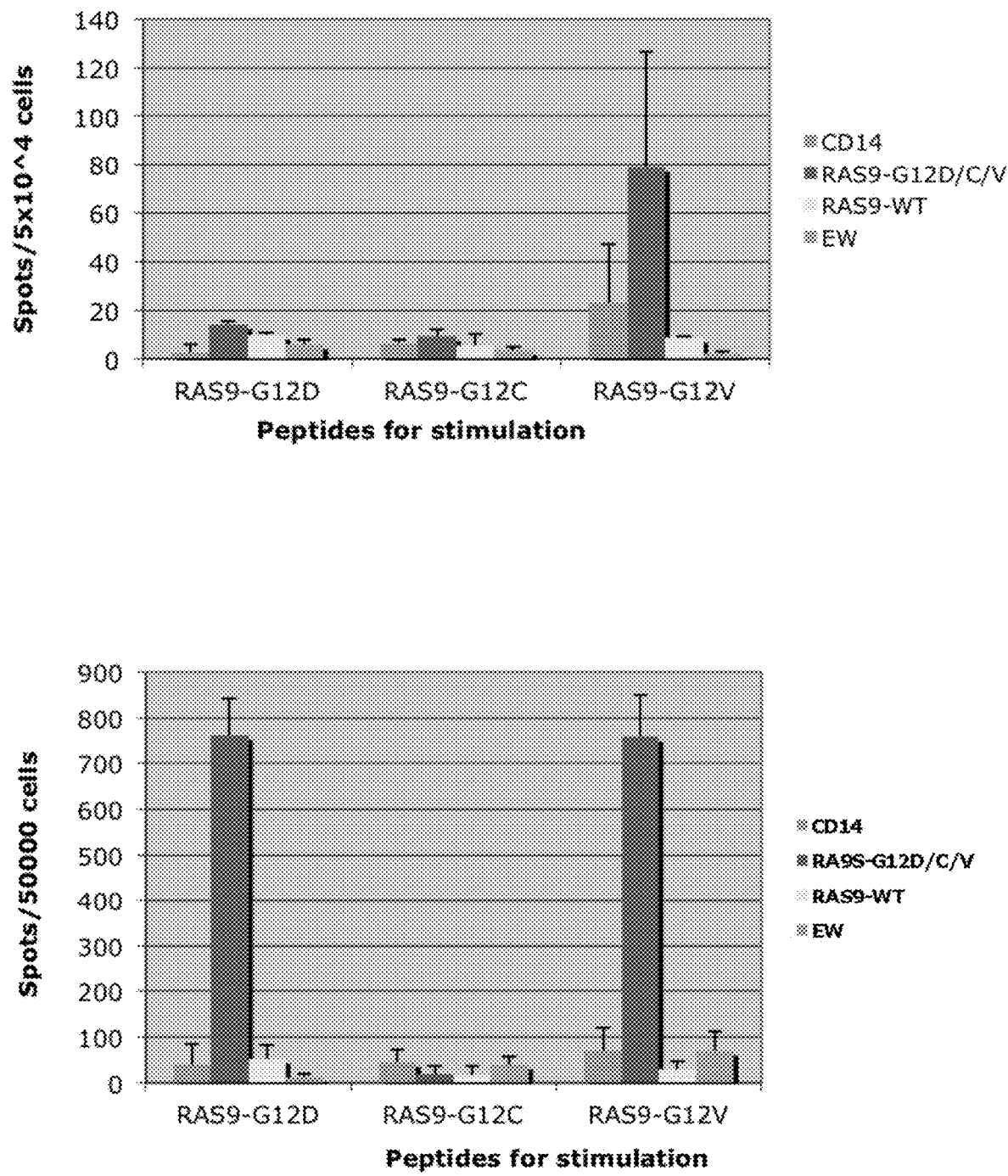

To expand the peptide-specific T cell precursors, three to five in vitro stimulations were performed and the specific T cell response was measured by IFN-g production, when challenged with individual peptide. Ras-G12V peptide stimulation induced strong T cell response against Ras10-G12V but showed no cross-reactivity to the peptides Ras10-WT, G12C and G12D (FIG. 2A). Similarly, Ras 9-G12V also induced strong T cell response to itself, but not other peptides. Five stimulations of T cells enhanced the response and showed more IFN-g spots. Interestingly, Ras 9-G12D peptide also induced peptide-specific response to itself after 5 rounds of stimulation (FIG. 2B).

Based on T cell data, TCR-like mAbs specific for the Ras10-G12V and WT peptides in the context of HLA-A0201 molecule were generated.

Example 4

Biotinylated Peptide/HLA-A0201 Complex

Figure 8:
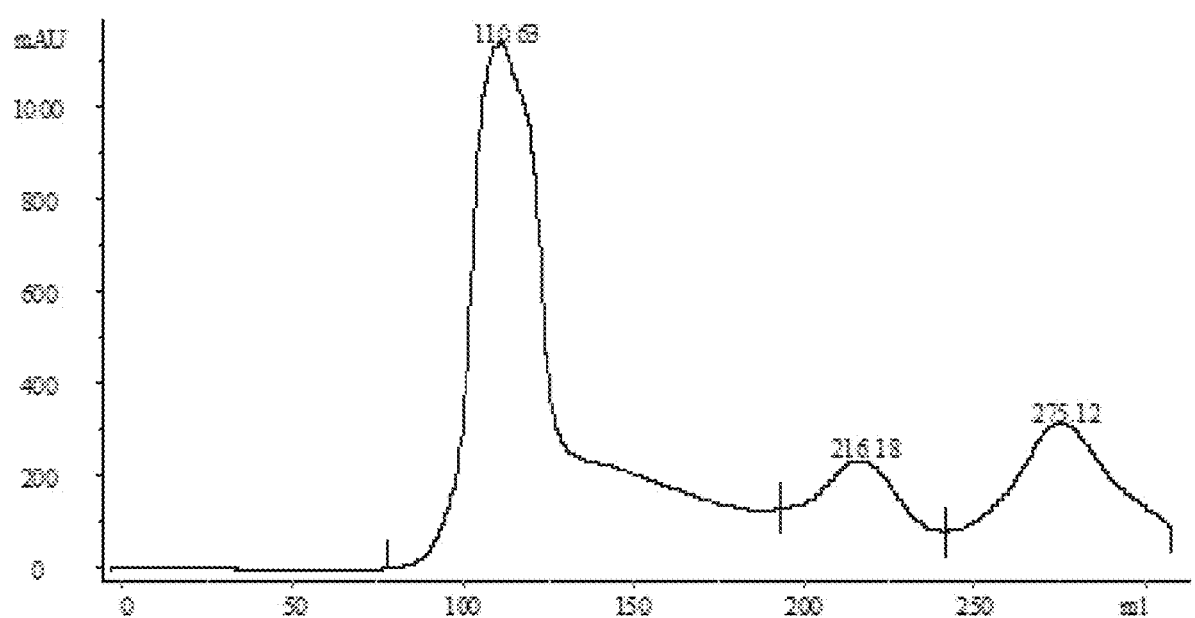
FIG. 8 shows the elution profile of peptide/HLA-A0201 complex. The unpurified sample was loaded and eluted for 1 column volume. The first peak, consisting of misfolded aggregates, eluted at approximately 110.63 mL after loading. The peak corresponding to the properly folded MHC complex was observed at 216.18 mL. Lastly, the peak consisting of free B2M was observed at 275.12 mL.
Figure 9:
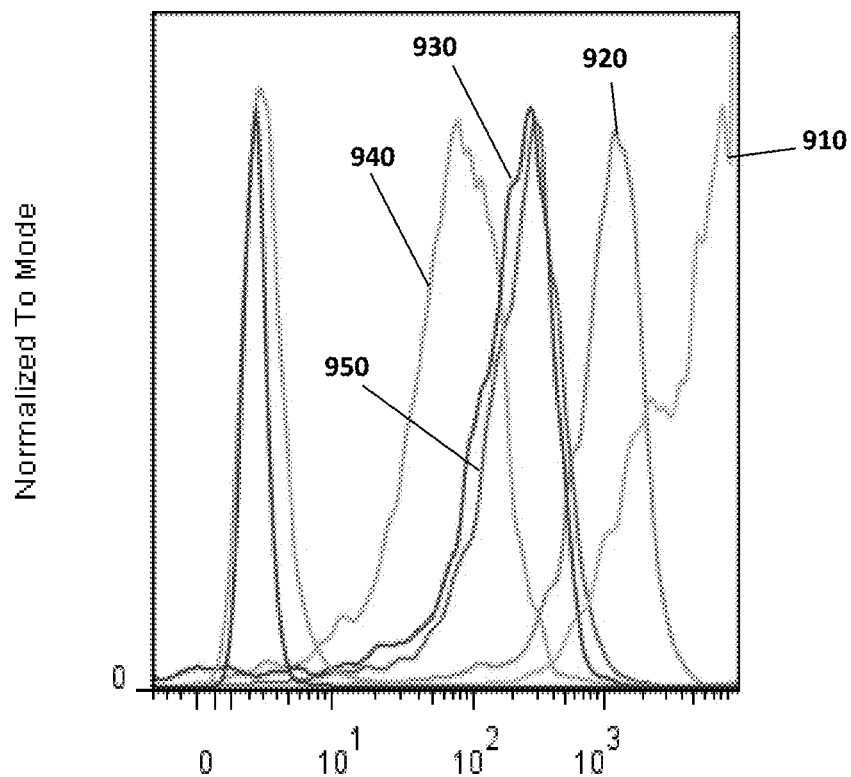
FIG. 9 shows the results of Ras phage antibody clones FACS binding assay. Clone #2 binds to K-Ras10 G12V (T2-014A2mut, 910) and K-Ras9 G12V/HLAA0201 (T2-014A1mut, 920) specifically, while doesn't recognize empty T2 cells (T2-B2M, 930), or K-Ras WT peptide/HLA A0201 complexes (T2-0142WT, 940 and T2-0141WT, 950).

Biotinylated peptide/HLA-A0201 complex monomers were prepared according to standard protocols (John D. Altman and Mark M. Davis Current Protocols in Immunology (2003) 17.3.1-17.3.33). In brief, DNA of full-length human β2m was synthesized by Genewiz and cloned into vector pET-27b. The BirA substrate peptide (BSP) was added to the C-terminus of HLA A0201 extracellular domain (ECD). DNA of HLA-A0201 ECD-BSP was synthesized by Genewiz and cloned into vector pET-27b. The vectors expressing human β2m and HLA-A0201 ECD-BSP were transformed into *E. Coli* BL21 separately, and isolated as inclusion bodies from bacterial culture. Peptide ligands Ras10-G12V and Ras10-WT were refolded with human β2m and HLA A0201 ECD-BSP to form Ras-G12V/HLA A0201 and Ras10-VVT/HLA A0201 complex monomers. Folded peptide/HLA A0201 monomers were concentrated by ultrafiltration and further purified through size-exclusion chromatography (FIG. 8). HiPrep 26/60 Sephacryl S-300 HR was equilibrated with Hyclone Dulbecco's Phosphate Buffered Saline solution (Thermo Scientific, Cat No. SH3002802) for 1.5 column volumes. The unpurified sample was loaded and eluted for 1 column volume. The first peak, consisting of misfolded aggregates, eluted at approximately 110.63 mL after loading. The peak corresponding to the properly folded MHC complex was observed at 216.18 mL. Lastly, the peak consisting of free B2M was observed at 275.12 mL.

Purified peptide/HLA A0201 monomers were visualized through SDS-PAGE (figure E-2). In brief, 4 µg of the protein was mixed with 2.5 μL of the NuPAGE LDS Sample Buffer (Life Technologies, NP0008) and filled up to 10 μL with deionized water. The sample was heated at 70° C. for 10 minutes, and then loaded onto the gel. Gel electrophoresis was performed at 180V for 1 hour. Two major bands were observed on the gel. The 30 KD band was HLA A0201, and the 10 KD band was B2M.

Peptide/HLA A0201 monomers were biotinylated via BirA-mediated enzymatic reaction and subsequently purified by high-resolution anion-exchange chromatography. Biotinylated peptide/HLA A0201 monomers were stored in PBS at −80° C.

Example 5

Screening of Phage ScFv Specific for K-Ras G12V/HLA-A0201 Complex

Positive phage clones were determined by flow cytometry using Ras G12V bound live T2 cells. In brief, the cells were first stained with purified scFv phage clones, and followed by staining with a mouse anti-M13 mAb, and finally the R-PE conjugated horse anti-mouse IgG from Vector Labs. Each step of the staining was done between 30-60 minutes on ice and the cells were washed twice between each step of the staining. FIG. 8 is an example of K-Ras G12V/HLA A0201 specific phage clone binding to peptide-loaded T2 cells. Clone #2 binds to K-Ras10 G12V (T2-014A2mut, light green line) and K-Ras9 G12V/HLA A0201(T2-014A1mut, blue line) specifically, while doesn't recognize empty T2 cells (T2-B2M, dark green line), or K-Ras WT peptide/HLA A0201 complexes (T2-0142WT, orange line and T2-0141WT, red line).

Example 6

Engineering Full Length mAb Using the Selected scFv Fragments

Full-length human IgG1 of the selected phage clones were produced in HEK293 and Chinese hamster ovary (CHO) cell lines, as described (Tomimatsu K, Matsumoto S, Yamashita M, Teruya K, Katakura Y, Kabayama S & Shirahat S. Production of human monoclonal antibodies against FceRla by a method combining in vitro immunization with phage display. Biosci Biotechnol Biochem 2009; 73 (7) 1465-1469). In brief, antibody variable regions were subcloned into mammalian expression vectors, with matching human lambda or kappa light chain constant region and human IgG1 constant region sequences. Molecular weight of the purified full length IgG antibodies were measured under both reducing and non-reducing conditions by electrophoresis. Examples of electrophoresis (SDS-PAGE) are shown in figure E-4. Lane 1, clone #2, reducing condition, lane 2, clone #4, reducing condition, lane 3, clone #7, reducing condition, lane 6-7, non-reducing condition, clone #2, #4 and #7, respectively.

Example 7

Engineering Bispecific T Cell Engager (T-BiTE)

The BiTE antibodies are single-chain bispecific antibodies comprising K-Ras G12V/HLA A0201 specific antibodies in the scFv format, at the N-terminal end and an anti-human CD3ε scFv mouse monoclonal antibody at the C-terminal end (Brischwein, K. et al. MT110: A novel bispecific single-chain antibody construct with high efficacy in eradicating established tumors. Molecular Immunology 43, 1129-1143 (2006)). The DNA fragments coding for the Ras scFv antibody and the anti-human CD3ε scFv antibody were synthesized by Genewiz and subcloned into Eureka's mammalian expression vector pGSN-Hyg using standard DNA technology. A hexhistamine tag is inserted downstream of the Ras BiTE antibodies at the C-terminal end for antibody purification and detection. Chinese hamster ovary (CHO) cells were transfected with the Ras BiTEs expression vector and stable expression was achieved by standard drug selection with methionine sulfoximine (MSX), a glutamine synthetase (GS)-based method (reference 2). CHO cell supernatants containing secreted Ras BiTE molecules were collected. Ras BiTE was purified using HisTrap HP column (GE healthcare) by FPLC AKTA system. Briefly, CHO cell culture was clarified and loaded to the column with low imidazole concentration (20 mM), and then an isocratic high imidazole concentration elution buffer (500 mM) was used to elute the bound Ras BiTE proteins. Molecular weight of the purified Ras BiTEs antibodies were measured under non-reducing conditions by electrophoresis (figure E-5). Lane 1-4, reducing condition, clone #2, #4,901 control hIgG1 antibody and #7, respectively.

Example 8

Characterization of Full-Length Human IgG1 Specific for Ras 10-G12V/HLA-A0201 Complex To determine whether mAb clones #2, 4 and 7 bind to cell surface peptide/HLA-A0201 complexes on live cells, flow cytometry was used to study HLA-A0201 positive, TAP-deficient T2 cells loaded with peptides. T2 cells were incubated with the peptides (50 μg/ml) and β2 microglobulin (β2M) at 10 μg/ml in a serum-free medium over night, and the cells were harvested and washed. The cells were stained with mAbs or isotype control human IgG1, for 30 minutes and washed, followed by staining with a secondary goat (Fab)$_2$ anti-human IgG1 mAb conjugated to FITC. The mAbs were also conjugated to an allophycocyanin (APC) fluorophore to perform direct staining.

Figure 3A:
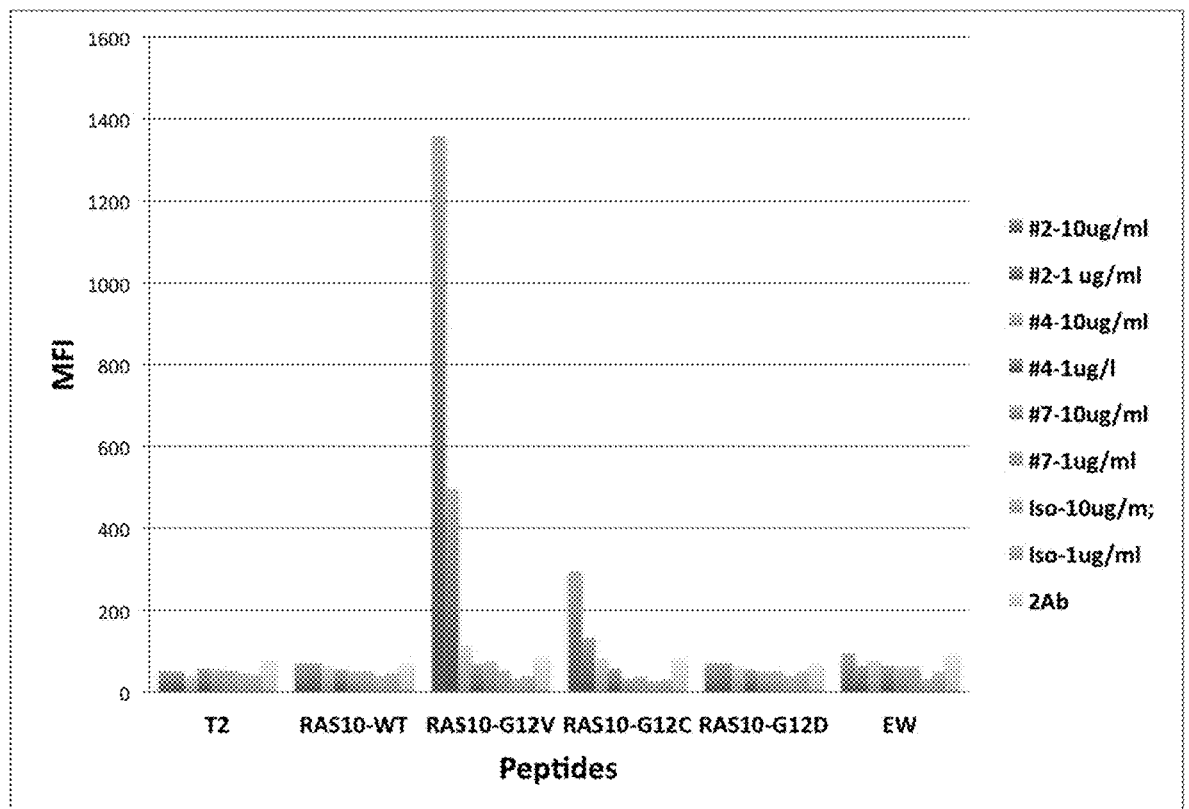
FIGS. 3A-G show the binding of mAbs to RAS10-G12V peptide/HLA A2 complex. RAS 10-WT, RAS10-G12V, G12-C or G12D peptides were pulsed onto T2 cells at 50 µg/ml, (see FIG. 1 above). The binding of the mAb to the peptide/HLA-A2 complex was measured by direct staining with mAbs conjugated to APC or by indirect staining with mAbs, followed by secondary goat anti-human IgG1/FITC mAb. The binding of the mAbs was measured by flow cytometry on a FACScalibur (Becton Dickenson) and analyzed with FlowJo 9.6.3 software. Simultaneously, the cells were stained with anti-HLA-A2 mAb, BB7.2, to measure the ability of the peptides to stabilize HLA-A2 molecule on the cell surface. (A) binding of the mAbs #2, 4 or 7 and isotype control on T2 cells pulsed with indicated peptides by indirect staining. (B) Direct staining with APC-conjugated mAbs, including BB7 and isotype control antibody. (C) Binding of the mAbs #2, 4 or 7 on T2 cells pulsed with alanine-substituted peptides at various positions as indicated. In this case alanine was substituted for the WT amino acid at the position indicated (positions #9-13 of the peptide) to probe the site of antibody binding. (D) Binding of the mAb #2 to RAS10-G12S or RAS10-A11G peptide at 10 or 1 µg/ml by indirect staining including BB7 and isotype control antibody. (E) Binding of the mAb #2 to various RAS10-G12-derived mutant peptides and CT and MTH peptides, in indirect staining. In this case alanine was substituted for the WT amino acid at the position indicated (positions #8-13 of the peptide) to probe the site of antibody binding. (F) Antibody by the above peptides to T2 cells was measured. In this case alanine was substituted for the WT amino acid at the position indicated #8-13 of the peptide) to confirm binding to HLA molecules. (G) T2 stabilization by the Ras 10 peptides was simultaneously measured by staining T2 cells with BB7 mAb. In this case alanine was substituted for the WT amino acid at the position indicated (positions #8-13 of the peptide) to confirm binding to HLA molecules. Isotype controls showed no binding at all and therefore were not shown.

FIG. 3A showed that mAb #2 specifically bound to T2 cells pulsed with Ras10-G12V peptide and also to a lesser degree to Ras-G12C peptide, but not to Ras WT, Ras10-G12D or T2 alone, or control HLA-A0201-binding peptide EW (Dao, T. et al., *Identification of a human cyclin D1-derived peptide that induces human cytotoxic CD4 cells*. Plos One vol. 4(9) e6730, 2009. MAb #4 and 7 did not show significant binding to T2 pulsed with those Ras10 peptides.

Figure 3B:
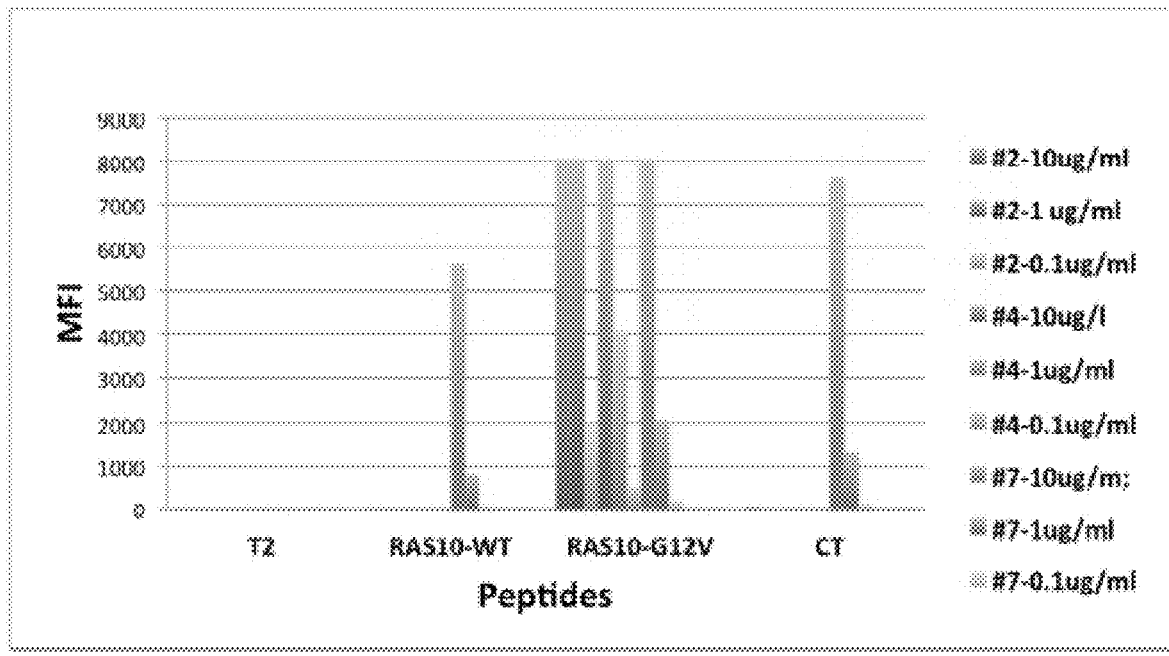
Figure 3B:
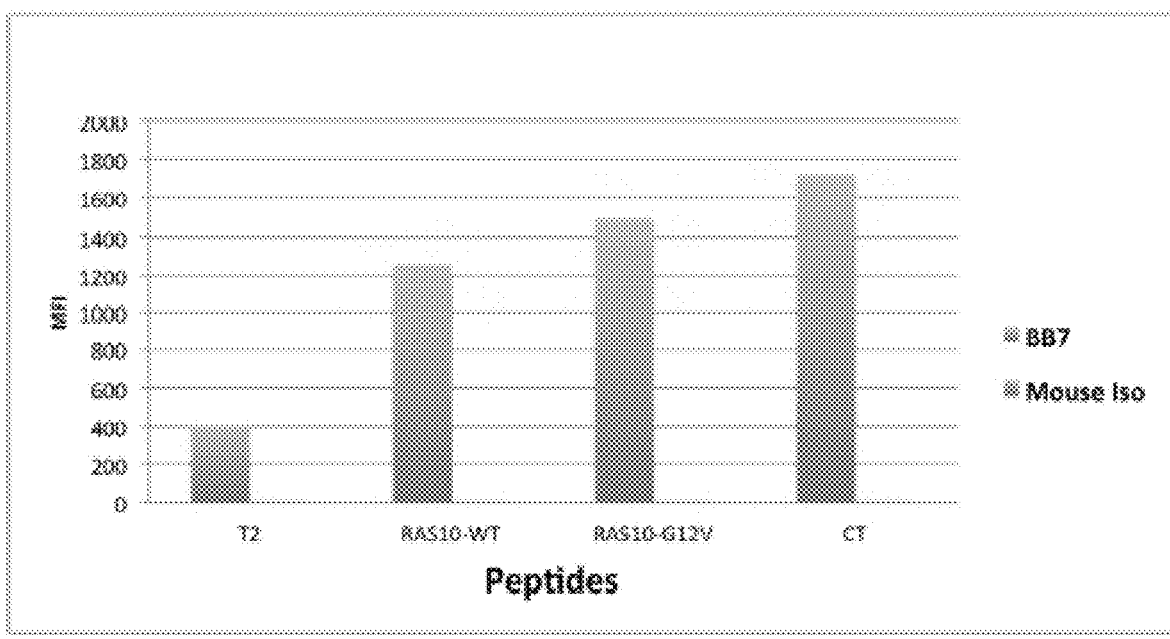

The results were confirmed by measuring the binding by APC-conjugated mAbs in direct staining. Since APC conjugation greatly amplified the binding signal, #7 mAb was seen binding to T2 cells pulsed with Ras10-G12V and also to Ras10-WT peptide, to a lesser degree. However, mAb titration showed that mAb #2 has the strongest affinity for the Ras10-G12V/HLA-A0201 complex. In this experiment, the binding of the mAbs to a potentially cross-reactive normal peptide CT (not from Ras) was also tested. Only mAb #7 bound to it, as well as Ras WT, demonstrating that mAb #7 is a more promiscuous mAb than #2 or #4 (FIG. 3B upper). The binding specificity was not due to differences in the peptide binding to HLA-A2 molecule, as HLA-A2 expression level by peptide CT was similar to other peptides used in the same condition (lower panel).

Binding Affinity of Ras Human IgG1 mAbs

The binding affinity of Ras hIgG1 mAbs towards peptide-loaded MHC complex were determined using ForteBio Octet QK. Data are shown in Table 13. 5 µg/mL of biotinylated Ras peptide/HLA-A0201 complex was loaded onto the Streptavidin biosensor. The excess antigen was washed off first. The Ras mAbs were then individually tested at 10 µg/mL for association and dissociation steps. Binding parameters were calculated using 1:1 binding site model, partial fit. Ras antibody #2 and #4 specifically recognize Ras G12V mutant peptide/HLA-A0201 complex, while Ras antibody #7 recognize both mutant and wild type Ras peptide in the context of HLA-A0201 molecule.

TABLE 13

Binding affinity measurement of Ras hIgG1 antibodies

| Protein | Antigen | $k_d$ [1/s] | Error in $k_d$ | $k_a$ [1/Ms] | $k_D$ [nM] |
|---|---|---|---|---|---|
| #2 | Ras G12V/HLA-A0201 | 7.17E−4 | 1.42E−4 | 8.07E4 | 8.88 |
| #4 | Ras G12V/HLA-A0201 | 3.63E−3 | 5.11E−5 | 3.96E5 | 9.19 |
| #7 | Ras G12V/HLA-A0201 | 7.46E−4 | 8.11E−5 | 8.50E4 | 8.77 |
| #2 | Ras wt/HLA-A0201 | — | — | — | — |
| #4 | Ras wt/HLA-A0201 | — | — | — | — |
| #7 | Ras wt/HLA-A0201 | 1.53E−3 | 3.35E−5 | 2.34E4 | 65.1 |

Example 9

Peptide Epitope Mapping

Figure 3C:
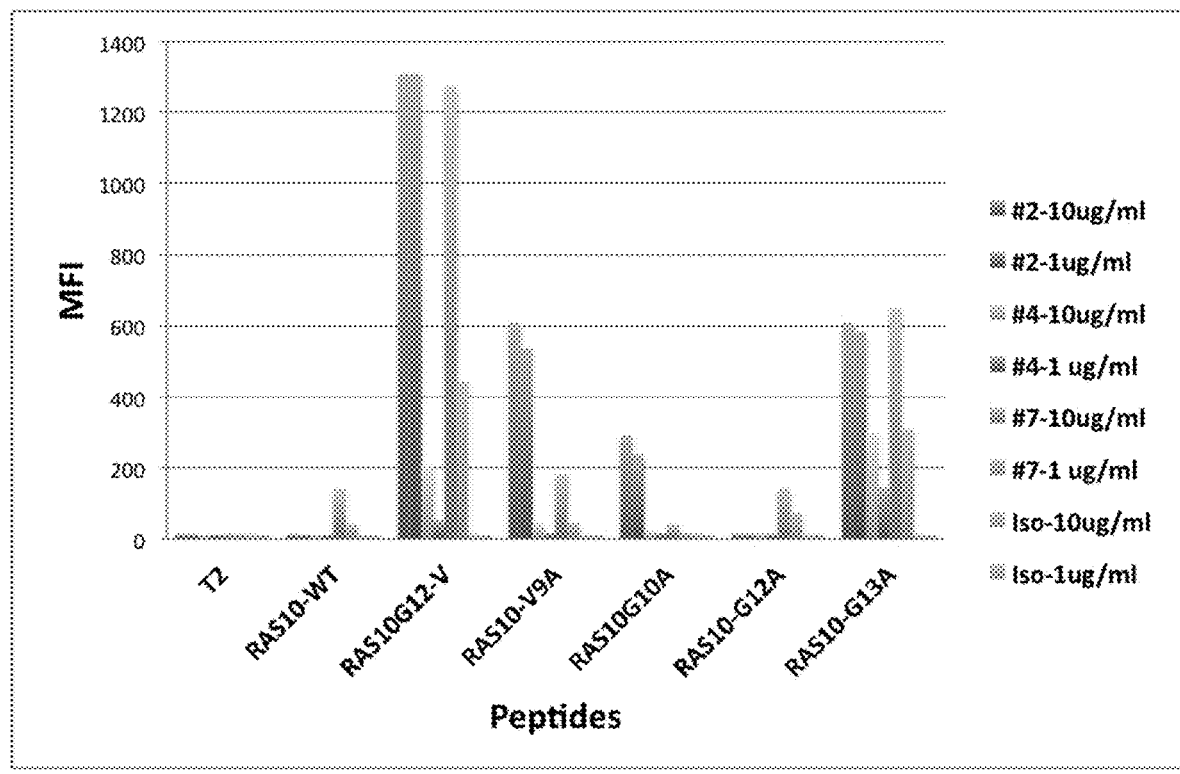
Figure 3D:
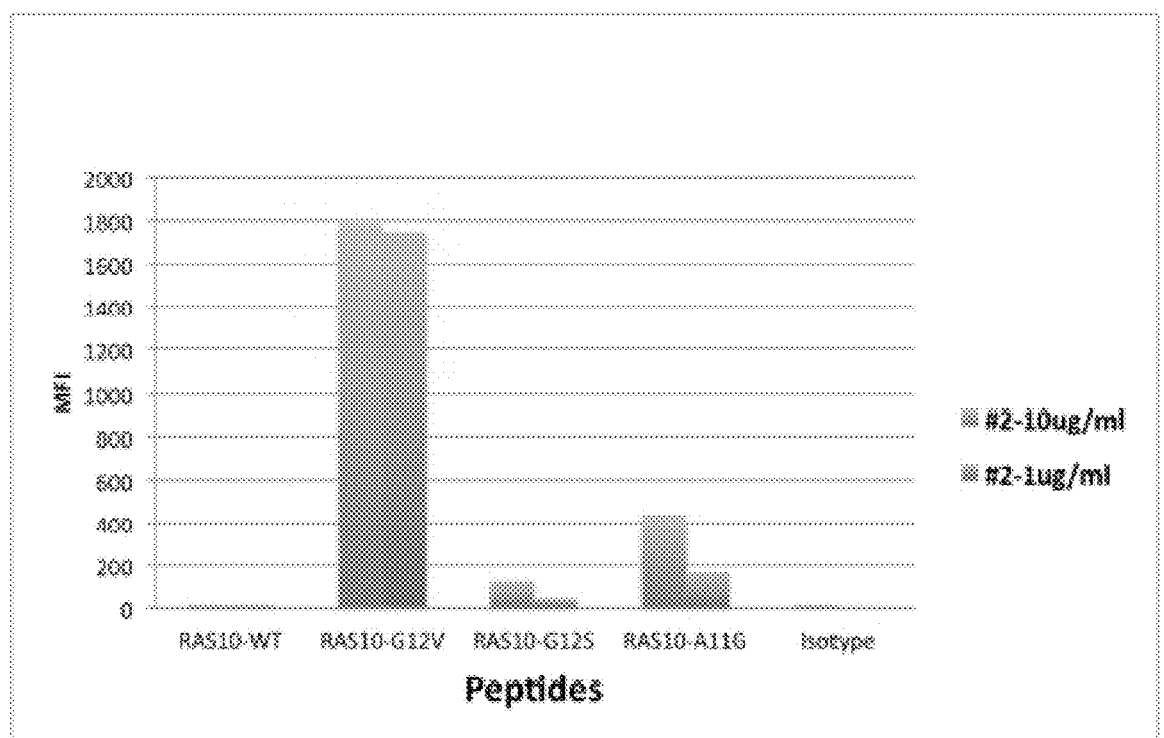
Figure 3D:
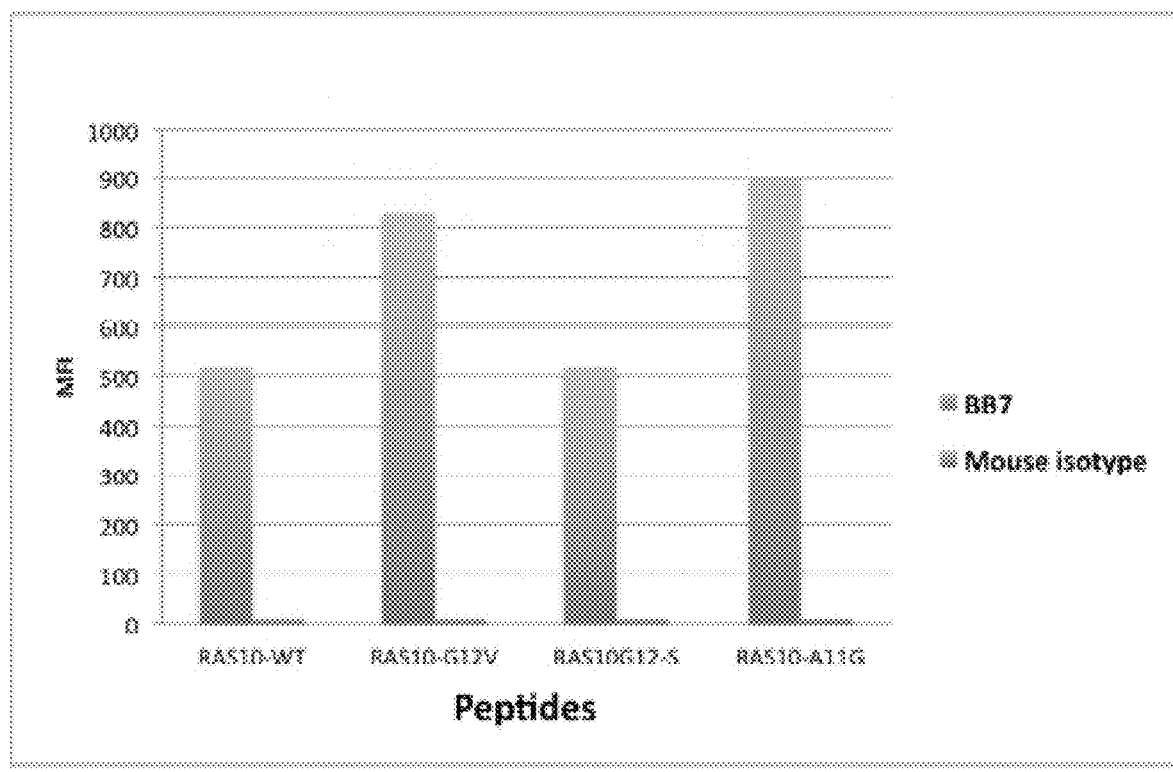
Figure 3E:
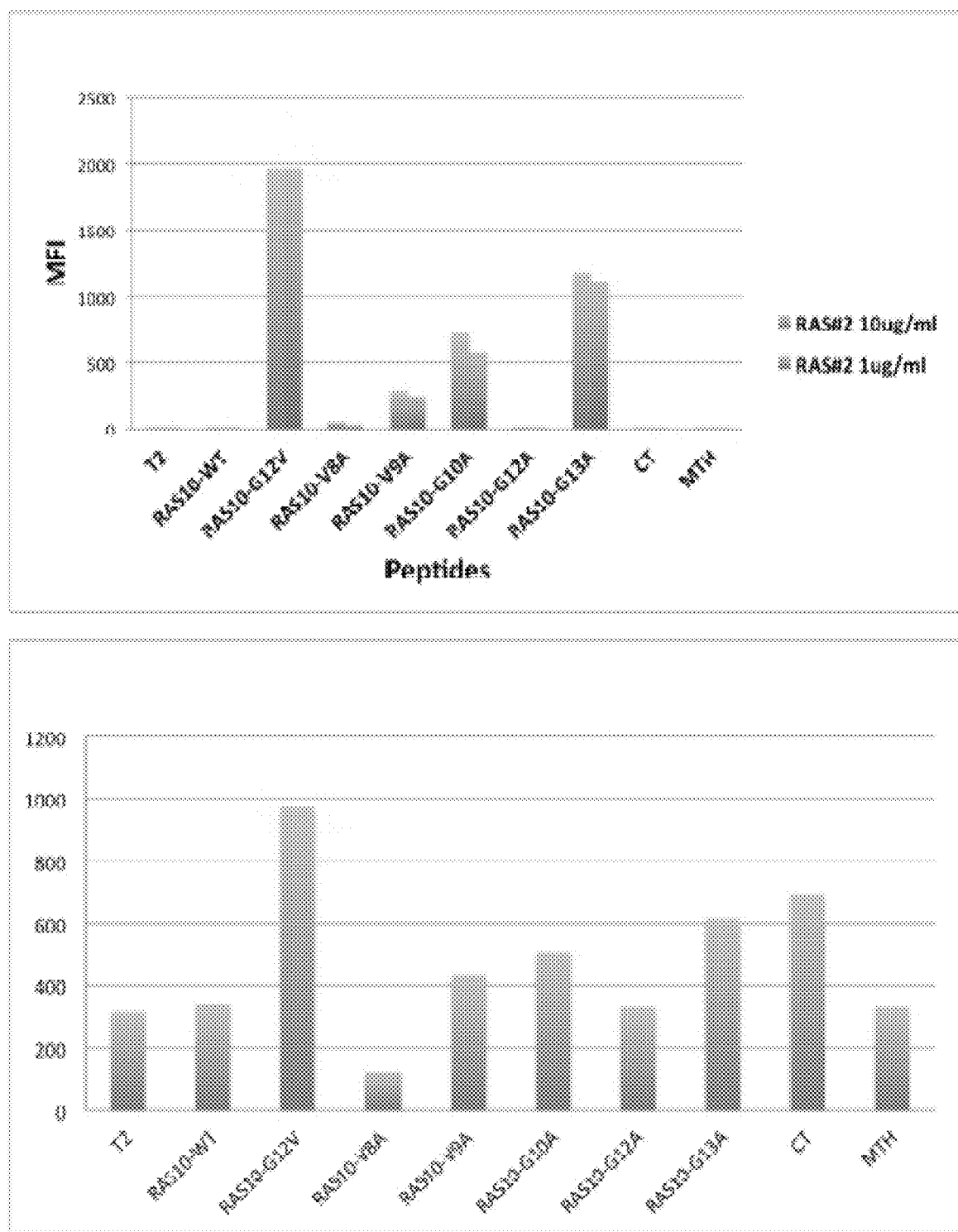
Figure 3F:
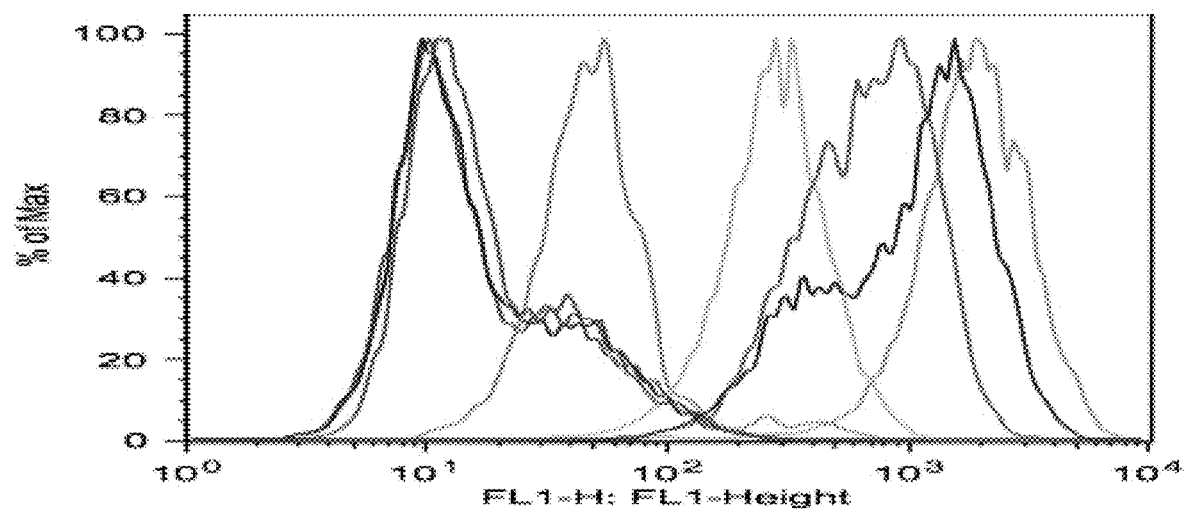
Figure 3F:
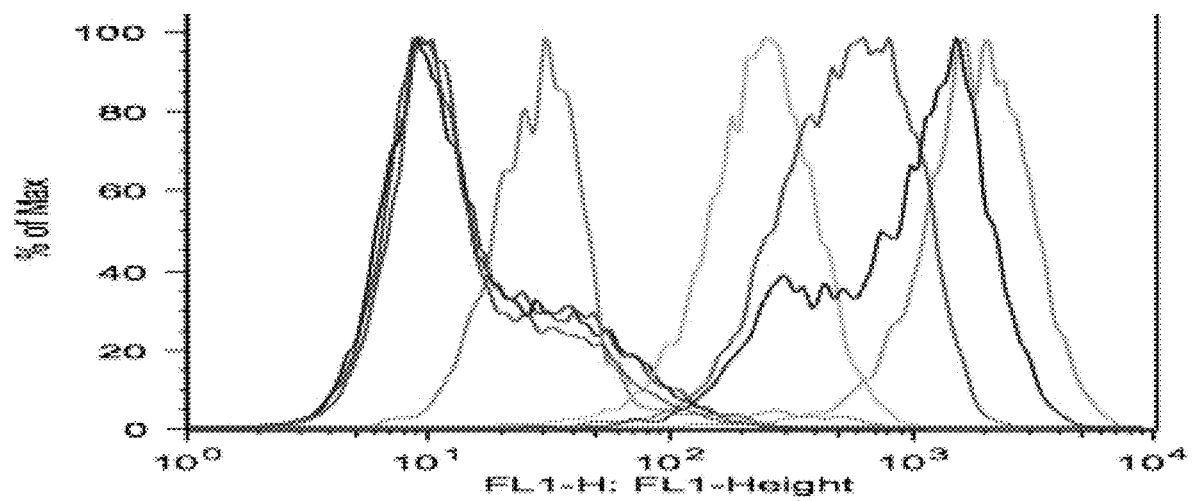
Figure 3G:
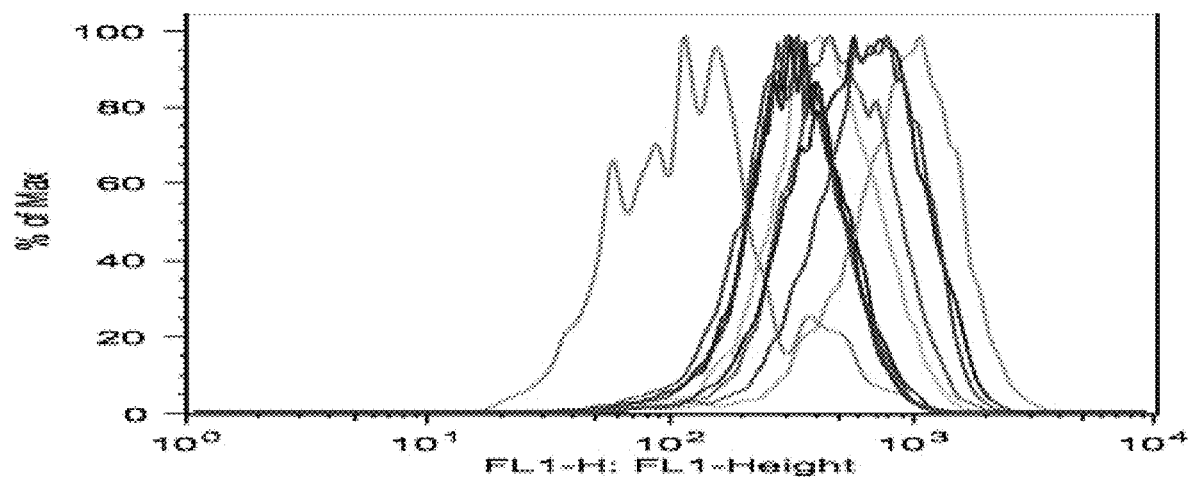

To investigate with more precision the epitope for mAb recognition, Ras10-G12V peptides were substituted with alanine at Ras protein positions 8, 9, 10, 12, and 13 and pulsed onto T2 cells and were tested for mAb binding. Alanine substitution at position 12 completely abrogated the binding of #2 mAb. Alanine substitution at position 9, 10 and 13 also reduced the binding of the #2 mAb. Mabs #4 and 7 showed a reduction in binding similar to #2 mAb, however, binding of #7 mAb to the peptide containing an alanine substitution at position 12 was still detectable (FIG. 3C). Since Ras protein position 11 of the Ras10-G12V peptide was already alanine, this position was next substituted with glycine (Ras10-A11G). Binding of the #2 mAb to Ras10-G12S peptide was also tested. Mab #2 showed weak but positive binding to T2 pulsed with Ras10-G12S and reduced binding to Ras10-A11G peptide. The loss of binding was not due to the reduction of the peptide binding affinity to the HLA-A2 molecule, as Ras10-A11G showed the strongest binding in T2 stabilization assays (FIG. 3D). These results show that the valine at Ras protein position 12 of the Ras10-G12V peptide is important for Ras mAb recognition and mAb #2 is highly specific for Ras10-G12V mutation. mAb #2 binding specificity using alanine substituted peptides and possible cross-reactive non-Ras peptides CT and MTH was further confirmed. No binding for either control CT or MTH peptide was seen (FIG. 3E). Flow cytometry data shows the binding of mAb #2 for various peptides and to HLA-A2 (FIG. 3F). Alanine substitution at Ras position 8 showed toxicity to T2 cells as shown by reduced HLA-A2 expression (FIG. 3G) and no reliable data were generated.

Figure 4A:
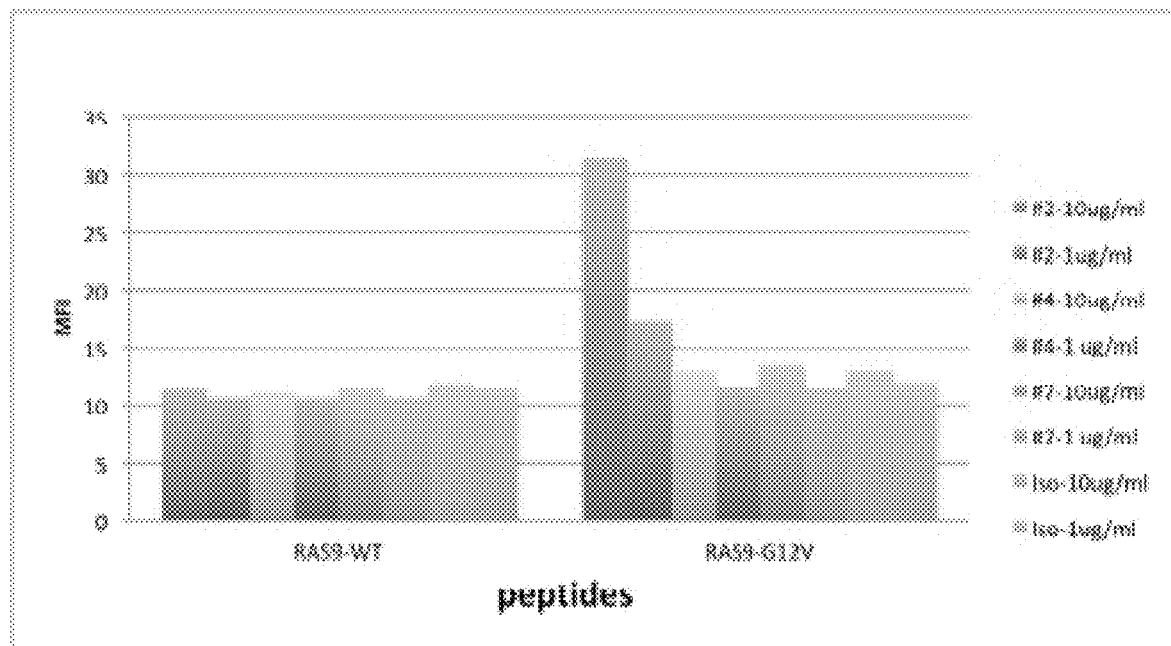
FIGS. 4A and 4B show Mab binding to RAS 9-mer peptides/HLA A2 complex. RAS9WT or G12V peptides were pulsed onto T2 cells at 50 µg/ml. The binding of the mAb to the peptide/HLA-A2 complex was measured by indirect (A) or indirect staining with mAbs conjugated to APC (B). Simultaneously, the cells were stained with anti-HLA-A2 mAb, BB7.2, to measure the relative binding of the peptides to HLA-A2 molecule.
Figure 4A:
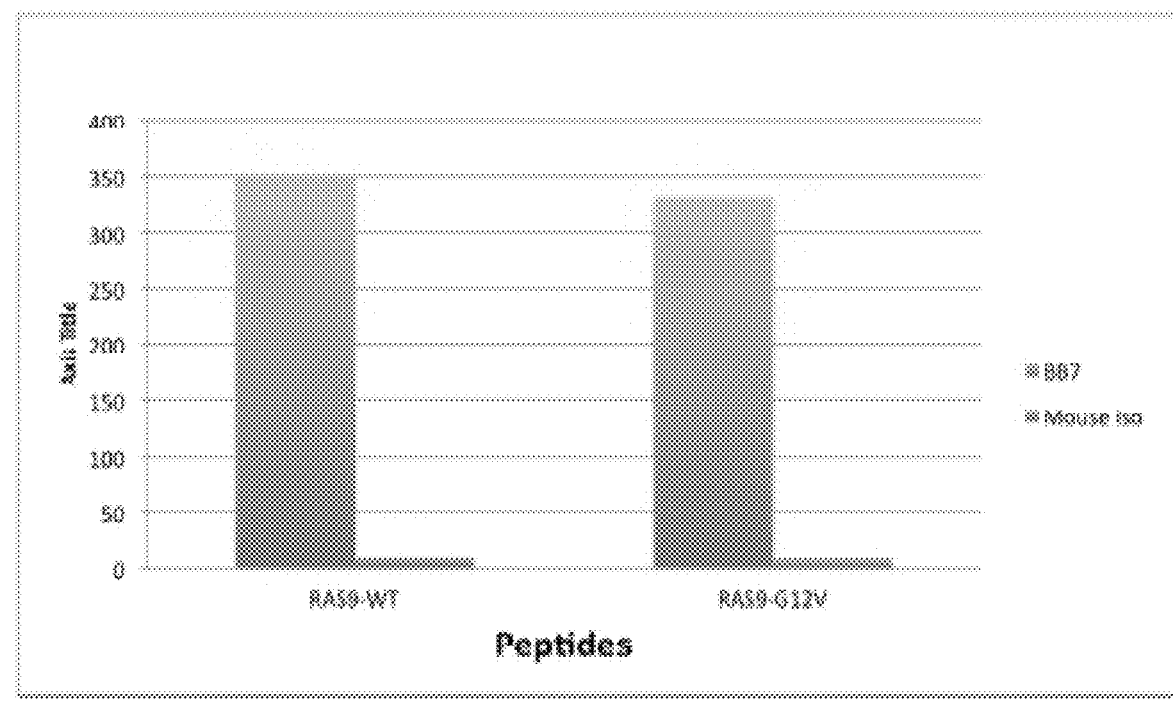
Figure 4B:
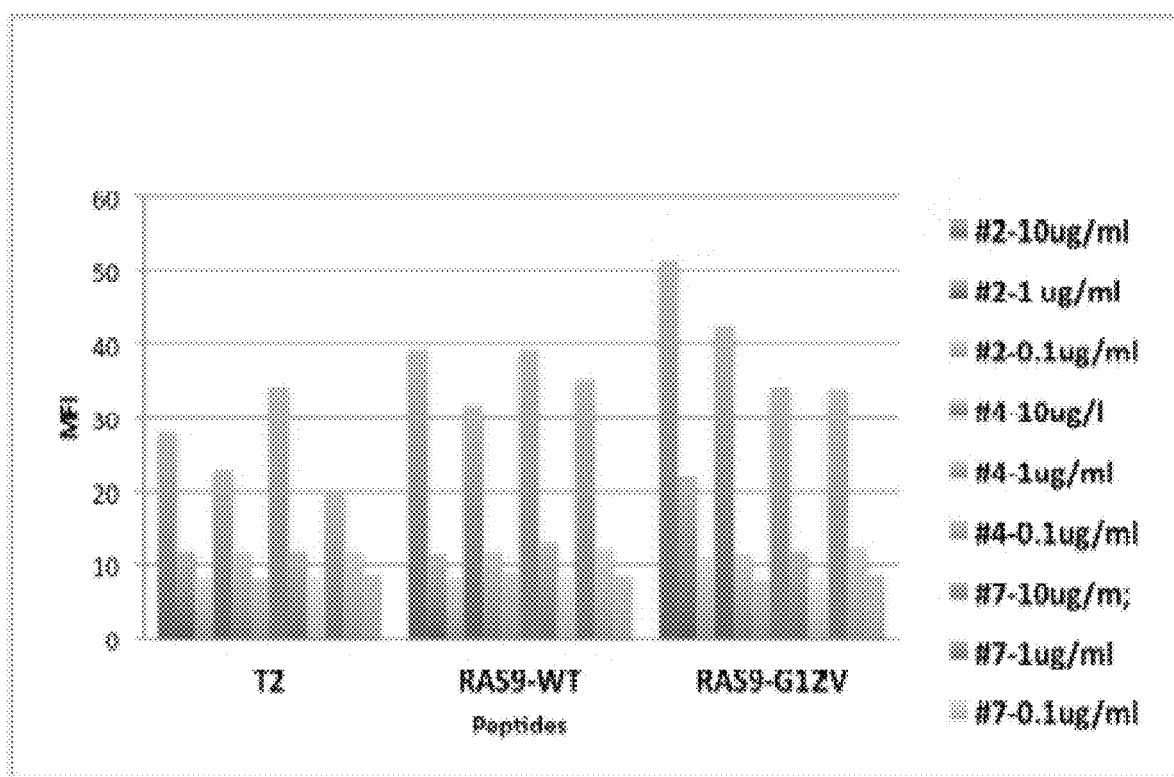
Figure 4B:
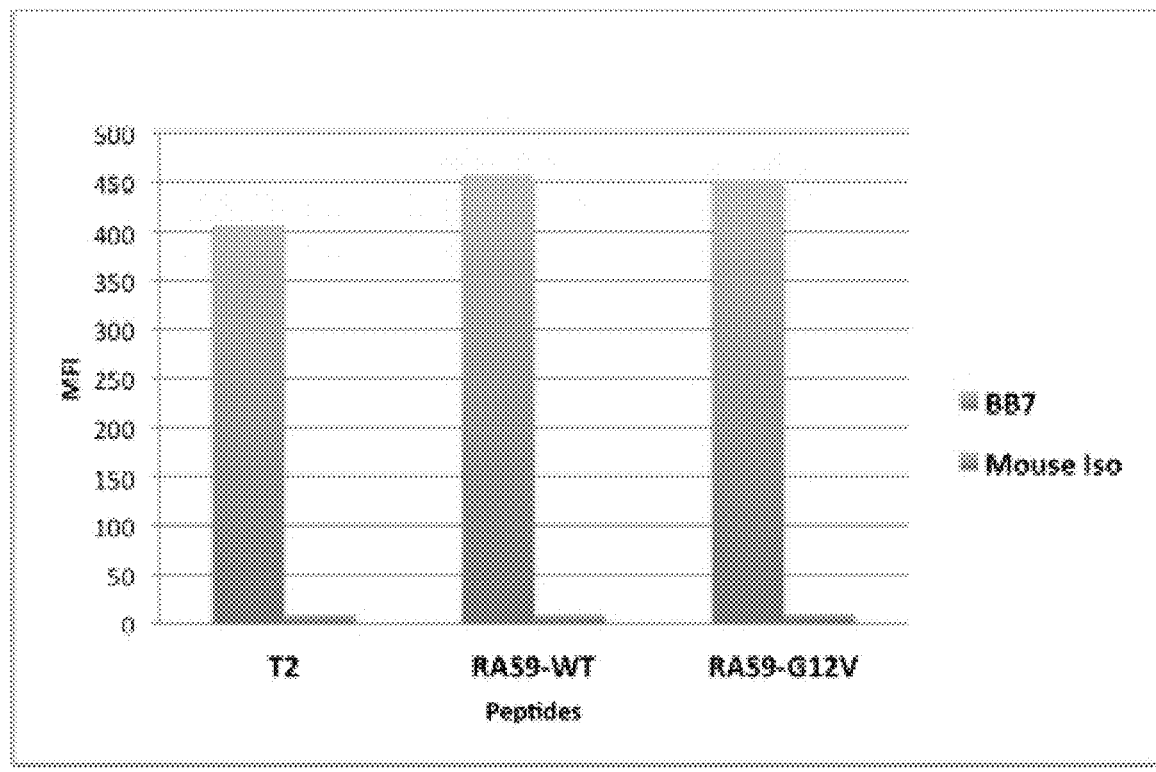

In addition to 10-mer peptides, binding of the mAbs to Ras 9-mer G12V mutation-derived peptides was tested. mAb #2 bound to Ras 9-mer G12V. mAbs #4 and 7 did not bind to either wild type or G12V mutant peptide, as shown by both indirect (FIG. 4A) and direct staining (FIG. 4B) and T2 confirmation of peptide binding (FIG. 4B lower.)

Example 10

Characterization of T-BiTE Constructs mAb killing functions can be enhanced in multiple ways. As a strategy to bring T cell cytotoxicity to the targets, bi-specific T cell engager (T-BiTE) constructs of the mAb were also generated and binding to the target Ras peptides was tested on T2 cells and binding to resting purified T cells (effectors) were tested by T-BiTE followed by a secondary mAb, mouse anti-myc conjugated to FITC, as BiTE constructs were myc-tagged.

Figure 5A:
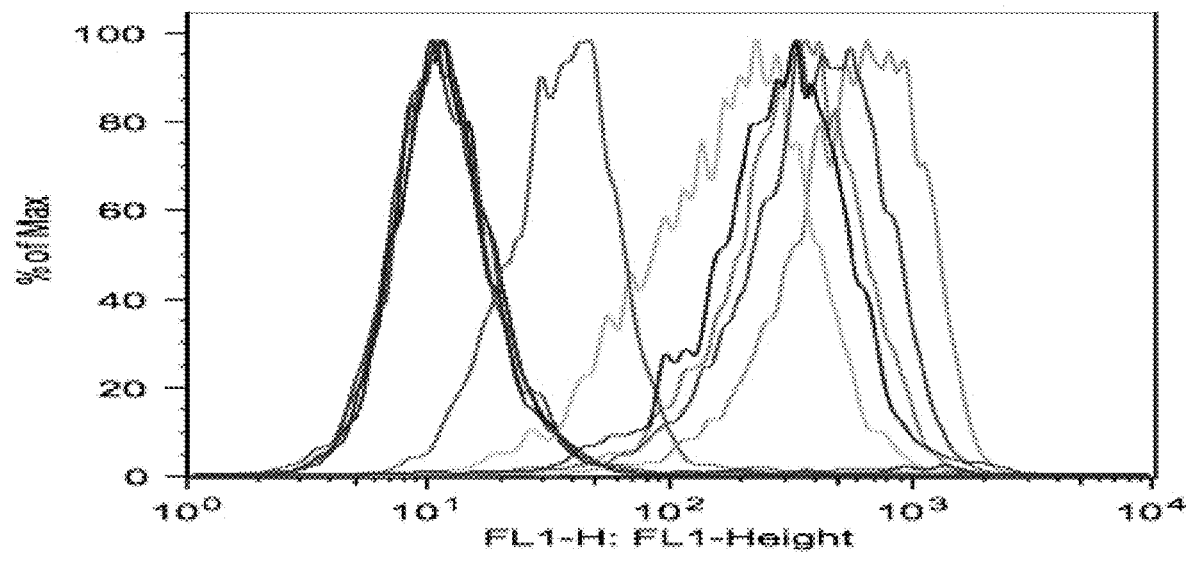
FIGS. 5A-C show binding of the BiTE derived from the RAS mAbs to peptide/HLA-A2 complex and T cells. T2 cells were pulsed with RAS10-WT or RAS10-G12V peptides, and were stained with BiTEs at indicated concentrations, followed by secondary mouse anti-myc mAb/FITC (A). MFI: upper panel for RAS-G12V and lower panel for RAS10-WT. (B and C) Simultaneously, CD3 T cells purified from a healthy donor by negative immunomagnetic cell separation using a pan T cell isolation kit (Miltenyi Biotec) were stained with BiTEs #2, upper panel #4 lower panel (B) or #7 (C) at indicated concentrations and followed by secondary mouse anti-myc mAb/FITC.
Figure 5A:
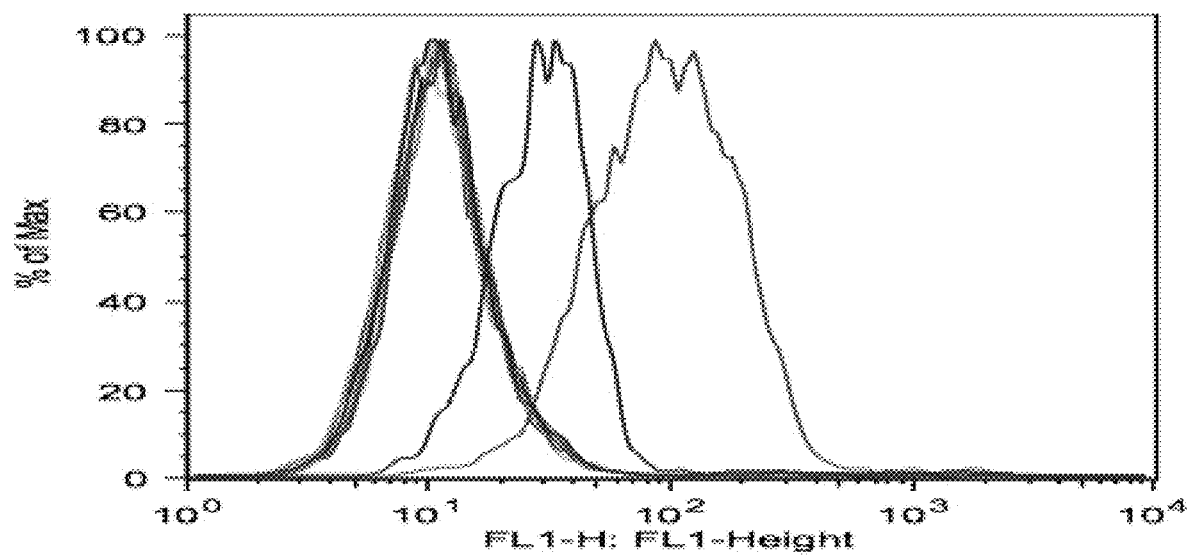
Figure 5B:
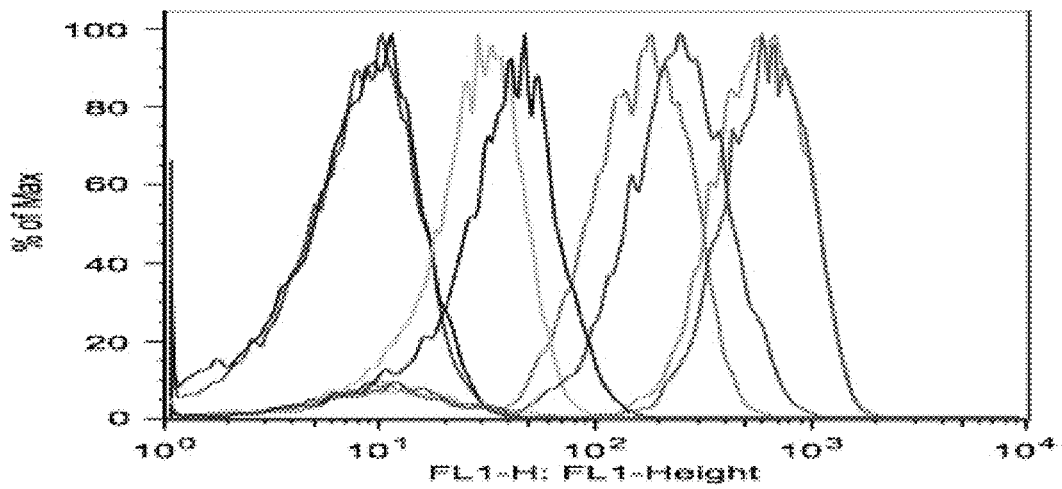
Figure 5B:
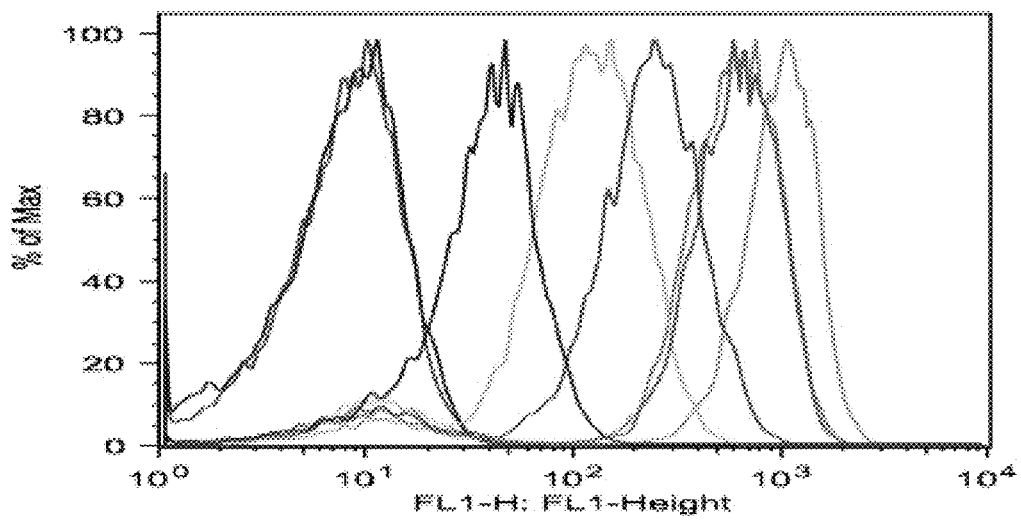
Figure 5C:
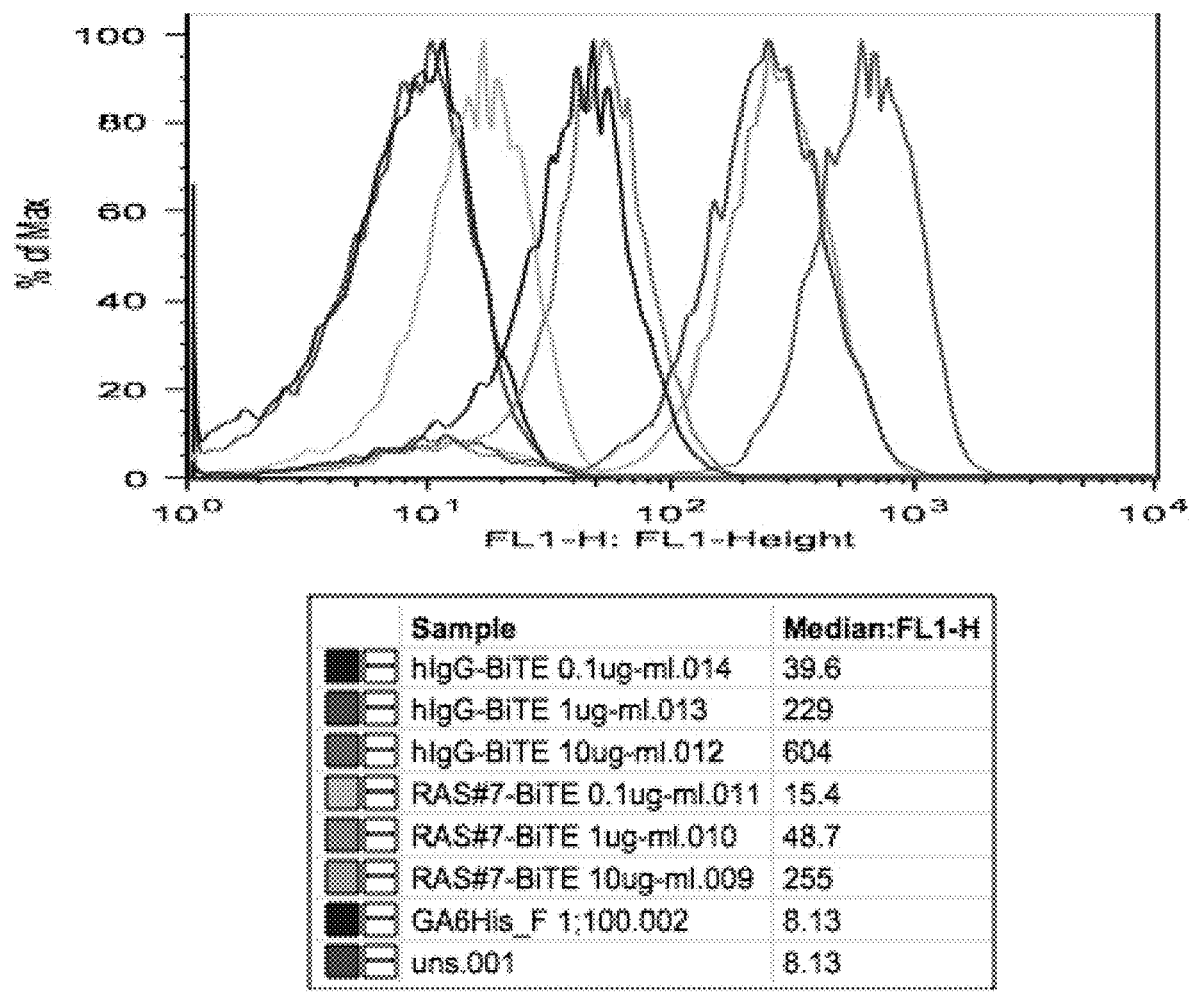

BiTEs retained their binding specificity and affinity, showing the best binding by #2 to Ras10-G12V peptide, followed by #7 and #4 mAbs. mAb #7 also showed binding to WT peptide (FIG. 5A). mAb #4 showed the strongest binding to CD3 T cells, followed by isotype control BITE, mAb #2 and #7 (FIGS. 5B and C).

Example 11

ADCC-Mediated Killing

Figure 6:
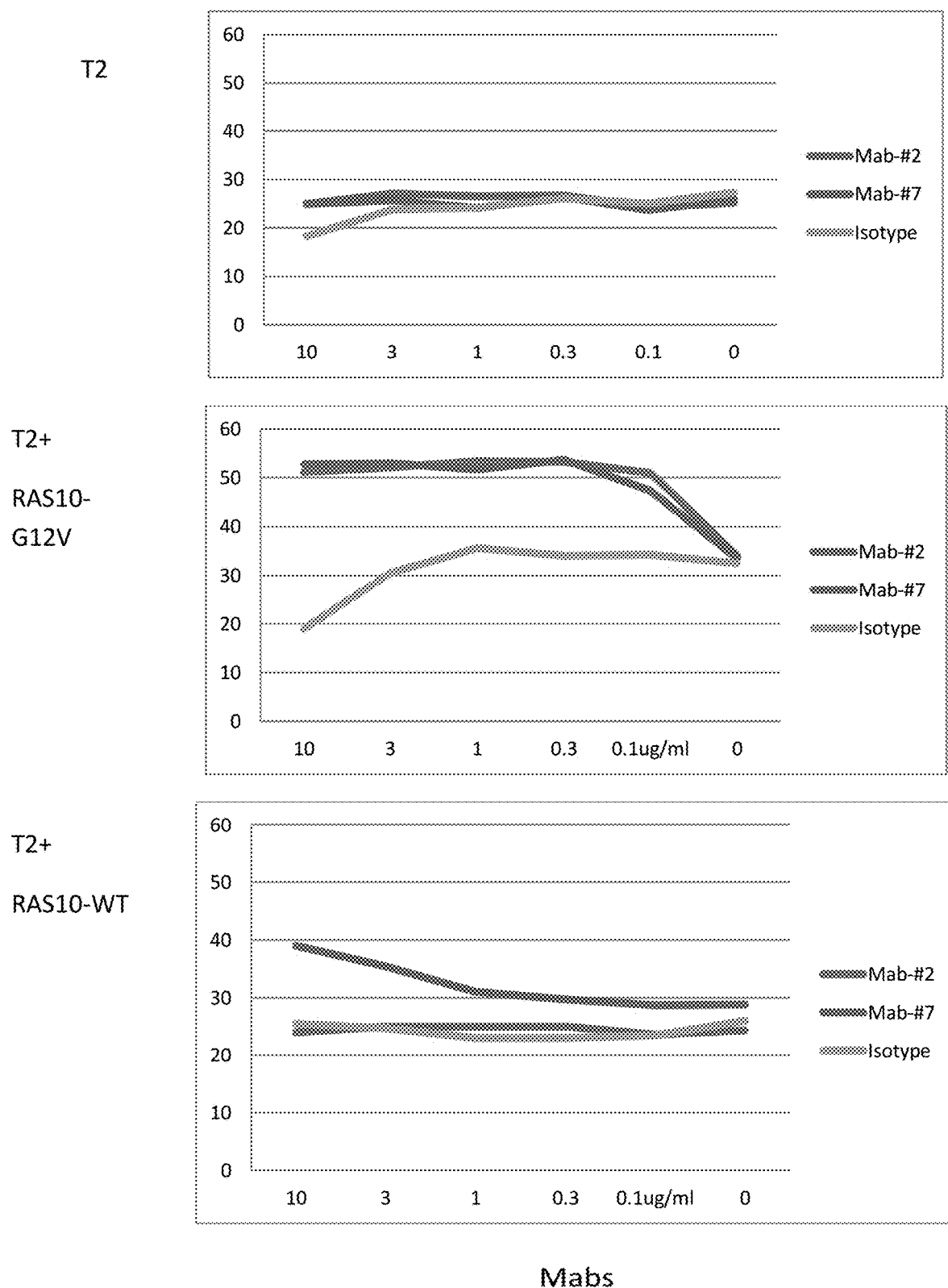
FIG. 6 shows ADCC mediated by fresh PBMCs in the presence of the RAS mAbs. T2 cells pulsed with peptides (50 μg/ml, 2 hrs) were incubated with human PBMCs in the presence or absence of mAbs #2, 7 or isotype control at an E:T ratio of 50:1, for 4-5 hrs. The killing was measured by standard 51Cr-release assay. Each data point was the average of triplicate cultures.

ADCC is considered to be one of the major effector mechanisms of therapeutic mAb in humans. Therefore, we next tested if the mAbs were able to mediate ADCC, using freshly isolated human PBMCs from healthy donor, in a standard 51Cr-release assay. (FIG. 6) Both mAbs #2 and 7 were able to kill T2 cells pulsed with Ras10-G12V peptides at the indicated concentrations in the similar degree. No killing was seen against unpulsed T2 cells. mAb #7 also killed the T2 pulsed with Ras10-WT peptide, but no killing was seen by #2 mAb. These results were consistent with the binding data and further demonstrated that the #2 mAb is specific for the mutant Ras10-G12V peptide/HLA-A2 complex.

Example 12

Killing by T-BITE's

Figure 7:
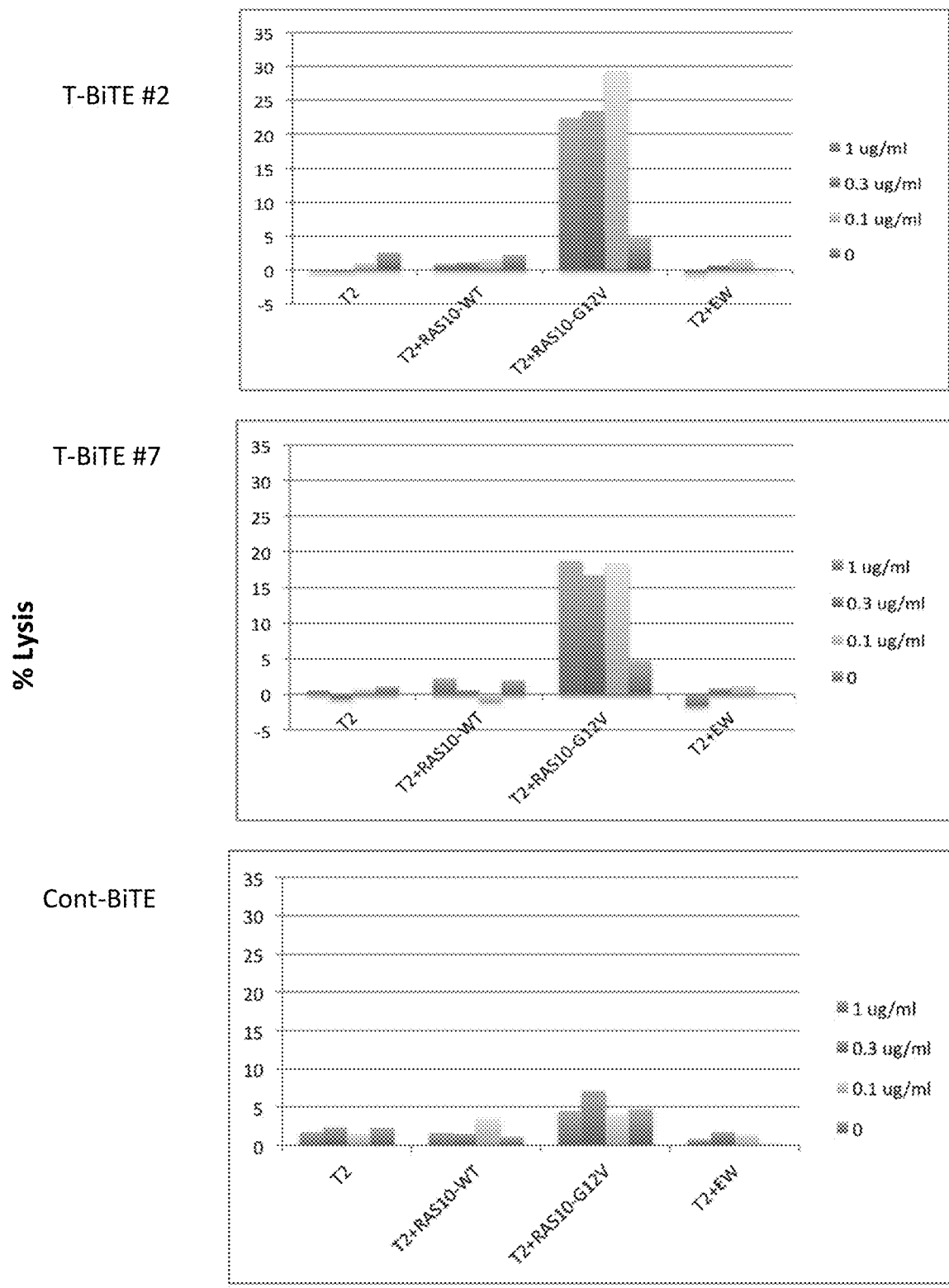
FIG. 7 shows T-BiTE-mediated killing by T cells. T2 cells pulsed with peptides (50 μg/ml, 2 hrs) were incubated with purified human resting T cells in the presence or absence of T-BiTEs #2, 7 or isotype control at an E:T ratio of 30:1, for 4-5 hrs. T cell killing was measured by $^{51}$Cr-release assay. Each data point was the average of triplicate cultures.

Next, whether T-BiTEs of Ras mAbs were able to mediate T cell killing against targets was tested. CD3 T cells were purified and cytotoxicity was measured by standard $^{51}$Cr-release assay, in the presence or absence of T-BiTEs #2, #7 and isotype-derived control BiTE. No killing was seen against control unpulsed T2 cells or cells pulsed with control peptide EW. Both #2 and #7 BiTEs were able to mediate T cell killing against T2 cells pulsed with Ras10-G12V peptide at the indicated concentrations of BiTEs (FIG. 7). BiTE #2 did not kill cells pulsed with Ras WT showing specificity of killing for the cells with the Ras mutant on the surface. BiTE #7 did not show killing against Ras10-WT pulsed T2 cells, which might be due to lower binding affinity to the WT/HLA-A2 complex, compared to Ras10-G12V/HLA-A2 complex.

EQUIVALENTS

The foregoing written specification is considered to be sufficient to enable one skilled in the art to practice the disclosure. The foregoing description and Examples detail certain embodiments of the disclosure and describes the best mode contemplated by the inventors. It will be appreciated, however, that no matter how detailed the foregoing may appear, the disclosure may be practiced in many ways and the disclosure should be construed in accordance with the appended claims and any equivalents thereof.

REFERENCES

1. Smith et al. *Oncogenic mutations in ras create HLA-A2.1 binding peptides but affect their extracellular antigen processing.* International Immunology Vol. 9(8), pp. 1085-1093, 1997.
2. Dao T. et al. *Identification of a human cyclin D1-derived peptide that induces human cytotoxic CD4 cells.* Plos One Vol. 4(9) e6730, 2009.
3. Cuesta et al., *Multivalent antibodies: when design surpasses evolution.* Trends in Biotechnology 28:355-362 2010.

The invention claimed is:

1. An antigen-binding protein comprising at least one of:
   (A) an antigen binding region having the amino acid sequence of one of SEQ ID NOS: 81, 82, 83, 84, 85, 86, 87, or 88;
   (B) an antigen binding region comprising a $V_H$ and a $V_L$ respectively, with amino acid sequences selected from SEQ ID NOs: (i) 7 and 9; (ii) 17 and 19; (iii) 27 and 29; (iv) 37 and 39; (v) 47 and 49; (vi) 57 and 59; (vii) 67 and 69; or (viii) 77 and 79; or
   (C) an antigen binding region comprising:
   (i) light chain complementarity determining regions (LC-CDRs) LC-CDR1, LC-CDR2 and LC-CDR3, with amino acid sequences SEQ ID NO: 4, SEQ ID NO: 5, and SEQ ID NO: 6, respectively and heavy chain CDRs (HC-CDRs) HC-CDR1, HC-CDR2 and HC-CDR3, with amino acid sequences SEQ ID NO: 1, SEQ ID NO: 2, and SEQ ID NO: 3, respectively;
   (ii) light chain complementarity determining regions (LC-CDRs) LC-CDR1, LC-CDR2 and LC-CDR3, with amino acid sequences SEQ ID NO: 14, SEQ ID NO: 15, and SEQ ID NO: 16, respectively and (b) heavy chain CDRs (HC-CDRs) HC-CDR1, HC-CDR2 and HC-CDR3, with amino acid sequences SEQ ID NO: 11, SEQ ID NO: 12, and SEQ ID NO: 13, respectively;
   (iii) light chain complementarity determining regions (LC-CDRs) LC-CDR1, LC-CDR2 and LC-CDR3, with amino acid sequences SEQ ID NO: 24, SEQ ID NO: 25, and SEQ ID NO: 26, respectively and (b) heavy chain CDRs (HC-CDRs) HC-CDR1, HC-CDR2 and HC-CDR3, with amino acid sequences SEQ ID NO: 21, SEQ ID NO: 22, and SEQ ID NO: 23, respectively;
   (iv) light chain complementarity determining regions (LC-CDRs) LC-CDR1, LC-CDR2 and LC-CDR3, with amino acid sequences SEQ ID NO: 34, SEQ ID NO: 35, and SEQ ID NO: 36, respectively and (b) heavy chain CDRs (HC-CDRs) HC-CDR1, HC-CDR2 and HC-CDR3, with amino acid sequences SEQ ID NO: 31, SEQ ID NO: 32, and SEQ ID NO: 33, respectively;
   (v) light chain complementarity determining regions (LC-CDRs) LC-CDR1, LC-CDR2 and LC-CDR3, with amino acid sequences SEQ ID NO: 44, SEQ ID NO: 45, and SEQ ID NO: 46, respectively and (b) heavy chain CDRs (HC-CDRs) HC-CDR1, HC-CDR2 and HC-CDR3, with amino acid sequences SEQ ID NO: 41, SEQ ID NO: 42, and SEQ ID NO: 43, respectively;
   (vi) light chain complementarity determining regions (LC-CDRs) LC-CDR1, LC-CDR2 and LC-CDR3, with amino acid sequences SEQ ID NO: 54, SEQ ID NO: 55, and SEQ ID NO: 56, respectively and (b) heavy chain CDRs (HC-CDRs) HC-CDR1, HC-CDR2 and HC-CDR3, with amino acid sequences SEQ ID NO: 51, SEQ ID NO: 52, and SEQ ID NO: 53, respectively;
   (vii) light chain complementarity determining regions (LC-CDRs) LC-CDR1, LC-CDR2 and LC-CDR3, with amino acid sequences SEQ ID NO: 64, SEQ ID NO: 65, and SEQ ID NO: 66, respectively and (b) heavy chain CDRs (HC-CDRs) HC-CDR1, HC-CDR2 and HC-CDR3, with amino acid sequences SEQ ID NO: 61, SEQ ID NO: 62, and SEQ ID NO: 63, respectively; or
   (viii) light chain complementarity determining regions (LC-CDRs) LC-CDR1, LC-CDR2 and LC-CDR3, with amino acid sequences SEQ ID NO: 74, SEQ ID NO: 75, and SEQ ID NO: 76, respectively and (b) heavy chain CDRs (HC-CDRs) HC-CDR1, HC-CDR2 and HC-CDR3, with amino acid sequences SEQ ID NO: 71, SEQ ID NO: 72, and SEQ ID NO: 73, respectively.

2. The antigen-binding protein of claim 1, wherein the antigen-binding protein is an antibody.

3. The antigen-binding protein of claim 2, wherein the antibody comprises a human variable region framework region.

4. The antigen-binding protein of claim 2, wherein the antibody is fully human.

5. The antigen-binding protein of claim 2, wherein the antibody is a full-length antibody, an intact antibody, a Fab fragment, a F(ab')$_2$ fragment, or a single chain variable fragment (scFv).

6. The antigen-binding protein of claim 1, wherein the antigen-binding protein is a chimeric antigen receptor (CAR).

7. The antigen-binding protein of claim 1, conjugated to a therapeutic agent.

8. The antigen-binding protein of claim 7, wherein said therapeutic agent is a drug, toxin, radioisotope, protein, or peptide.

9. A nucleic acid that encodes an antigen-binding protein of claim 1, wherein said nucleic acid comprises:
   (A) first and second nucleotide sequences selected from the group consisting of SEQ ID NOS: 8 and 10; 18 and 20; 28 and 30; 38 and 40; 48 and 50; 58 and 60; 68 and 70; and 78 and 80; or
   (B) a nucleotide sequence selected from the group consisting of SEQ ID NOS: 91, 92, 93, 94, 95, 96, 97, and 98.

10. The nucleic acid of claim 9, wherein said first nucleotide sequence encodes a $V_H$ region and said second nucleotide sequence encodes a $V_L$ region.

11. The nucleic acid of claim 9, wherein said nucleotide sequence encodes a scFv.

12. A fusion protein comprising an antigen-binding protein of claim 1.

13. The antigen-binding protein of claim 5, wherein the antibody is a single-chain variable fragment (scFv) comprising the amino acid sequence of an antigen-binding protein selected from the group consisting of SEQ ID NOS: 81, 82, 83, 84, 85, 86, 87, and 88.

14. The antigen-binding protein of claim 5, wherein the antibody is a scFv comprising a $V_H$ and a $V_L$ linked by an amino acid spacer, wherein the $V_H$ and $V_L$ respectively comprise an amino acid sequence selected from the group consisting of SEQ ID NOS: (i) 7 and 9; (ii) 17 and 19; (iii) 27 and 29; (iv) 37 and 39; (v) 47 and 49; (vi) 57 and 59; (vii) 67 and 69; and (viii) 77 and 79.

15. The antigen-binding protein of claim 5, wherein the antibody is a scFv comprising:
  (i) light chain complementarity determining regions (LC-CDRs) LC-CDR1, LC-CDR2 and LC-CDR3, with amino acid sequences SEQ ID NO: 4, SEQ ID NO: 5, and SEQ ID NO: 6, respectively and heavy chain CDRs (HC-CDRs) HC-CDR1, HC-CDR2 and HC-CDR3, with amino acid sequences SEQ ID NO: 1, SEQ ID NO: 2, and SEQ ID NO: 3, respectively;
  (ii) light chain complementarity determining regions (LC-CDRs) LC-CDR1, LC-CDR2 and LC-CDR3, with amino acid sequences SEQ ID NO: 14, SEQ ID NO: 15, and SEQ ID NO: 16, respectively and heavy chain CDRs (HC-CDRs) HC-CDR1, HC-CDR2 and HC-CDR3, with amino acid sequences SEQ ID NO: 11, SEQ ID NO: 12, and SEQ ID NO: 13, respectively;
  (iii) light chain complementarity determining regions (LC-CDRs) LC-CDR1, LC-CDR2 and LC-CDR3, with amino acid sequences SEQ ID NO: 24, SEQ ID NO: 25, and SEQ ID NO: 26, respectively and heavy chain CDRs (HC-CDRs) HC-CDR1, HC-CDR2 and HC-CDR3, with amino acid sequences SEQ ID NO: 21, SEQ ID NO: 22, and SEQ ID NO: 23, respectively;
  (iv) light chain complementarity determining regions (LC-CDRs) LC-CDR1, LC-CDR2 and LC-CDR3, with amino acid sequences SEQ ID NO: 34, SEQ ID NO: 35, and SEQ ID NO: 36, respectively and heavy chain CDRs (HC-CDRs) HC-CDR1, HC-CDR2 and HC-CDR3, with amino acid sequences SEQ ID NO: 31, SEQ ID NO: 32, and SEQ ID NO: 33, respectively;
  (v) light chain complementarity determining regions (LC-CDRs) LC-CDR1, LC-CDR2 and LC-CDR3, with amino acid sequences SEQ ID NO: 44, SEQ ID NO: 45, and SEQ ID NO: 46, respectively and heavy chain CDRs (HC-CDRs) HC-CDR1, HC-CDR2 and HC-CDR3, with amino acid sequences SEQ ID NO: 41, SEQ ID NO: 42, and SEQ ID NO: 43, respectively;
  (vi) light chain complementarity determining regions (LC-CDRs) LC-CDR1, LC-CDR2 and LC-CDR3, with amino acid sequences SEQ ID NO: 54, SEQ ID NO: 55, and SEQ ID NO: 56, respectively and heavy chain CDRs (HC-CDRs) HC-CDR1, HC-CDR2 and HC-CDR3, with amino acid sequences SEQ ID NO: 51, SEQ ID NO: 52, and SEQ ID NO: 53, respectively;
  (vii) light chain complementarity determining regions (LC-CDRs) LC-CDR1, LC-CDR2 and LC-CDR3, with amino acid sequences SEQ ID NO: 64, SEQ ID NO: 65, and SEQ ID NO: 66, respectively and heavy chain CDRs (HC-CDRs) HC-CDR1, HC-CDR2 and HC-CDR3, with amino acid sequences SEQ ID NO: 61, SEQ ID NO: 62, and SEQ ID NO: 63, respectively; or
  (viii) light chain complementarity determining regions (LC-CDRs) LC-CDR1, LC-CDR2 and LC-CDR3, with amino acid sequences SEQ ID NO: 74, SEQ ID NO: 75, and SEQ ID NO: 76, respectively and heavy chain CDRs (HC-CDRs) HC-CDR1, HC-CDR2 and HC-CDR3, with amino acid sequences SEQ ID NO: 71, SEQ ID NO: 72, and SEQ ID NO: 73, respectively.

16. An immunoconjugate comprising a first component which is an antigen-binding protein of claim 1.

17. The immunoconjugate of claim 16, comprising a second component having a second amino acid sequence.

18. The immunoconjugate according to claim 16, further comprising a cytotoxin or radionuclide.

19. The immunoconjugate of claim 17, wherein the second component is a binding protein or antibody having a binding specificity for a target that is different from the binding specificity of the first component.

20. A bispecific antibody comprising first and second antigen-binding portions wherein said first antigen-binding portion is an antigen-binding protein of claim 1.

21. The bispecific antibody of claim 20, wherein the bispecific antibody comprises a second antigen-binding portion that has a binding specificity for a target that is different from the binding specificity of the first antigen binding portion.

22. A pharmaceutical composition comprising the antigen-binding proteins or antigen-binding portions thereof of claim 1 and a pharmaceutically acceptable carrier.

23. A method for selectively killing a human cancer cell that displays a RasG12V/MHC epitope on its surface comprising contacting said cell with an antigen-binding protein comprising:
  (A) an antigen binding region having the amino acid sequence of one of SEQ ID NOS: 81, 82, 83, 84, 85, 86, 87, 88, or a combination thereof; or
  (B) an antigen binding region comprising a $V_H$ and a $V_L$ respectively, with amino acid sequences selected from SEQ ID NOs: (i) 7 and 9; (ii) 17 and 19; (iii) 27 and 29; (iv) 37 and 39; (v) 47 and 49; (vi) 57 and 59; vii) 67 and 69; (viii) 77 and 79; (ix) 87 and 89, or a combination thereof,
  wherein the RasG12V/MHC epitope comprises the amino acid sequence of SEQ ID NO: 116 or SEQ ID NO: 111.

24. A vector comprising the nucleic acid of claim 9.

25. A cell comprising the nucleic acid of claim 9.

26. A pharmaceutical composition comprising a nucleic acid of claim 9.

27. A bispecific antibody comprising a least one amino acid sequence of an antigen-binding protein of claim 1.

28. The bispecific antibody of claim 27, wherein said bispecific antibody has the amino acid sequence of SEQ ID NO: 103.

29. A pharmaceutical composition comprising the bispecific antibody of claim 27.

* * * * *

SEQUENCE LISTING

```
<160> NUMBER OF SEQ ID NOS: 118

<210> SEQ ID NO 1
<211> LENGTH: 8
<212> TYPE: PRT
<213> ORGANISM: Artificial Sequence
<220> FEATURE:
<223> OTHER INFORMATION: synthetic

<400> SEQUENCE: 1

Gly Gly Thr Phe Ser Ser Tyr Ala
1               5

<210> SEQ ID NO 2
<211> LENGTH: 8
<212> TYPE: PRT
<213> ORGANISM: Artificial Sequence
<220> FEATURE:
<223> OTHER INFORMATION: synthetic

<400> SEQUENCE: 2

Ile Ile Pro Ile Phe Gly Lys Gly
1               5

<210> SEQ ID NO 3
<211> LENGTH: 11
<212> TYPE: PRT
<213> ORGANISM: Artificial Sequence
<220> FEATURE:
<223> OTHER INFORMATION: synthetic

<400> SEQUENCE: 3

Ala Arg His Ile Pro Thr Phe Ser Phe Asp Tyr
1               5                   10

<210> SEQ ID NO 4
<211> LENGTH: 9
<212> TYPE: PRT
<213> ORGANISM: Artificial Sequence
<220> FEATURE:
<223> OTHER INFORMATION: synthetic

<400> SEQUENCE: 4

Ser Ser Asn Ile Gly Ala Gly Tyr Asp
1               5

<210> SEQ ID NO 5
<211> LENGTH: 3
```

<212> TYPE: PRT
<213> ORGANISM: Artificial Sequence
<220> FEATURE:
<223> OTHER INFORMATION: synthetic

<400> SEQUENCE: 5

Gly Asn Ser
1

<210> SEQ ID NO 6
<211> LENGTH: 11
<212> TYPE: PRT
<213> ORGANISM: Artificial Sequence
<220> FEATURE:
<223> OTHER INFORMATION: synthetic

<400> SEQUENCE: 6

Gln Ser Tyr Asp Ser Ser Leu Ser Gly Tyr Val
1               5                   10

<210> SEQ ID NO 7
<211> LENGTH: 118
<212> TYPE: PRT
<213> ORGANISM: Artificial Sequence
<220> FEATURE:
<223> OTHER INFORMATION: synthetic

<400> SEQUENCE: 7

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Lys Gly Asn Tyr Pro Gln Lys Phe
    50                  55                  60

Gln Gly Arg Val Thr Ile Thr Ala Asp Glu Ser Thr Gly Thr Ala Tyr
65                  70                  75                  80

Met Glu Leu Ser Ser Leu Arg Ser Glu Asp Thr Ala Val Tyr Tyr Cys
                85                  90                  95

Ala Arg His Ile Pro Thr Phe Ser Phe Asp Tyr Trp Gly Gln Gly Thr
            100                 105                 110

Leu Val Thr Val Ser Ser
        115

<210> SEQ ID NO 8
<211> LENGTH: 354
<212> TYPE: DNA
<213> ORGANISM: Artificial Sequence
<220> FEATURE:
<223> OTHER INFORMATION: synthetic

<400> SEQUENCE: 8
caggtgcagc tggtgcagtc tggggctgag gtgaagaagc ctgggtcctc ggtgaaggtc      60
tcctgcaagg cttctggagg cacct tcagc agctatgcta tcagctgggt gcgacaggcc    120
cctggacaag gcttgagtg gatgggaggt atcatccct a tctttggtaa aggaaactac    180
ccacagaagt tccagggcag agtcacgatt accgcggacg aatctacggg cacagcctac    240
atggagctga gcagcctgag atctgaggac acggccgtgt attactgtgc gcgccatatc    300
ccgactttct ctttcgatta ctgggg tcaa ggtactctgg tgaccgtctc ctca         354

<210> SEQ ID NO 9
<211> LENGTH: 112
<212> TYPE: PRT
<213> ORGANISM: Artificial Sequence
<220> FEATURE:
<223> OTHER INFORMATION: synthetic

<400> SEQUENCE: 9

Gln Ser Val Leu Thr Gln Pro Pro Ser Val Ser Gly Ala Pro Gly Gln
1               5                   10                  15

Arg Val Thr Ile Ser Cys Thr Gly Ser Ser Asn Ile Gly Ala Gly
            20                  25                  30

Tyr Asp Val His Trp Tyr Gln Gln Leu Pro Gly Thr Ala Pro Lys Leu
            35                  40                  45

Leu Ile Tyr Gly Asn Ser Asn Arg Pro Ser Gly Val Pro Asp Arg Phe
        50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Tyr Val Phe Gly Thr Gly Thr Lys Val Thr Val Leu Gly
            100                 105                 110

<210> SEQ ID NO 10
<211> LENGTH: 336
<212> TYPE: DNA
<213> ORGANISM: Artificial Sequence
<220> FEATURE:
<223> OTHER INFORMATION: synthetic

<400> SEQUENCE: 10
cagtctgtgt tgacgcagcc gccctcagtg tctggggccc cagggcagag ggtcaccatc      60
tcctgcactg ggagcagctc caacatcggg gcaggttatg atgtacactg gtaccagcag     120
cttccaggaa cagcccccaa actcctcatc tatggtaaca gcaatcggcc ctcagggtc      180 cctgaccgat tctctggctc caagtctggc acctcagcct ccctggccat cactgggctc     240
caggctgagg atgaggctga ttattactgc cagtcctatg acagcagcct gagtggttat     300
gtcttcggaa ctgggaccaa ggtcaccgtc ctaggt                               336

<210> SEQ ID NO 11
<211> LENGTH: 8
<212> TYPE: PRT
<213> ORGANISM: Artificial Sequence
<220> FEATURE:
<223> OTHER INFORMATION: synthetic

<400> SEQUENCE: 11

Gly Gly Thr Phe Ser Ser Tyr Thr
1               5

<210> SEQ ID NO 12
<211> LENGTH: 8
<212> TYPE: PRT
<213> ORGANISM: Artificial Sequence
<220> FEATURE:
<223> OTHER INFORMATION: synthetic

<400> SEQUENCE: 12

Phe Ile Pro Ile Ser Gly Thr Val
1               5

<210> SEQ ID NO 13
<211> LENGTH: 10
<212> TYPE: PRT
<213> ORGANISM: Artificial Sequence
<220> FEATURE:
<223> OTHER INFORMATION: synthetic

<400> SEQUENCE: 13

Ala Arg Pro Leu Asp Trp Thr Glu Asp Ile
1               5                   10

<210> SEQ ID NO 14
<211> LENGTH: 9
<212> TYPE: PRT
<213> ORGANISM: Artificial Sequence
<220> FEATURE:
<223> OTHER INFORMATION: synthetic

<400> SEQUENCE: 14

Ser Ser Asn Ile Gly Ala Gly Tyr Asp
1               5

<210> SEQ ID NO 15
<211> LENGTH: 3
<212> TYPE: PRT
<213> ORGANISM: Artificial Sequence
<220> FEATURE:
<223> OTHER INFORMATION: synthetic

<400> SEQUENCE: 15

Gly Asn Ser
1

<210> SEQ ID NO 16
<211> LENGTH: 11
<212> TYPE: PRT
<213> ORGANISM: Artificial Sequence
<220> FEATURE:
<223> OTHER INFORMATION: synthetic

<400> SEQUENCE: 16

Gln Ser Tyr Asp Ser Ser Leu Ser Gly Ser Val
1               5                   10

<210> SEQ ID NO 17
<211> LENGTH: 117
<212> TYPE: PRT
<213> ORGANISM: Artificial Sequence
<220> FEATURE:
<223> OTHER INFORMATION: synthetic

<400> SEQUENCE: 17

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Thr Ile Asn Trp Val Arg Gln Ala Pro Gly Gln Gly Leu Glu Trp Met
        35                  40                  45

Gly Gly Phe Ile Pro Ile Ser Gly Thr Val Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Pro Leu Asp Trp Thr Glu Asp Ile Trp Gly Gln Gly Thr Leu
                100                 105                 110

Val Thr Val Ser Ser
        115

<210> SEQ ID NO 18
<211> LENGTH: 351
<212> TYPE: DNA
<213> ORGANISM: Artificial Sequence
<220> FEATURE:
<223> OTHER INFORMATION: synthetic

<400> SEQUENCE: 18
caggtgcagc tggtgcagtc tggggctgag gtgaagaagc ctgggtcctc ggtgaaggtc    60
tcctgcaagg cttctggagg caccttcagc agctatacta tcaactgggt gcgacaggcc   120
cctggacaag ggcttgagtg gatgggaggg ttcatccgta tctctggtac agtaaactac   180
gcacagaagt tccagggcag agtcacgatt accgcggacg aatccacgag cacagcctac   240
atggaactga gcagcctgag atctgaggac actgccgtgt attactgtgc gcgcccgctg   300
gactggactg aagatatctg ggtcaaggt actctggtga ccgtctcctc a            351

<210> SEQ ID NO 19
<211> LENGTH: 112
<212> TYPE: PRT
<213> ORGANISM: Artificial Sequence
<220> FEATURE:
<223> OTHER INFORMATION: synthetic

<400> SEQUENCE: 19

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Ser Val Phe Gly Thr Gly Thr Lys Val Thr Val Leu Gly
            100                 105                 110

<210> SEQ ID NO 20
<211> LENGTH: 336
<212> TYPE: DNA
<213> ORGANISM: Artificial Sequence
<220> FEATURE:
<223> OTHER INFORMATION: synthetic

<400> SEQUENCE: 20
cagtctgtgt tgacgcagcc gccctcagtg tctggggccc agggcagag ggtcaccatc     60 tcctgcactg ggagcagctc caacatcggg gcaggttatg atgtacactg gtaccagcag   120
cttccaggaa cagcccccaa actcctcatc tatggtaaca gcaatcggcc ctcaggggtc   180
cctgaccgat tctctggctc caagtctggc acctcagcct ccctggccat cactgggctc   240
caggctgagg atgaggctga ttattactgc cagtcctatg acagcagcct gagtggttca   300
gtcttcggaa ctgggaccaa ggtcaccgtc ctaggt                                    336

<210> SEQ ID NO 21
<211> LENGTH: 8
<212> TYPE: PRT
<213> ORGANISM: Artificial Sequence
<220> FEATURE:
<223> OTHER INFORMATION: synthetic

<400> SEQUENCE: 21

Gly Tyr Thr Phe Thr Ala Tyr Tyr
1               5

<210> SEQ ID NO 22
<211> LENGTH: 8
<212> TYPE: PRT
<213> ORGANISM: Artificial Sequence
<220> FEATURE:
<223> OTHER INFORMATION: synthetic

<400> SEQUENCE: 22

Met Asn Thr Asn Asn Gly Ala Thr
1               5

<210> SEQ ID NO 23
<211> LENGTH: 12
<212> TYPE: PRT
<213> ORGANISM: Artificial Sequence
<220> FEATURE:
<223> OTHER INFORMATION: synthetic

<400> SEQUENCE: 23

Ala Arg Gly Asp Ile Ser Gln Asp Phe Ala Asp Val
1               5                   10

<210> SEQ ID NO 24
<211> LENGTH: 8
<212> TYPE: PRT
<213> ORGANISM: Artificial Sequence
<220> FEATURE:
<223> OTHER INFORMATION: synthetic

<400> SEQUENCE: 24

Ser Gly Ser Ile Ala Ser Asn Tyr
1               5

<210> SEQ ID NO 25
<211> LENGTH: 3
<212> TYPE: PRT
<213> ORGANISM: Artificial Sequence
<220> FEATURE:
<223> OTHER INFORMATION: synthetic

<400> SEQUENCE: 25

Glu Asp Asn
1

<210> SEQ ID NO 26
<211> LENGTH: 10
<212> TYPE: PRT
<213> ORGANISM: Artificial Sequence
<220> FEATURE:
<223> OTHER INFORMATION: synthetic

<400> SEQUENCE: 26

Gln Ser Tyr Asp Asp Ile Asn His Trp Val

<210> SEQ ID NO 27
<211> LENGTH: 119
<212> TYPE: PRT
<213> ORGANISM: Artificial Sequence
<220> FEATURE:
<223> OTHER INFORMATION: synthetic

<400> SEQUENCE: 27

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ala Tyr
            20                  25                  30

Tyr Leu His Trp Leu Arg Gln Ala Pro Gly Gln Gly Leu Glu Trp Met
        35                  40                  45

Gly Trp Met Asn Thr Asn Asn Gly Ala Thr Arg Tyr Ala Gln Lys Phe
    50                  55                  60

Gln Asp Arg Val Thr Met Thr Arg Asp Thr Ser Ile Asn Thr Ala Tyr
65                  70                  75                  80

Met Glu Met Ser Gly Leu Ser Ser Asp Asp Thr Ala Met Tyr Tyr Cys
                85                  90                  95

Ala Arg Gly Asp Ile Ser Gln Asp Phe Ala Asp Val Trp Gly Gln Gly
            100                 105                 110

Thr Leu Val Thr Val Ser Ser
        115
```

<210> SEQ ID NO 28
<211> LENGTH: 357
<212> TYPE: DNA
<213> ORGANISM: Artificial Sequence
<220> FEATURE:
<223> OTHER INFORMATION: synthetic

<400> SEQUENCE: 28

```
gaggtgcagc tggtgcagtc tggggctgag gtgaagaagc ctggggcctc agtgaaggtc    60
tcctgcaagg cttctggata caccttcacc gcctactatc tgcactggct gcgacaggcc   120
cctggacaag ggcttgagtg gatgggatgg atgaatacta acaatggtgc cacaaggtat   180
gcacagaaat tccaggacag ggtcaccatg accagggaca cgtccattaa cacagcctac   240
atggagatga gcgggctgtc atctgacgac accgccatgt attactgtgc gcgcggtgat   300
atctctcagg acttcgctga tgtttggggt caaggtactc tggtgaccgt ctcctca      357
```

<210> SEQ ID NO 29
<211> LENGTH: 112
<212> TYPE: PRT
<213> ORGANISM: Artificial Sequence
<220> FEATURE:
<223> OTHER INFORMATION: synthetic

<400> SEQUENCE: 29

```
Asn Phe Met Leu Thr Gln Pro His Ser Val Ser Glu Ser Pro Gly Lys
1               5                   10                  15

Thr Val Thr Ile Ser Cys Thr Gly Ser Ser Gly Ser Ile Ala Ser Asn
            20                  25                  30

Tyr Val Gln Trp Tyr Gln Gln Arg Pro Gly Ser Ala Pro Thr Ile Leu
        35                  40                  45

Ile Tyr Glu Asp Asn Lys Arg Pro Ser Gly Val Pro Asp Arg Phe Ser
    50                  55                  60
```

Gly Ser Ile Asp Ser Ser Asn Ser Ala Ser Leu Thr Ile Ser Gly
65                  70                  75                  80

Leu Lys Thr Gly Asp Glu Ala Asp Tyr Tyr Cys Gln Ser Tyr Asp
                85                  90                  95

Ile Asn His Trp Val Phe Gly Gly Gly Thr Lys Leu Thr Val Leu Gly
            100                 105                 110

<210> SEQ ID NO 30
<211> LENGTH: 336
<212> TYPE: DNA
<213> ORGANISM: Artificial Sequence
<220> FEATURE:
<223> OTHER INFORMATION: synthetic

<400> SEQUENCE: 30
aattttatgc tgactcagcc ccactctgtg tcggagtctc cggggaagac ggtaaccatc    60
tcctgcaccg gcagcagtgg cagcattgcc agcaactatg tgcagtggta tcagcagcgc   120
ccgggcagtg cccccaccat tctgatctat gaggataaca aaagaccctc tggggtccct   180
gatcggttct ctggctccat cgacagctcc tccaactctg cctccctcac catctctgga   240
ctgaagactg gggacgaggc tgactactac tgtcagtctt atgatgacat caatcattgg   300
gtgttcggcg gagggaccaa gctgaccgtc ctaggt                             336

<210> SEQ ID NO 31
<211> LENGTH: 8
<212> TYPE: PRT
<213> ORGANISM: Artificial Sequence
<220> FEATURE:
<223> OTHER INFORMATION: synthetic

<400> SEQUENCE: 31

Gly Tyr Thr Phe Thr Ala Tyr Tyr
1               5

<210> SEQ ID NO 32
<211> LENGTH: 8
<212> TYPE: PRT
<213> ORGANISM: Artificial Sequence
<220> FEATURE:
<223> OTHER INFORMATION: synthetic

<400> SEQUENCE: 32

Met Asn Thr Asn Asn Gly Ala Thr
1               5

<210> SEQ ID NO 33
<211> LENGTH: 12
<212> TYPE: PRT
<213> ORGANISM: Artificial Sequence
<220> FEATURE:
<223> OTHER INFORMATION: synthetic

<400> SEQUENCE: 33

Ala Arg Gly Asp Ile Ser Gln Asp Phe Ala Asp Val
1               5                   10

<210> SEQ ID NO 34
<211> LENGTH: 8
<212> TYPE: PRT
<213> ORGANISM: Artificial Sequence
<220> FEATURE:
<223> OTHER INFORMATION: synthetic

<400> SEQUENCE: 34

Ser Gly Ser Ile Ala Ser Asn Tyr
1               5

<210> SEQ ID NO 35
<211> LENGTH: 3
<212> TYPE: PRT
<213> ORGANISM: Artificial Sequence
<220> FEATURE:
<223> OTHER INFORMATION: synthetic

<400> SEQUENCE: 35

Glu Asp Asn
1

<210> SEQ ID NO 36
<211> LENGTH: 10
<212> TYPE: PRT
<213> ORGANISM: Artificial Sequence
<220> FEATURE:
<223> OTHER INFORMATION: synthetic

<400> SEQUENCE: 36

Gln Ser Tyr Asp Asp Ile Asn His Trp Val
1               5                   10

<210> SEQ ID NO 37
<211> LENGTH: 119
<212> TYPE: PRT
<213> ORGANISM: Artificial Sequence
<220> FEATURE:
<223> OTHER INFORMATION: synthetic

<400> SEQUENCE: 37

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ala Tyr
            20                  25                  30

Tyr Leu His Trp Leu Arg Gln Ala Pro Gly Gln Gly Leu Glu Trp Met
        35                  40                  45

Gly Trp Met Asn Thr Asn Asn Gly Ala Thr Arg Tyr Ala Gln Lys Phe
    50                  55                  60

Gln Asp Arg Val Thr Met Thr Arg Asp Thr Ser Ile Asn Thr Ala Tyr
65                  70                  75                  80

Met Glu Met Ser Gly Leu Ser Ser Asp Asp Thr Ala Met Tyr Tyr Cys
                85                  90                  95

Ala Arg Gly Asp Ile Ser Gln Asp Phe Ala Asp Val Trp Gly Gln Gly
            100                 105                 110

Thr Leu Val Thr Val Ser Ser
        115

<210> SEQ ID NO 38
<211> LENGTH: 357
<212> TYPE: DNA
<213> ORGANISM: Artificial Sequence
<220> FEATURE:
<223> OTHER INFORMATION: synthetic

<400> SEQUENCE: 38
gaggtgcagc tggtgcagtc tggggctgag gtgaagaagc ctggggcctc agtgaaggtc    60
tcctgcaagg cttctggata caccttcacc gcctactatc tgcactggct gcgacaggcc   120

```
cctggacaag ggcttgagtg gatgggatgg atgaatacta acaatggtgc cacaaggtat    180
gcacagaaat tcaggacag  ggtcaccatg accagggaca cgtccattaa cacagcctac    240
atggagatga gcgggctgtc atctgacgac accgccatgt attactgtgc gcgcggtgat    300
atctctcagg acttcgctga tgtttggggt caaggtactc tggtgaccgt ctcctca      357
```

<210> SEQ ID NO 39
<211> LENGTH: 112
<212> TYPE: PRT
<213> ORGANISM: Artificial Sequence
<220> FEATURE:
<223> OTHER INFORMATION: synthetic

<400> SEQUENCE: 39

```
Asn Phe Met Leu Thr Gln Pro His Ser Val Ser Glu Ser Pro Gly Lys
1               5                   10                  15

Thr Val Thr Ile Ser Cys Thr Gly Ser Ser Gly Ser Ile Ala Ser Asn
            20                  25                  30

Tyr Val Gln Trp Tyr Gln Arg Pro Gly Ser Ala Pro Thr Ile Leu
        35                  40                  45

Ile Tyr Glu Asp Asn Lys Arg Pro Ser Gly Val Pro Asp Arg Phe Ser
50                  55                  60

Gly Ser Ile Asp Ser Ser Asn Ser Ala Ser Leu Thr Ile Ser Gly
65                  70                  75                  80

Leu Lys Thr Gly Asp Glu Ala Asp Tyr Tyr Cys Gln Ser Tyr Asp Asp
            85                  90                  95

Ile Asn His Trp Val Phe Gly Gly Thr Lys Leu Thr Val Leu Gly
            100                 105                 110
```

<210> SEQ ID NO 40
<211> LENGTH: 336
<212> TYPE: DNA
<213> ORGANISM: Artificial Sequence
<220> FEATURE:
<223> OTHER INFORMATION: synthetic

<400> SEQUENCE: 40

```
aattttatgc tgactcagcc ccactctgtg tcggagtctc cggggaagac ggtaaccatc     60
tcctgcaccg gcagcagtgg cagcattgcc agcaactatg tgcagtggta tcagcagcgc    120
ccgggcagtg cccccaccat tctgatctat gaggataaca aaagaccctc tggggtccct    180
gatcggttct ctggctccat cgacagctcc tccaactctg cctccctcac catctctgga    240
ctgaagactg gggacgaggc tgactactac tgtcagtctt atgatgacat caatcattgg    300
gtgttcggcg gagggaccaa gctgaccgtc ctaggt                              336
```

<210> SEQ ID NO 41
<211> LENGTH: 8
<212> TYPE: PRT
<213> ORGANISM: Artificial Sequence
<220> FEATURE:
<223> OTHER INFORMATION: synthetic

<400> SEQUENCE: 41

```
Gly Gly Ser Phe Ser Gly Tyr Tyr
1               5
```

<210> SEQ ID NO 42
<211> LENGTH: 7
<212> TYPE: PRT
<213> ORGANISM: Artificial Sequence

```
<220> FEATURE:
<223> OTHER INFORMATION: synthetic

<400> SEQUENCE: 42

Val Asn His Ser Gly Asn Thr
1               5

<210> SEQ ID NO 43
<211> LENGTH: 10
<212> TYPE: PRT
<213> ORGANISM: Artificial Sequence
<220> FEATURE:
<223> OTHER INFORMATION: synthetic

<400> SEQUENCE: 43

Ala Arg Tyr Phe Pro Pro Met Ile Asp Val
1               5                   10

<210> SEQ ID NO 44
<211> LENGTH: 8
<212> TYPE: PRT
<213> ORGANISM: Artificial Sequence
<220> FEATURE:
<223> OTHER INFORMATION: synthetic

<400> SEQUENCE: 44

Ser Ser Asn Ile Glu Asn Asn Tyr
1               5

<210> SEQ ID NO 45
<211> LENGTH: 3
<212> TYPE: PRT
<213> ORGANISM: Artificial Sequence
<220> FEATURE:
<223> OTHER INFORMATION: synthetic

<400> SEQUENCE: 45

Asp Asn Asn
1

<210> SEQ ID NO 46
<211> LENGTH: 11
<212> TYPE: PRT
<213> ORGANISM: Artificial Sequence
<220> FEATURE:
<223> OTHER INFORMATION: synthetic

<400> SEQUENCE: 46

Gly Thr Trp Asp Ser Ser Leu Ser Ala Tyr Val
1               5                   10

<210> SEQ ID NO 47
<211> LENGTH: 116
<212> TYPE: PRT
<213> ORGANISM: Artificial Sequence
<220> FEATURE:
<223> OTHER INFORMATION: synthetic

<400> SEQUENCE: 47

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Ser Pro Gly Lys Gly Leu Glu Trp Ile
        35                  40                  45
```

Gly Glu Val Asn His Ser Gly Asn Thr Asn Tyr Asn Pro Ser Leu Lys
            50                  55                  60

Ser Arg Val Thr Ile Ser Leu Asp Thr Ser Lys Asn Gln Phe Ser Leu
 65                  70                  75                  80

Lys Leu Asn Ser Val Thr Ala Ala Asp Thr Ala Val Tyr Tyr Cys Ala
                 85                  90                  95

Arg Tyr Phe Pro Pro Met Ile Asp Val Trp Gly Gln Gly Thr Leu Val
            100                 105                 110

Thr Val Ser Ser
        115

<210> SEQ ID NO 48
<211> LENGTH: 348
<212> TYPE: DNA
<213> ORGANISM: Artificial Sequence
<220> FEATURE:
<223> OTHER INFORMATION: synthetic

<400> SEQUENCE: 48
caggtgcagc tacagcagtg gggcgcagga ctgttgaaac cttcggagac cctgtccctc      60
acctgcgctg tctatggtgg gtccttcagc ggttactact ggagctggat ccgccagtcc     120
ccagggaagg gactggagtg gattggggaa gtcaatcata gtggcaacac caactacaac     180
ccgtccctca gagtcgagt caccattca ctagacacgt ccaagaacca gttctccctg       240
aaactgaact ctgtgaccgc cgccgacacg gccgtgtatt actgtgcgcg ctacttcccg     300
ccgatgatcg atgtttgggg tcaaggtact ctggtgaccg tctcctca                  348

<210> SEQ ID NO 49
<211> LENGTH: 111
<212> TYPE: PRT
<213> ORGANISM: Artificial Sequence
<220> FEATURE:
<223> OTHER INFORMATION: synthetic

<400> SEQUENCE: 49

Gln Ser Val Val Thr Gln Pro Pro Ser Val Ser Ala Ala Pro Gly Gln
  1               5                  10                  15

Lys Val Thr Ile Ser Cys Ser Gly Ser Ser Ser Asn Ile Glu Asn Asn
                 20                  25                  30

Tyr Val Ser Trp Tyr Gln Gln Leu Pro Gly Thr Ala Pro Lys Leu Leu
             35                  40                  45

Ile Tyr Asp Asn Asn Lys Arg Pro Ser Gly Ile Pro Asp Arg Phe Ser
 50                  55                  60

Gly Ser Lys Ser Gly Thr Ser Ala Thr Leu Gly Ile Thr Gly Leu Gln
 65                  70                  75                  80

Thr Gly Asp Glu Ala Asp Tyr Tyr Cys Gly Thr Trp Asp Ser Ser Leu
                 85                  90                  95

Ser Ala Tyr Val Phe Gly Thr Gly Thr Lys Val Thr Val Leu Gly
            100                 105                 110

<210> SEQ ID NO 50
<211> LENGTH: 333
<212> TYPE: DNA
<213> ORGANISM: Artificial Sequence
<220> FEATURE:
<223> OTHER INFORMATION: synthetic

<400> SEQUENCE: 50
cagtctgtcg tgacgcagcc gccctcagtg tctgcggccc caggacagaa ggtcaccatc      60

```
tcctgctctg gaagcagctc aacattgag aataattatg tatcatggta ccagcagctc    120
ccaggaacag ccccaaaact cctcatttat gacaataata agcgaccctc agggattcct    180
gaccgattct ctggctccaa gtctggcacg tcagccaccc tgggcatcac cggactccag    240
actggggacg aggccgatta ttactgcgga acatgggata gcagcctgag tgcctatgtc    300
ttcggaactg ggaccaaggt caccgtccta ggt                                 333
```

<210> SEQ ID NO 51
<211> LENGTH: 10
<212> TYPE: PRT
<213> ORGANISM: Artificial Sequence
<220> FEATURE:
<223> OTHER INFORMATION: synthetic

<400> SEQUENCE: 51

Gly Gly Ser Ile Ser Ser Ser Ser Tyr Tyr
1               5                   10

<210> SEQ ID NO 52
<211> LENGTH: 7
<212> TYPE: PRT
<213> ORGANISM: Artificial Sequence
<220> FEATURE:
<223> OTHER INFORMATION: synthetic

<400> SEQUENCE: 52

Ile Asn His Ser Gly Ser Thr
1               5

<210> SEQ ID NO 53
<211> LENGTH: 14
<212> TYPE: PRT
<213> ORGANISM: Artificial Sequence
<220> FEATURE:
<223> OTHER INFORMATION: synthetic

<400> SEQUENCE: 53

Ala Arg Tyr Ser His His Val Asp Ser Gly Gly Tyr Asp Val
1               5                   10

<210> SEQ ID NO 54
<211> LENGTH: 8
<212> TYPE: PRT
<213> ORGANISM: Artificial Sequence
<220> FEATURE:
<223> OTHER INFORMATION: synthetic

<400> SEQUENCE: 54

Ser Ser Asn Ile Gly Asn Asn Tyr
1               5

<210> SEQ ID NO 55
<211> LENGTH: 3
<212> TYPE: PRT
<213> ORGANISM: Artificial Sequence
<220> FEATURE:
<223> OTHER INFORMATION: synthetic

<400> SEQUENCE: 55

Asp Asn Asn
1

<210> SEQ ID NO 56
<211> LENGTH: 11

<212> TYPE: PRT
<213> ORGANISM: Artificial Sequence
<220> FEATURE:
<223> OTHER INFORMATION: synthetic

<400> SEQUENCE: 56

Gly Thr Trp Asp Ser Ser Leu Ser Ala Val Val
1               5                   10

<210> SEQ ID NO 57
<211> LENGTH: 122
<212> TYPE: PRT
<213> ORGANISM: Artificial Sequence
<220> FEATURE:
<223> OTHER INFORMATION: synthetic

<400> SEQUENCE: 57

Gln Leu Gln Leu Gln Glu Ser Gly Pro Gly Leu Val Lys Pro Ser Glu
1               5                   10                  15

Thr Leu Ser Leu Ser Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Glu Ile Asn His Ser Gly Ser Thr Asn Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Tyr Ser His His Val Asp Ser Gly Tyr Asp Val Trp
            100                 105                 110

Gly Gln Gly Thr Leu Val Thr Val Ser Ser
        115                 120

<210> SEQ ID NO 58
<211> LENGTH: 366
<212> TYPE: DNA
<213> ORGANISM: Artificial Sequence
<220> FEATURE:
<223> OTHER INFORMATION: synthetic

<400> SEQUENCE: 58
cagctgcagc tgcaggagtc gggcccagga ctggtgaagc cttcggagac cctgtccctc      60
agttgcactg tctctggtgg ctccatcagc agtagtagtt actactgggg ctggatccgc     120
cagcccccag ggaagggct ggagtggatt ggggaaatca atcatagtgg aagcaccaac      180
tacaacccgt ccctcaagag tcgagtcacc atatcagtag acacgtccaa gaaccagttc     240
tccctgaagc tgagttctgt gaccgccgcg gacacggccg tgtattactg tgcgcgctac     300
tctcatcatg ttgactctgg tggttacgat gtttggggtc aaggtactct ggtgaccgtc     360
tcctca                                                                366

<210> SEQ ID NO 59
<211> LENGTH: 111
<212> TYPE: PRT
<213> ORGANISM: Artificial Sequence
<220> FEATURE:
<223> OTHER INFORMATION: synthetic

<400> SEQUENCE: 59

Gln Ser Val Val Thr Gln Pro Pro Ser Val Ser Ala Ala Pro Gly Gln

```
              1               5                  10                  15
Lys Val Thr Ile Ser Cys Ser Gly Ser Ser Asn Ile Gly Asn Asn
                          20                  25                  30

Tyr Val Ser Trp Tyr Gln Gln Leu Pro Arg Thr Ala Pro Arg Leu Leu
                35                  40                  45

Ile Tyr Asp Asn Asn Lys Arg Pro Ser Gly Ile Pro Asp Arg Phe Ser
        50                  55                  60

Ala Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                    85                  90                  95

Ser Ala Val Val Phe Gly Gly Gly Thr Lys Leu Thr Val Leu Gly
                100                 105                 110
```

<210> SEQ ID NO 60
<211> LENGTH: 333
<212> TYPE: DNA
<213> ORGANISM: Artificial Sequence
<220> FEATURE:
<223> OTHER INFORMATION: synthetic

<400> SEQUENCE: 60

```
cagtctgtcg tgacgcagcc gccctcagtg tctgcggccc caggacagaa ggtcaccatc      60
tcctgctctg gaagcagctc caacattggg aataattatg tatcctgta ccagcagctc     120 ccaagaacag ccccccagact cctcatttat gacaataata agcgaccctc agggattcct    180
gaccgattct ctgcctccaa gtctggcacg tcagccaccc tgggcatcac cggactccag    240
actggggacg aggccgatta ttactgcgga acatgggata gcagcctgag tgctgtggta    300
ttcggcggag ggaccaagct gaccgtccta ggt                                  333
```

<210> SEQ ID NO 61
<211> LENGTH: 8
<212> TYPE: PRT
<213> ORGANISM: Artificial Sequence
<220> FEATURE:
<223> OTHER INFORMATION: synthetic

<400> SEQUENCE: 61

```
Gly Gly Thr Phe Ser Ser Tyr Gly
1               5
```

<210> SEQ ID NO 62
<211> LENGTH: 8
<212> TYPE: PRT
<213> ORGANISM: Artificial Sequence
<220> FEATURE:
<223> OTHER INFORMATION: synthetic

<400> SEQUENCE: 62

```
Ile Ile Pro Ile Phe Gly Thr Pro
1               5
```

<210> SEQ ID NO 63
<211> LENGTH: 10
<212> TYPE: PRT
<213> ORGANISM: Artificial Sequence
<220> FEATURE:
<223> OTHER INFORMATION: synthetic

<400> SEQUENCE: 63

```
Ala Arg Ser Tyr Tyr Gly Tyr Phe Asp Gly
```

```
<210> SEQ ID NO 64
<211> LENGTH: 6
<212> TYPE: PRT
<213> ORGANISM: Artificial Sequence
<220> FEATURE:
<223> OTHER INFORMATION: synthetic

<400> SEQUENCE: 64

Gln Asp Ile Ser Asn Tyr
1               5

<210> SEQ ID NO 65
<211> LENGTH: 3
<212> TYPE: PRT
<213> ORGANISM: Artificial Sequence
<220> FEATURE:
<223> OTHER INFORMATION: synthetic

<400> SEQUENCE: 65

Asp Ala Ser
1

<210> SEQ ID NO 66
<211> LENGTH: 9
<212> TYPE: PRT
<213> ORGANISM: Artificial Sequence
<220> FEATURE:
<223> OTHER INFORMATION: synthetic

<400> SEQUENCE: 66

Gln Gln Tyr Lys Ser Tyr Pro Leu Thr
1               5

<210> SEQ ID NO 67
<211> LENGTH: 117
<212> TYPE: PRT
<213> ORGANISM: Artificial Sequence
<220> FEATURE:
<223> OTHER INFORMATION: synthetic

<400> SEQUENCE: 67

Glu Val Gln Leu Val Glu Ser Gly Ala Glu Val Lys Glu Pro Gly Ser
1               5                   10                  15

Ser Val Lys Val Ser Cys Lys Ala Ser Gly Gly Thr Phe Ser Ser Tyr
            20                  25                  30

Gly Ile Ser Trp Ile Arg Gln Ala Pro Gly Gln Gly Leu Glu Trp Met
        35                  40                  45

Gly Glu Ile Ile Pro Ile Phe Gly Thr Pro Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Val Glu Leu Ser Ser Leu Arg Ser Asp Asp Thr Ala Val Tyr Tyr Cys
                85                  90                  95

Ala Arg Ser Tyr Tyr Gly Tyr Phe Asp Gly Trp Gly Gln Gly Thr Leu
                100                 105                 110

Val Thr Val Ser Ser
            115

<210> SEQ ID NO 68
<211> LENGTH: 351
<212> TYPE: DNA
```

<213> ORGANISM: Artificial Sequence
<220> FEATURE:
<223> OTHER INFORMATION: synthetic

<400> SEQUENCE: 68

```
gaggtgcagc tggtggagtc tggggctgag gtgaaggagc ctgggtcctc ggtgaaggtc    60
tcctgcaagg cttctggagg caccttcagc agctatggta tcagctggat tcgacaggcc   120
cctggacaag ggcttgagtg gatgggagag atcatcccta tctttggtac accaaactac   180
gcgcagaagt tccagggcag agtcacgatt accgcggacg aatccacgag cacagcctac   240
gtggagctga gcagcctgag atctgacgac acggccgtat attactgtgc gcgctcttac   300
tacggttact tcgatggttg gggtcaaggt actctggtga ccgtctcctc a            351
```

<210> SEQ ID NO 69
<211> LENGTH: 108
<212> TYPE: PRT
<213> ORGANISM: Artificial Sequence
<220> FEATURE:
<223> OTHER INFORMATION: synthetic

<400> SEQUENCE: 69

```
Asp Ile Gln Met Thr Gln Ser Pro Ser Ser Leu Ser Ala Ser Val Gly
1               5                   10                  15
Asp Arg Val Thr Ile Thr Cys Gln Ala Ser Gln Asp Ile Ser Asn Tyr
            20                  25                  30
Leu Asn Trp Tyr Gln Gln Lys Pro Gly Lys Ala Pro Lys Leu Leu Ile
        35                  40                  45
Tyr Asp Ala Ser Asn Leu Glu Thr Gly Val Pro Ser Arg Phe Ser Gly
    50                  55                  60
Ser Gly Ser Gly Thr Asp Phe Thr Phe Thr Ile Ser Ser Leu Gln Pro
65                  70                  75                  80
Asp Asp Phe Ala Thr Tyr Tyr Cys Gln Gln Tyr Lys Ser Tyr Pro Leu
                85                  90                  95
Thr Phe Gly Gly Gly Thr Lys Val Glu Ile Lys Arg
            100                 105
```

<210> SEQ ID NO 70
<211> LENGTH: 324
<212> TYPE: DNA
<213> ORGANISM: Artificial Sequence
<220> FEATURE:
<223> OTHER INFORMATION: synthetic

<400> SEQUENCE: 70

```
gacatccaga tgacccagtc tccatcctcc ctgtctgcat ctgtaggaga cagagtcacc    60
atcacttgcc aggcgagtca ggacattagc aactatttaa attggtatca gcagaaacca   120
gggaaagccc ctaagctcct gatctacgat gcatccaatt tggaaacagg ggtcccatca   180
aggttcagtg aagtggatc tgggacagat tttactttca ccatcagcag cctgcagcct   240
gatgattttg caacttatta ctgccaacag tataagagtt acccgctcac tttcggcgga   300
gggaccaagg tggagatcaa acgt                                          324
```

<210> SEQ ID NO 71
<211> LENGTH: 8
<212> TYPE: PRT
<213> ORGANISM: Artificial Sequence
<220> FEATURE:
<223> OTHER INFORMATION: synthetic

<400> SEQUENCE: 71

Gly Tyr Thr Phe Thr Ser Tyr Tyr
1               5

<210> SEQ ID NO 72
<211> LENGTH: 8
<212> TYPE: PRT
<213> ORGANISM: Artificial Sequence
<220> FEATURE:
<223> OTHER INFORMATION: synthetic

<400> SEQUENCE: 72

Ile Asn Pro Ser Gly Gly Ser Thr
1               5

<210> SEQ ID NO 73
<211> LENGTH: 11
<212> TYPE: PRT
<213> ORGANISM: Artificial Sequence
<220> FEATURE:
<223> OTHER INFORMATION: synthetic

<400> SEQUENCE: 73

Ala Arg Ser Met Tyr Gln Tyr Phe Leu Asp Ser
1               5                   10

<210> SEQ ID NO 74
<211> LENGTH: 9
<212> TYPE: PRT
<213> ORGANISM: Artificial Sequence
<220> FEATURE:
<223> OTHER INFORMATION: syntetic

<400> SEQUENCE: 74

Ser Ser Asn Ile Gly Ala Gly Tyr Asp
1               5

<210> SEQ ID NO 75
<211> LENGTH: 3
<212> TYPE: PRT
<213> ORGANISM: Artificial Sequence
<220> FEATURE:
<223> OTHER INFORMATION: synthetic

<400> SEQUENCE: 75

Gly Asn Ile
1

<210> SEQ ID NO 76
<211> LENGTH: 9
<212> TYPE: PRT
<213> ORGANISM: Artificial Sequence
<220> FEATURE:
<223> OTHER INFORMATION: synthetic

<400> SEQUENCE: 76

Gln Ser Tyr Asp Ser Asn Leu Ser Gly
1               5

<210> SEQ ID NO 77
<211> LENGTH: 118
<212> TYPE: PRT
<213> ORGANISM: Artificial Sequence
<220> FEATURE:
<223> OTHER INFORMATION: synthetic

<400> SEQUENCE: 77

Glu Val Gln Leu Val Glu Ser Gly Ala Glu Val Lys Pro Gly Ala
1               5                   10                  15

Ser Val Lys Ile Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Met Tyr Gln Tyr Phe Leu Asp Ser Trp Gly Gln Gly Thr
            100                 105                 110

Leu Val Thr Val Ser Ser
            115

<210> SEQ ID NO 78
<211> LENGTH: 354
<212> TYPE: DNA
<213> ORGANISM: Artificial Sequence
<220> FEATURE:
<223> OTHER INFORMATION: syntetic

<400> SEQUENCE: 78
gaggtgcagc tggtggagtc cgggggctgag gtgaagaagc ctggggcctc agtaaaaatt        60
tcctgcaagg catctggata caccttcacc agctactata tgcactgggt gcgacaggcc       120
cctggacaag ggcttgagtg gatgggaata atcaacccta gtggtggtag cacaagctac       180
gcacagaagt tccagggcag agtcaccatg accaggggaca cgtccacgag cacagtctac       240
atggagctga gcagcctgag atctgaggac acggccgtat attactgtgc gcgctctatg       300
taccagtact tcctggattc ttggggtcaa ggtactctgg tgaccgtctc ctca             354

<210> SEQ ID NO 79
<211> LENGTH: 112
<212> TYPE: PRT
<213> ORGANISM: Artificial Sequence
<220> FEATURE:
<223> OTHER INFORMATION: synthetic

<400> SEQUENCE: 79

Gln Ser Val Val Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ile Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Asn
                85                  90                  95

Leu Ser Gly Tyr Val Phe Ala Thr Gly Thr Lys Val Thr Val Leu Gly
            100                 105                 110

<210> SEQ ID NO 80
<211> LENGTH: 336
<212> TYPE: DNA
<213> ORGANISM: Artificial Sequence
<220> FEATURE:
<223> OTHER INFORMATION: synthetic

<400> SEQUENCE: 80

```
cagtctgtcg tgacgcagcc gccctcagtg tctggggccc cagggcagag ggtcaccatc      60
tcctgcactg ggagcagctc caacatcggg gcaggttatg atgtacactg gtaccagcaa     120
cttccaggaa cagcccccaa actcctcatc tatggtaaca tcaatcggcc ctcaggggtc     180
cctgaccgat tctctggctc caagtctggc acctcagcct ccctggccat cactgggctc     240
caggctgagg atgaggctga ttattactgc cagtcctatg acagcaacct gagtggttat     300
gtcttcgcaa ctgggaccaa ggtcaccgtc ctaggt                               336
```

<210> SEQ ID NO 81
<211> LENGTH: 251
<212> TYPE: PRT
<213> ORGANISM: Artificial Sequence
<220> FEATURE:
<223> OTHER INFORMATION: synthetic

<400> SEQUENCE: 81

Gln Ser Val Leu Thr Gln Pro Pro Ser Val Gly Ala Pro Gly Gln
1               5                   10                  15

Arg Val Thr Ile Ser Cys Thr Gly Ser Ser Asn Ile Gly Ala Gly
                20                  25                  30

Tyr Asp Val His Trp Tyr Gln Gln Leu Pro Gly Thr Ala Pro Lys Leu
                35                  40                  45

Leu Ile Tyr Gly Asn Ser Asn Arg Pro Ser Gly Val Pro Asp Arg Phe
50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Tyr Val Phe Gly Thr Gly Thr Lys Val Thr Val Leu Gly
                100                 105                 110

Ser Arg Gly Gly Gly Gly Ser Gly Gly Gly Ser Gly Gly Gly Gly
                115                 120                 125

Ser Leu Glu Met Ala Gln Val Gln Leu Val Gln Ser Gly Ala Glu Val
130                 135                 140

Lys Lys Pro Gly Ser Ser Val Lys Val Ser Cys Lys Ala Ser Gly Gly
145                 150                 155                 160

Thr Phe Ser Ser Tyr Ala Ile Ser Trp Val Arg Gln Ala Pro Gly Gln
                165                 170                 175

Gly Leu Glu Trp Met Gly Gly Ile Ile Pro Ile Phe Gly Lys Gly Asn
                180                 185                 190

Tyr Pro Gln Lys Phe Gln Gly Arg Val Thr Ile Thr Ala Asp Glu Ser
                195                 200                 205

Thr Gly Thr Ala Tyr Met Glu Leu Ser Ser Leu Arg Ser Glu Asp Thr
                210                 215                 220

Ala Val Tyr Tyr Cys Ala Arg His Ile Pro Thr Phe Ser Phe Asp Tyr
225                 230                 235                 240

Trp Gly Gln Gly Thr Leu Val Thr Val Ser Ser
                245                 250

<210> SEQ ID NO 82
<211> LENGTH: 249
<212> TYPE: PRT
<213> ORGANISM: Artificial Sequence
<220> FEATURE:
<223> OTHER INFORMATION: synthetic

<400> SEQUENCE: 82

```
Gln Ser Val Leu Thr Gln Pro Pro Ser Val Gly Ala Pro Gly Gln
1               5                   10                  15

Arg Val Thr Ile Ser Cys Thr Gly Ser Ser Asn Ile Gly Ala Gly
                20                  25                  30

Tyr Asp Val His Trp Tyr Gln Gln Leu Pro Gly Thr Ala Pro Lys Leu
            35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Ser Val Phe Gly Thr Gly Thr Lys Val Thr Val Leu Gly
            100                 105                 110

Ser Arg Gly Gly Gly Gly Ser Gly Gly Gly Ser Gly Gly Gly Gly
        115                 120                 125

Ser Leu Glu Met Ala Val Gln Leu Val Gln Ser Gly Ala Glu Val Lys
130                 135                 140

Lys Pro Gly Ser Ser Val Lys Val Ser Cys Lys Ala Ser Gly Gly Thr
145                 150                 155                 160

Phe Ser Ser Tyr Thr Ile Asn Trp Val Arg Gln Ala Pro Gly Gln Gly
                165                 170                 175

Leu Glu Trp Met Gly Gly Phe Ile Pro Ile Ser Gly Thr Val Asn Tyr
            180                 185                 190

Ala Gln Lys Phe Gln Gly Arg Val Thr Ile Thr Ala Asp Glu Ser Thr
        195                 200                 205

Ser Thr Ala Tyr Met Glu Leu Ser Ser Leu Arg Ser Glu Asp Thr Ala
    210                 215                 220

Val Tyr Tyr Cys Ala Arg Pro Leu Asp Trp Thr Glu Asp Ile Trp Gly
225                 230                 235                 240

Gln Gly Thr Leu Val Thr Val Ser Ser
                245
```

<210> SEQ ID NO 83
<211> LENGTH: 252
<212> TYPE: PRT
<213> ORGANISM: Artificial Sequence
<220> FEATURE:
<223> OTHER INFORMATION: synthetic

<400> SEQUENCE: 83

```
Asn Phe Met Leu Thr Gln Pro His Ser Val Ser Glu Ser Pro Gly Lys
1               5                   10                  15

Thr Val Thr Ile Ser Cys Thr Gly Ser Ser Gly Ser Ile Ala Ser Asn
                20                  25                  30

Tyr Val Gln Trp Tyr Gln Gln Arg Pro Gly Ser Ala Pro Thr Ile Leu
            35                  40                  45

Ile Tyr Glu Asp Asn Lys Arg Pro Ser Gly Val Pro Asp Arg Phe Ser
    50                  55                  60
```

Gly Ser Ile Asp Ser Ser Asn Ser Ala Ser Leu Thr Ile Ser Gly
65                  70                  75                  80

Leu Lys Thr Gly Asp Glu Ala Asp Tyr Tyr Cys Gln Ser Tyr Asp Asp
                85                  90                  95

Ile Asn His Trp Val Phe Gly Gly Gly Thr Lys Leu Thr Val Leu Gly
            100                 105                 110

Ser Arg Gly Gly Gly Gly Ser Gly Gly Gly Gly Ser Gly Gly Gly Gly
        115                 120                 125

Ser Leu Glu Met Ala Glu Val Gln Leu Val Gln Ser Gly Ala Glu Val
130                 135                 140

Lys Lys Pro Gly Ala Ser Val Lys Val Ser Cys Lys Ala Ser Gly Tyr
145                 150                 155                 160

Thr Phe Thr Ala Tyr Tyr Leu His Trp Leu Arg Gln Ala Pro Gly Gln
                165                 170                 175

Gly Leu Glu Trp Met Gly Trp Met Asn Thr Asn Asn Gly Ala Thr Arg
            180                 185                 190

Tyr Ala Gln Lys Phe Gln Asp Arg Val Thr Met Thr Arg Asp Thr Ser
        195                 200                 205

Ile Asn Thr Ala Tyr Met Glu Met Ser Gly Leu Ser Ser Asp Asp Thr
210                 215                 220

Ala Met Tyr Tyr Cys Ala Arg Gly Asp Ile Ser Gln Asp Phe Ala Asp
225                 230                 235                 240

Val Trp Gly Gln Gly Thr Leu Val Thr Val Ser Ser
                245                 250

<210> SEQ ID NO 84
<211> LENGTH: 252
<212> TYPE: PRT
<213> ORGANISM: Artificial Sequence
<220> FEATURE:
<223> OTHER INFORMATION: synthetic

<400> SEQUENCE: 84

Asn Phe Met Leu Thr Gln Pro His Ser Val Ser Glu Ser Pro Gly Lys
1               5                   10                  15

Thr Val Thr Ile Ser Cys Thr Gly Ser Ser Gly Ser Ile Ala Ser Asn
            20                  25                  30

Tyr Val Gln Trp Tyr Gln Gln Arg Pro Gly Ser Ala Pro Thr Ile Leu
        35                  40                  45

Ile Tyr Glu Asp Asn Lys Arg Pro Ser Gly Val Pro Asp Arg Phe Ser
50                  55                  60

Gly Ser Ile Asp Ser Ser Asn Ser Ala Ser Leu Thr Ile Ser Gly
65                  70                  75                  80

Leu Lys Thr Gly Asp Glu Ala Asp Tyr Tyr Cys Gln Ser Tyr Asp Asp
                85                  90                  95

Ile Asn His Trp Val Phe Gly Gly Gly Thr Lys Leu Thr Val Leu Gly
            100                 105                 110

Ser Arg Gly Gly Gly Gly Ser Gly Gly Gly Gly Ser Gly Gly Gly Gly
        115                 120                 125

Ser Leu Glu Met Ala Glu Val Gln Leu Val Gln Ser Gly Ala Glu Val
130                 135                 140

Lys Lys Pro Gly Ala Ser Val Lys Val Ser Cys Lys Ala Ser Gly Tyr
145                 150                 155                 160

Thr Phe Thr Ala Tyr Tyr Leu His Trp Leu Arg Gln Ala Pro Gly Gln
                165                 170                 175

Gly Leu Glu Trp Met Gly Trp Met Asn Thr Asn Asn Gly Ala Thr Arg
            180                 185                 190

Tyr Ala Gln Lys Phe Gln Asp Arg Val Thr Met Thr Arg Asp Thr Ser
            195                 200                 205

Ile Asn Thr Ala Tyr Met Glu Met Ser Gly Leu Ser Ser Asp Asp Thr
            210                 215                 220

Ala Met Tyr Tyr Cys Ala Arg Gly Asp Ile Ser Gln Asp Phe Ala Asp
225                 230                 235                 240

Val Trp Gly Gln Gly Thr Leu Val Thr Val Ser Ser
                245                 250

<210> SEQ ID NO 85
<211> LENGTH: 248
<212> TYPE: PRT
<213> ORGANISM: Artificial Sequence
<220> FEATURE:
<223> OTHER INFORMATION: syntetic

<400> SEQUENCE: 85

Gln Ser Val Val Thr Gln Pro Pro Ser Val Ser Ala Ala Pro Gly Gln
1               5                   10                  15

Lys Val Thr Ile Ser Cys Ser Gly Ser Ser Ser Asn Ile Glu Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Tyr Val Phe Gly Thr Gly Thr Lys Val Thr Val Leu Gly Ser
            100                 105                 110

Arg Gly Gly Gly Gly Ser Gly Gly Gly Ser Gly Gly Gly Gly Ser
            115                 120                 125

Leu Glu Met Ala Gln Val Gln Leu Gln Gln Trp Gly Ala Gly Leu Leu
            130                 135                 140

Lys Pro Ser Glu Thr Leu Ser Leu Thr Cys Ala Val Tyr Gly Gly Ser
145                 150                 155                 160

Phe Ser Gly Tyr Tyr Trp Ser Trp Ile Arg Gln Ser Pro Gly Lys Gly
                165                 170                 175

Leu Glu Trp Ile Gly Glu Val Asn His Ser Gly Asn Thr Asn Tyr Asn
            180                 185                 190

Pro Ser Leu Lys Ser Arg Val Thr Ile Ser Leu Asp Thr Ser Lys Asn
            195                 200                 205

Gln Phe Ser Leu Lys Leu Asn Ser Val Thr Ala Ala Asp Thr Ala Val
            210                 215                 220

Tyr Tyr Cys Ala Arg Tyr Phe Pro Pro Met Ile Asp Val Trp Gly Gln
225                 230                 235                 240

Gly Thr Leu Val Thr Val Ser Ser
                245

<210> SEQ ID NO 86
<211> LENGTH: 254
<212> TYPE: PRT
<213> ORGANISM: Artificial Sequence

```
<220> FEATURE:
<223> OTHER INFORMATION: synthetic

<400> SEQUENCE: 86

Gln Ser Val Val Thr Gln Pro Pro Ser Val Ser Ala Ala Pro Gly Gln
1               5                   10                  15

Lys Val Thr Ile Ser Cys Ser Gly Ser Ser Asn Ile Gly Asn Asn
            20                  25                  30

Tyr Val Ser Trp Tyr Gln Gln Leu Pro Arg Thr Ala Pro Arg Leu Leu
            35                  40                  45

Ile Tyr Asp Asn Asn Lys Arg Pro Ser Gly Ile Pro Asp Arg Phe Ser
        50                  55                  60

Ala Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Val Val Phe Gly Gly Gly Thr Lys Leu Thr Val Leu Gly Ser
            100                 105                 110

Arg Gly Gly Gly Ser Gly Gly Gly Ser Gly Gly Gly Gly Ser
            115                 120                 125

Leu Glu Met Ala Gln Leu Gln Leu Gln Glu Ser Gly Pro Gly Leu Val
            130                 135                 140

Lys Pro Ser Glu Thr Leu Ser Leu Ser Cys Thr Val Ser Gly Gly Ser
145                 150                 155                 160

Ile Ser Ser Ser Ser Tyr Tyr Trp Gly Trp Ile Arg Gln Pro Pro Gly
                165                 170                 175

Lys Gly Leu Glu Trp Ile Gly Glu Ile Asn His Ser Gly Ser Thr Asn
            180                 185                 190

Tyr Asn Pro Ser Leu Lys Ser Arg Val Thr Ile Ser Val Asp Thr Ser
        195                 200                 205

Lys Asn Gln Phe Ser Leu Lys Leu Ser Ser Val Thr Ala Ala Asp Thr
    210                 215                 220

Ala Val Tyr Tyr Cys Ala Arg Tyr Ser His His Val Asp Ser Gly Gly
225                 230                 235                 240

Tyr Asp Val Trp Gly Gln Gly Thr Leu Val Thr Val Ser Ser
            245                 250

<210> SEQ ID NO 87
<211> LENGTH: 246
<212> TYPE: PRT
<213> ORGANISM: Artificial Sequence
<220> FEATURE:
<223> OTHER INFORMATION: synthetic

<400> SEQUENCE: 87

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
            35                  40                  45

Tyr Asp Ala Ser Asn Leu Glu Thr Gly Val Pro Ser Arg Phe Ser Gly
        50                  55                  60

Ser Gly Ser Gly Thr Asp Phe Thr Phe Thr Ile Ser Ser Leu Gln Pro
65                  70                  75                  80

Asp Asp Phe Ala Thr Tyr Tyr Cys Gln Gln Tyr Lys Ser Tyr Pro Leu
```

```
                        85                  90                  95
Thr Phe Gly Gly Gly Thr Lys Val Glu Ile Lys Arg Ser Arg Gly Gly
                100                 105                 110

Gly Gly Ser Gly Gly Gly Gly Ser Gly Gly Gly Ser Leu Glu Met
            115                 120                 125

Ala Glu Val Gln Leu Val Glu Ser Gly Ala Glu Val Lys Glu Pro Gly
            130                 135                 140

Ser Ser Val Lys Val Ser Cys Lys Ala Ser Gly Thr Phe Ser Ser
145                 150                 155                 160

Tyr Gly Ile Ser Trp Ile Arg Gln Ala Pro Gly Gln Gly Leu Glu Trp
                165                 170                 175

Met Gly Glu Ile Ile Pro Ile Phe Gly Thr Pro Asn Tyr Ala Gln Lys
            180                 185                 190

Phe Gln Gly Arg Val Thr Ile Thr Ala Asp Glu Ser Thr Ser Thr Ala
            195                 200                 205

Tyr Val Glu Leu Ser Ser Leu Arg Ser Asp Asp Thr Ala Val Tyr Tyr
            210                 215                 220

Cys Ala Arg Ser Tyr Tyr Gly Tyr Phe Asp Gly Trp Gly Gln Gly Thr
225                 230                 235                 240

Leu Val Thr Val Ser Ser
                245

<210> SEQ ID NO 88
<211> LENGTH: 251
<212> TYPE: PRT
<213> ORGANISM: Artificial Sequence
<220> FEATURE:
<223> OTHER INFORMATION: synthetic

<400> SEQUENCE: 88

Gln Ser Val Val Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ile Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Asn
                85                  90                  95

Leu Ser Gly Tyr Val Phe Ala Thr Gly Thr Lys Val Thr Val Leu Gly
            100                 105                 110

Ser Arg Gly Gly Gly Gly Ser Gly Gly Gly Ser Gly Gly Gly Gly
            115                 120                 125

Ser Leu Glu Met Ala Glu Val Gln Leu Val Glu Ser Gly Ala Glu Val
            130                 135                 140

Lys Lys Pro Gly Ala Ser Val Lys Ile Ser Cys Lys Ala Ser Gly Tyr
145                 150                 155                 160

Thr Phe Thr Ser Tyr Tyr Met His Trp Val Arg Gln Ala Pro Gly Gln
                165                 170                 175

Gly Leu Glu Trp Met Gly Ile Ile Asn Pro Ser Gly Gly Ser Thr Ser
            180                 185                 190

Tyr Ala Gln Lys Phe Gln Gly Arg Val Thr Met Thr Arg Asp Thr Ser
```

195                 200                 205
Thr Ser Thr Val Tyr Met Glu Leu Ser Ser Leu Arg Ser Glu Asp Thr
            210                 215                 220
Ala Val Tyr Tyr Cys Ala Arg Ser Met Tyr Gln Tyr Phe Leu Asp Ser
225                 230                 235                 240
Trp Gly Gln Gly Thr Leu Val Thr Val Ser Ser
                245                 250

<210> SEQ ID NO 89
<211> LENGTH: 740
<212> TYPE: DNA
<213> ORGANISM: Artificial Sequence
<220> FEATURE:
<223> OTHER INFORMATION: synthetic

<400> SEQUENCE: 89

```
cagtctgtgt tgacgcagcc gccctcagtg tctggggccc cagggcagag ggtcaccatc      60
tcctgcactg ggagcagctc aacatcggg gcaggttatg atgtacactg gtaccagcag     120
cttccaggaa cagcccccaa actcctcatc tatggtaaca gcaatcggcc ctcagggtc     180
cctgaccgat tctctggctc caagtctggc acctcagcct ccctggccat cactgggctc     240
caggctgagg atgaggctga ttattactgc cagtcctatg acagcagcct gagtggttat     300
gtcttcggaa ctgggaccaa ggtcaccgtc ctaggtctag aggtggtggt ggtagcggcg     360
gcggcggctc tggtggtggt ggatcccagg tgcagctggt gcagtctggg gctgaggtga     420
agaagcctgg gtcctcggtg aaggtctcct gcaaggcttc tggaggcacc ttcagcagct     480
atgctatcag ctgggtgcga caggcccctg gacaagggct tgagtggatg ggaggtatca     540
tccctatctt tggtaaagga aactacccac agaagttcca gggcagagtc acgattaccg     600
cggacgaatc tacgggcaca gcctacatgg agctgagcag cctgagatct gaggacacgg     660
ccgtgtatta ctgtgcgcgc catatcccga ctttctcttt cgattactgg ggtcaaggta     720
ctctggtgac cgtctcctca                                                 740
```

<210> SEQ ID NO 90
<211> LENGTH: 737
<212> TYPE: DNA
<213> ORGANISM: Artificial Sequence
<220> FEATURE:
<223> OTHER INFORMATION: synthetic

<400> SEQUENCE: 90

```
cagtctgtgt tgacgcagcc gccctcagtg tctggggccc cagggcagag ggtcaccatc      60
tcctgcactg ggagcagctc aacatcggg gcaggttatg atgtacactg gtaccagcag     120
cttccaggaa cagcccccaa actcctcatc tatggtaaca gcaatcggcc ctcagggtc     180
cctgaccgat tctctggctc caagtctggc acctcagcct ccctggccat cactgggctc     240
caggctgagg atgaggctga ttattactgc cagtcctatg acagcagcct gagtggttca     300
gtcttcggaa ctgggaccaa ggtcaccgtc ctaggtctag aggtggtggt ggtagcggcg     360
gcggcggctc tggtggtggt ggatcccagg tgcagctggt gcagtctggg gctgaggtga     420
agaagcctgg gtcctcggtg aaggtctcct gcaaggcttc tggaggcacc ttcagcagct     480
atactatcaa ctgggtgcga caggcccctg gacaagggct tgagtggatg ggagggttca     540
tccctatctc tggtacagta aactacgcac agaagttcca gggcagagtc acgattaccg     600
cggacgaatc cacgagcaca gcctacatgg aactgagcag cctgagatct gaggacactg     660
```

```
ccgtgtatta ctgtgcgcgc ccgctggact ggactgaaga tatctggggt caaggtactc    720
tggtgaccgt ctcctca                                                    737

<210> SEQ ID NO 91
<211> LENGTH: 743
<212> TYPE: DNA
<213> ORGANISM: Artificial Sequence
<220> FEATURE:
<223> OTHER INFORMATION: synthetic

<400> SEQUENCE: 91
aattttatgc tgactcagcc ccactctgtg tcggagtctc cggggaagac ggtaaccatc     60
tcctgcaccg gcagcagtgg cagcattgcc agcaactatg tgcagtggta tcagcagcgc    120
ccgggcagtg cccccaccat tctgatctat gaggataaca aaagaccctc tggggtccct    180
gatcggttct ctggctccat cgacagctcc tccaactctg cctccctcac catctctgga    240
ctgaagactg gggacgaggc tgactactac tgtcagtctt atgatgacat caatcattgg    300
gtgttcggcg agggaccaa gctgaccgtc ctaggtctag aggtggtggt ggtagcggcg    360
gcggcggctc tggtggtggt ggatccgagg tgcagctggt gcagtctggg gctgaggtga    420
agaagcctgg ggcctcagtg aaggtctcct gcaaggcttc tggatacacc ttcaccgcct    480
actatctgca ctggctgcga caggcccctg gacaagggct tgagtggatg ggatggatga    540
atactaacaa tggtgccaca aggtatgcac agaaatttca ggacagggtc accatgacca    600
gggacacgtc cattaacaca gcctacatgg agatgagcgg gctgtcatct gacgacaccg    660
ccatgtatta ctgtgcgcgc ggtgatatct ctcaggactt cgctgatgtt tggggtcaag    720
gtactctggt gaccgtctcc tca                                            743

<210> SEQ ID NO 92
<211> LENGTH: 743
<212> TYPE: DNA
<213> ORGANISM: Artificial Sequence
<220> FEATURE:
<223> OTHER INFORMATION: synthetic

<400> SEQUENCE: 92
aattttatgc tgactcagcc ccactctgtg tcggagtctc cggggaagac ggtaaccatc     60
tcctgcaccg gcagcagtgg cagcattgcc agcaactatg tgcagtggta tcagcagcgc    120
ccgggcagtg cccccaccat tctgatctat gaggataaca aaagaccctc tggggtccct    180
gatcggttct ctggctccat cgacagctcc tccaactctg cctccctcac catctctgga    240
ctgaagactg gggacgaggc tgactactac tgtcagtctt atgatgacat caatcattgg    300
gtgttcggcg agggaccaa gctgaccgtc ctaggtctag aggtggtggt ggtagcggcg    360
gcggcggctc tggtggtggt ggatccgagg tgcagctggt gcagtctggg gctgaggtga    420
agaagcctgg ggcctcagtg aaggtctcct gcaaggcttc tggatacacc ttcaccgcct    480
actatctgca ctggctgcga caggcccctg gacaagggct tgagtggatg ggatggatga    540
atactaacaa tggtgccaca aggtatgcac agaaatttca ggacagggtc accatgacca    600
gggacacgtc cattaacaca gcctacatgg agatgagcgg gctgtcatct gacgacaccg    660
ccatgtatta ctgtgcgcgc ggtgatatct ctcaggactt cgctgatgtt tggggtcaag    720
gtactctggt gaccgtctcc tca                                            743

<210> SEQ ID NO 93
<211> LENGTH: 731
```

```
<212> TYPE: DNA
<213> ORGANISM: Artificial Sequence
<220> FEATURE:
<223> OTHER INFORMATION: synthetic

<400> SEQUENCE: 93
cagtctgtcg tgacgcagcc gccctcagtg tctgcggccc caggacagaa ggtcaccatc      60
tcctgctctg gaagcagctc caacattgag aataattatg tatcatggta ccagcagctc     120
ccaggaacag cccccaaact cctcatttat gacaataata agcgaccctc agggattcct     180
gaccgattct ctggctccaa gtctggcacg tcagccaccc tgggcatcac cggactccag     240
actggggacg aggccgatta ttactgcgga acatgggata gcagcctgag tgcctatgtc     300
ttcggaactg ggaccaaggt caccgtccta ggtctagagg tggtggtggt agcggcggcg     360
gcggctctgg tggtggtgga tcccaggtgc agctacagca gtggggcgca ggactgttga     420
aaccttcgga gaccctgtcc ctcacctgcg ctgtctatgg tgggtccttc agcggttact     480
actggagctg gatccgccag tccccaggga agggactgga gtggattggg gaagtcaatc     540
atagtggcaa caccaactac aacccgtccc tcaagagtcg agtcaccatt tcactagaca     600
cgtccaagaa ccagttctcc ctgaaactga actctgtgac cgccgccgac acggccgtgt     660
attactgtgc gcgctacttc ccgccgatga tcgatgtttg gggtcaaggt actctggtga     720
ccgtctcctc a                                                          731

<210> SEQ ID NO 94
<211> LENGTH: 679
<212> TYPE: DNA
<213> ORGANISM: Artificial Sequence
<220> FEATURE:
<223> OTHER INFORMATION: synthetic

<400> SEQUENCE: 94
gaagcagctc caacattggg aataattatg tatcctggta ccagcagctc ccaagaacag      60
cccccagact cctcatttat gacaataata agcgaccctc agggattcct gaccgattct     120
ctgcctccaa gtctggcacg tcagccaccc tgggcatcac cggactccag actggggacg     180
aggccgatta ttactgcgga acatgggata gcagcctgag tgctgtggta ttcggcggag     240
ggaccaagct gaccgtccta ggtctagagg tggtggtggt agcggcggcg gcggctctgg     300
tggtggtgga tcccagctgc agctgcagga gtcgggccca ggactggtga agccttcgga     360
gaccctgtcc ctcagttgca ctgtctctgg tggctccatc agcagtagta gttactactg     420
gggctggatc cgccagcccc cagggaaggg gctggagtgg attggggaaa tcaatcatag     480
tggaagcacc aactacaacc cgtccctcaa gagtcgagtc accatatcag tagacacgtc     540
caagaaccag ttctccctga agctgagttc tgtgaccgcc gcggacacgg ccgtgtatta     600
ctgtgcgcgc tactctcatc atgttgactc tggtggttac gatgtttggg gtcaaggtac     660
tctggtgacc gtctcctca                                                  679

<210> SEQ ID NO 95
<211> LENGTH: 725
<212> TYPE: DNA
<213> ORGANISM: Artificial Sequence
<220> FEATURE:
<223> OTHER INFORMATION: synthetic

<400> SEQUENCE: 95
gacatccaga tgacccagtc tccatcctcc ctgtctgcat ctgtaggaga cagagtcacc      60
```

| | |
|---|---|
| atcacttgcc aggcgagtca ggacattagc aactatttaa attggtatca gcagaaacca | 120 |
| gggaaagccc ctaagctcct gatctacgat gcatccaatt tggaaacagg ggtcccatca | 180 |
| aggttcagtg gaagtggatc tgggacagat tttactttca ccatcagcag cctgcagcct | 240 |
| gatgattttg caacttatta ctgccaacag tataagagtt acccgctcac tttcggcgga | 300 |
| gggaccaagg tggagatcaa acgtctagag gtggtggtgg tagcggcggc ggcggctctg | 360 |
| gtggtggtgg atccgaggtg cagctggtgg agtctgggc tgaggtgaag gagcctgggt | 420 |
| cctcggtgaa ggtctcctgc aaggcttctg gaggcacctt cagcagctat ggtatcagct | 480 |
| ggattcgaca ggcccctgga caagggcttg agtggatggg agagatcatc cctatctttg | 540 |
| gtacaccaaa ctacgcgcag aagttccagg gcagagtcac gattaccgcg gacgaatcca | 600 |
| cgagcacagc ctacgtggag ctgagcagcc tgagatctga cgacacggcc gtatattact | 660 |
| gtgcgcgctc ttactacggt tacttcgatg gttggggtca aggtactctg gtgaccgtct | 720 |
| cctca | 725 |

<210> SEQ ID NO 96
<211> LENGTH: 740
<212> TYPE: DNA
<213> ORGANISM: Artificial Sequence
<220> FEATURE:
<223> OTHER INFORMATION: synthetic

<400> SEQUENCE: 96

| | |
|---|---|
| cagtctgtcg tgacgcagcc gccctcagtg tctggggccc cagggcagag ggtcaccatc | 60 |
| tcctgcactg ggagcagctc caacatcggg gcaggttatg atgtacactg gtaccagcaa | 120 |
| cttccaggaa cagcccccaa actcctcatc tatggtaaca tcaatcggcc ctcaggggtc | 180 |
| cctgaccgat tctctggctc caagtctggc acctcagcct ccctggccat cactgggctc | 240 |
| caggctgagg atgaggctga ttattactgc cagtcctatg acagcaacct gagtggttat | 300 |
| gtcttcgcaa ctgggaccaa ggtcaccgtc ctaggtctag aggtggtggt ggtagcggcg | 360 |
| gcggcggctc tggtggtggt ggatccgagg tgcagctggt ggagtccggg gctgaggtga | 420 |
| agaagcctgg ggcctcagta aaaatttcct gcaaggcatc tggatacacc ttcaccagct | 480 |
| actatatgca ctgggtgcga caggcccctg gacaagggct tgagtggatg ggaataatca | 540 |
| accctagtgg tggtagcaca agctacgcac agaagttcca gggcagagtc accatgacca | 600 |
| gggacacgtc cacgagcaca gtctacatgg agctgagcag cctgagatct gaggacacgg | 660 |
| ccgtatatta ctgtgcgcgc tctatgtacc agtacttcct ggattcttgg ggtcaaggta | 720 |
| ctctggtgac cgtctcctca | 740 |

<210> SEQ ID NO 97
<211> LENGTH: 330
<212> TYPE: PRT
<213> ORGANISM: Homo sapiens

<400> SEQUENCE: 97

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
            85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 98
<211> LENGTH: 1002
<212> TYPE: DNA
<213> ORGANISM: Homo sapiens

<400> SEQUENCE: 98
gtctcctcag cttccaccaa gggcccatcg gtcttccccc tggcaccctc ctccaagagc      60
acctctgggg gcacagcggc cctgggctgc ctggtcaagg actacttccc cgaaccggtg     120
acggtgtcgt ggaactcagg cgccctgacc agcggcgtgc acaccttccc ggccgtccta     180
cagtcctcag gactctactc cctcagcagc gtggtgaccg tgccctccag cagcttgggc     240
acccagacct acatctgcaa cgtgaatcac aagcccagca acaccaaggt ggacaagaag     300
gttgagccca aatcttgtga caaaactcac acatgcccac cgtgcccagc acctgaactc     360 ctgggggggac cgtcagtctt cctcttcccc ccaaaaccca aggacaccct catgatctcc     420
cggacccctg aggtcacatg cgtggtggtg gacgtgagcc acgaagaccc tgaggtcaag     480
ttcaactggt acgtggacgg cgtggaggtg cataatgcca agacaaagcc gcgggaggag     540
cagtacaaca gcacgtaccg tgtggtcagc gtcctcaccg tcctgcacca ggactggctg     600

-continued

```
aatggcaagg agtacaagtg caaggtctcc aacaaagccc tcccagcccc catcgagaaa    660
accatctcca aagccaaagg gcagccccga gaaccacagg tgtacaccct gcccccatcc    720
cgggaggaga tgaccaagaa ccaggtcagc ctgacctgcc tggtcaaagg cttctatccc    780
agcgacatcg ccgtggagtg ggagagcaat gggcagccgg agaacaacta caagaccacg    840
cctcccgtgc tggactccga cggctccttc ttcctctaca gcaagctcac cgtggacaag    900
agcaggtggc agcaggggaa cgtcttctca tgctccgtga tgcatgaggc tctgcacaac    960
cactacacgc agaagagcct ctccctgtct ccgggtaaat ga                      1002
```

<210> SEQ ID NO 99
<211> LENGTH: 106
<212> TYPE: PRT
<213> ORGANISM: Homo sapiens

<400> SEQUENCE: 99

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 100
<211> LENGTH: 321
<212> TYPE: DNA
<213> ORGANISM: Homo sapiens

<400> SEQUENCE: 100

```
accgtggccg ctcccctccgt gttcatcttc ccaccttccg acgagcagct gaagtccggc     60
accgcttctg tcgtgtgcct gctgaacaac ttctaccccc gcgaggccaa ggtgcagtgg    120
aaggtggaca acgccctgca gagcggcaac tcccaggaat ccgtgaccga gcaggactcc    180
aaggacagca cctactccct gtcctccacc ctgaccctgt ccaaggccga ctacgagaag    240
cacaaggtgt acgcctgcga agtgacccac cagggcctgt ctagccccgt gaccaagtct    300
ttcaaccggg gcgagtgcta g                                              321
```

<210> SEQ ID NO 101
<211> LENGTH: 105
<212> TYPE: PRT
<213> ORGANISM: Homo sapiens

<400> SEQUENCE: 101

Gln Pro Lys Ala Asn Pro Thr Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Gly Ser Pro Val

```
                35                  40                  45
Lys Ala Gly Val Glu Thr Thr Lys Pro Ser Lys Gln Ser Asn Asn Lys
 50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys Ser
            100                 105

<210> SEQ ID NO 102
<211> LENGTH: 318
<212> TYPE: DNA
<213> ORGANISM: Homo sapiens

<400> SEQUENCE: 102
cagcctaagg ccaaccctac cgtgaccctg ttccccccat cctccgagga actgcaggcc      60
aacaaggcca ccctcgtgtg cctgatctcc gacttctacc ctggcgccgt gaccgtggcc     120
tggaaggctg atggatctcc tgtgaaggcc ggcgtggaaa ccaccaagcc ctccaagcag     180
tccaacaaca atacgccgc ctcctcctac ctgtccctga ccctgagca gtggaagtcc      240 caccggtcct acagctgcca agtgacccac gagggctcca ccgtggaaaa gaccgtggct     300
cctaccgagt gctcctag                                                  318

<210> SEQ ID NO 103
<211> LENGTH: 504
<212> TYPE: PRT
<213> ORGANISM: Artificial Sequence
<220> FEATURE:
<223> OTHER INFORMATION: synthetic

<400> SEQUENCE: 103

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Ser Val Phe Gly Thr Gly Thr Lys Val Thr Val Leu Gly
            100                 105                 110

Ser Arg Gly Gly Gly Gly Ser Gly Gly Gly Gly Ser Gly Gly Gly Gly
            115                 120                 125

Ser Leu Glu Met Ala Gln Val Gln Leu Val Gln Ser Gly Ala Glu Val
        130                 135                 140

Lys Lys Pro Gly Ser Ser Val Lys Val Ser Cys Lys Ala Ser Gly Gly
145                 150                 155                 160

Thr Phe Ser Ser Tyr Thr Ile Asn Trp Val Arg Gln Ala Pro Gly Gln
                165                 170                 175

Gly Leu Glu Trp Met Gly Gly Phe Ile Pro Ile Ser Gly Thr Val Asn
            180                 185                 190
```

Tyr Ala Gln Lys Phe Gln Gly Arg Val Thr Ile Thr Ala Asp Glu Ser
        195                 200                 205

Thr Ser Thr Ala Tyr Met Glu Leu Ser Ser Leu Arg Ser Glu Asp Thr
    210                 215                 220

Ala Val Tyr Tyr Cys Ala Arg Pro Leu Asp Trp Thr Glu Asp Ile Trp
225                 230                 235                 240

Gly Gln Gly Thr Leu Val Thr Val Ser Ser Gly Gly Gly Ser Asp
                245                 250                 255

Val Gln Leu Val Gln Ser Gly Ala Glu Val Lys Lys Pro Gly Ala Ser
                260                 265                 270

Val Lys Val Ser Cys Lys Ala Ser Gly Tyr Thr Phe Thr Arg Tyr Thr
        275                 280                 285

Met His Trp Val Arg Gln Ala Pro Gly Gln Gly Leu Glu Trp Ile Gly
        290                 295                 300

Tyr Ile Asn Pro Ser Arg Gly Tyr Thr Asn Tyr Ala Asp Ser Val Lys
305                 310                 315                 320

Gly Arg Phe Thr Ile Thr Thr Asp Lys Ser Thr Ser Thr Ala Tyr Met
                325                 330                 335

Glu Leu Ser Ser Leu Arg Ser Glu Asp Thr Ala Thr Tyr Tyr Cys Ala
            340                 345                 350

Arg Tyr Tyr Asp Asp His Tyr Cys Leu Asp Tyr Trp Gly Gln Gly Thr
        355                 360                 365

Thr Val Thr Val Ser Ser Gly Glu Gly Thr Ser Thr Gly Ser Gly Gly
    370                 375                 380

Ser Gly Gly Ser Gly Gly Ala Asp Asp Ile Val Leu Thr Gln Ser Pro
385                 390                 395                 400

Ala Thr Leu Ser Leu Ser Pro Gly Glu Arg Ala Thr Leu Ser Cys Arg
                405                 410                 415

Ala Ser Gln Ser Val Ser Tyr Met Asn Trp Tyr Gln Gln Lys Pro Gly
            420                 425                 430

Lys Ala Pro Lys Arg Trp Ile Tyr Asp Thr Ser Lys Val Ala Ser Gly
        435                 440                 445

Val Pro Ala Arg Phe Ser Gly Ser Gly Ser Gly Thr Asp Tyr Ser Leu
        450                 455                 460

Thr Ile Asn Ser Leu Glu Ala Glu Asp Ala Ala Thr Tyr Tyr Cys Gln
465                 470                 475                 480

Gln Trp Ser Ser Asn Pro Leu Thr Phe Gly Gly Gly Thr Lys Val Glu
                485                 490                 495

Ile Lys His His His His His His
            500

<210> SEQ ID NO 104
<211> LENGTH: 21
<212> TYPE: PRT
<213> ORGANISM: Artificial Sequence
<220> FEATURE:
<223> OTHER INFORMATION: synthetic

<400> SEQUENCE: 104

Ser Arg Gly Gly Gly Gly Ser Gly Gly Gly Ser Gly Gly Gly Gly
1               5                   10                  15

Ser Leu Glu Met Ala
            20

<210> SEQ ID NO 105

```
<211> LENGTH: 50
<212> TYPE: DNA
<213> ORGANISM: Artificial Sequence
<220> FEATURE:
<223> OTHER INFORMATION: synthetic

<400> SEQUENCE: 105
ctagaggtgg tggtggtagc ggcggcggcg gctctggtgg tggtggatcc         50

<210> SEQ ID NO 106
<211> LENGTH: 5
<212> TYPE: PRT
<213> ORGANISM: Artificial Sequence
<220> FEATURE:
<223> OTHER INFORMATION: synthetic

<400> SEQUENCE: 106

Gly Gly Gly Gly Ser
1               5

<210> SEQ ID NO 107
<211> LENGTH: 15
<212> TYPE: DNA
<213> ORGANISM: Artificial Sequence
<220> FEATURE:
<223> OTHER INFORMATION: synthetic

<400> SEQUENCE: 107 ggcggggag gatcc                                                 15

<210> SEQ ID NO 108
<211> LENGTH: 249
<212> TYPE: PRT
<213> ORGANISM: Artificial Sequence
<220> FEATURE:
<223> OTHER INFORMATION: synthetic

<400> SEQUENCE: 108

Asp Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
            20                  25                  30

Thr Met His Trp Val Arg Gln Ala Pro Gly Gln Gly Leu Glu Trp Ile
        35                  40                  45

Gly Tyr Ile Asn Pro Ser Arg Gly Tyr Thr Asn Tyr Ala Asp Ser Val
    50                  55                  60

Lys Gly Arg Phe Thr Ile Thr Thr Asp Lys Ser Thr Ser Thr Ala Tyr
65                  70                  75                  80

Met Glu Leu Ser Ser Leu Arg Ser Glu Asp Thr Ala Thr Tyr Tyr Cys
                85                  90                  95

Ala Arg Tyr Tyr Asp Asp His Tyr Cys Leu Asp Tyr Trp Gly Gln Gly
            100                 105                 110

Thr Thr Val Thr Val Ser Ser Gly Glu Gly Thr Ser Thr Gly Ser Gly
        115                 120                 125

Gly Ser Gly Gly Ser Gly Gly Ala Asp Asp Ile Val Leu Thr Gln Ser
    130                 135                 140

Pro Ala Thr Leu Ser Leu Ser Pro Gly Glu Arg Ala Thr Leu Ser Cys
145                 150                 155                 160

Arg Ala Ser Gln Ser Val Ser Tyr Met Asn Trp Tyr Gln Gln Lys Pro
                165                 170                 175

Gly Lys Ala Pro Lys Arg Trp Ile Tyr Asp Thr Ser Lys Val Ala Ser
```

180                 185                 190
Gly Val Pro Ala Arg Phe Ser Gly Ser Gly Ser Gly Thr Asp Tyr Ser
                195                 200                 205
Leu Thr Ile Asn Ser Leu Glu Ala Glu Asp Ala Ala Thr Tyr Tyr Cys
        210                 215                 220
Gln Gln Trp Ser Ser Asn Pro Leu Thr Phe Gly Gly Gly Thr Lys Val
225                 230                 235                 240
Glu Ile Lys His His His His His His
            245

<210> SEQ ID NO 109
<211> LENGTH: 750
<212> TYPE: DNA
<213> ORGANISM: Artificial Sequence
<220> FEATURE:
<223> OTHER INFORMATION: synthetic

<400> SEQUENCE: 109

```
gacgtgcagc tggtgcagag cggagctgaa gtgaagaaac tggcgcctc cgtgaaggtg      60
tcctgcaaag ctagcggcta taccttcacc cggtacacca tgcactgggt gcgccaggca    120
cctggacagg gactggaatg gatcggctac atcaaccct cccggggcta caccaactac     180
gccgactctg tgaagggccg gttcaccatc accaccgata gtccaccag caccgcttac    240
atggaactgt cctccctgag atccgaggac accgctacct actattgcgc ccggtactac    300
gacgaccact actgcctgga ctactgggga cagggaacca cagtgaccgt gtcctctggc    360
gagggcacct ctactggatc tggggaagt ggtggttctg gcggcgctga cgacatcgtg     420
ctgacccagt ctccagccac cctgtctctg agcccaggcg agagagctac cctgtcctgc    480
agagcctccc agtccgtgtc ctacatgaat tggtatcagc agaagcctgg caaggcccct    540
aagcggtgga tctacgacac ctccaaggtg gcctctggcg tgccagcccg gttttccgga    600
tctggctctg gcaccgacta ctcccctgac catcaacagcc tggaagccga ggacgctgcc    660
acctattact gccagcagtg gtcctccaac cccctgacct ttggaggcgg caccaaggtg    720
gaaatcaagc accaccatca tcaccactga                                     750
```

<210> SEQ ID NO 110
<211> LENGTH: 10
<212> TYPE: PRT
<213> ORGANISM: Artificial Sequence
<220> FEATURE:
<223> OTHER INFORMATION: synthetic

<400> SEQUENCE: 110

Lys Leu Val Val Val Gly Ala Gly Gly Val
1               5                   10

<210> SEQ ID NO 111
<211> LENGTH: 10
<212> TYPE: PRT
<213> ORGANISM: Artificial Sequence
<220> FEATURE:
<223> OTHER INFORMATION: syntetic

<400> SEQUENCE: 111

Lys Leu Val Val Val Gly Ala Val Gly Val
1               5                   10

<210> SEQ ID NO 112
<211> LENGTH: 10

```
<212> TYPE: PRT
<213> ORGANISM: Artificial Sequence
<220> FEATURE:
<223> OTHER INFORMATION: synthetic

<400> SEQUENCE: 112

Lys Leu Val Val Val Gly Ala Cys Gly Val
1               5                   10

<210> SEQ ID NO 113
<211> LENGTH: 10
<212> TYPE: PRT
<213> ORGANISM: Artificial Sequence
<220> FEATURE:
<223> OTHER INFORMATION: synthetic

<400> SEQUENCE: 113

Lys Leu Val Val Val Gly Ala Asp Gly Val
1               5                   10

<210> SEQ ID NO 114
<211> LENGTH: 10
<212> TYPE: PRT
<213> ORGANISM: Artificial Sequence
<220> FEATURE:
<223> OTHER INFORMATION: synthetic

<400> SEQUENCE: 114

Lys Leu Val Val Val Gly Ala Ser Gly Val
1               5                   10

<210> SEQ ID NO 115
<211> LENGTH: 9
<212> TYPE: PRT
<213> ORGANISM: Artificial Sequence
<220> FEATURE:
<223> OTHER INFORMATION: synthetic

<400> SEQUENCE: 115

Leu Val Val Val Gly Ala Gly Gly Val
1               5

<210> SEQ ID NO 116
<211> LENGTH: 9
<212> TYPE: PRT
<213> ORGANISM: Artificial Sequence
<220> FEATURE:
<223> OTHER INFORMATION: synthetic

<400> SEQUENCE: 116

Leu Val Val Val Gly Ala Val Gly Val
1               5

<210> SEQ ID NO 117
<211> LENGTH: 9
<212> TYPE: PRT
<213> ORGANISM: Artificial Sequence
<220> FEATURE:
<223> OTHER INFORMATION: synthetic

<400> SEQUENCE: 117

Leu Val Val Val Gly Ala Cys Gly Val
1               5

<210> SEQ ID NO 118
<211> LENGTH: 9
<212> TYPE: PRT
```

```
<213> ORGANISM: Artificial Sequence
<220> FEATURE:
<223> OTHER INFORMATION: synthetic

<400> SEQUENCE: 118

Leu Val Val Val Gly Ala Asp Gly Val
1               5
```